United States Patent
Lipkens et al.

(10) Patent No.: US 9,822,333 B2
(45) Date of Patent: *Nov. 21, 2017

(54) ACOUSTIC PERFUSION DEVICES

(71) Applicant: FloDesign Sonics, Inc., Wilbraham, MA (US)

(72) Inventors: Bart Lipkens, Hampden, MD (US); Erik Miller, Belchertown, MA (US); Benjamin Ross-Johnsrud, Wilbraham, MA (US); Walter M. Presz, Jr., Wilbraham, MA (US); Kedar Chitale, West Hartford, CT (US); Thomas J. Kennedy, III, Wilbraham, MA (US)

(73) Assignee: FloDesign Sonics, Inc., Wilbraham, MA (US)

(*) Notice: Subject to any disclaimer, the term of this patent is extended or adjusted under 35 U.S.C. 154(b) by 143 days.

This patent is subject to a terminal disclaimer.

(21) Appl. No.: 14/975,307

(22) Filed: Dec. 18, 2015

(65) Prior Publication Data

US 2016/0102284 A1    Apr. 14, 2016

Related U.S. Application Data

(63) Continuation-in-part of application No. 14/175,766, filed on Feb. 7, 2014, now Pat. No. 9,416,344, which
(Continued)

(51) Int. Cl.
*B01D 43/00* (2006.01)
*C12M 1/00* (2006.01)
(Continued)

(52) U.S. Cl.
CPC ............ *C12M 47/02* (2013.01); *B01D 17/04* (2013.01); *B01D 17/06* (2013.01); *B01D 21/283* (2013.01);
(Continued)

(58) Field of Classification Search
CPC .......... B01D 21/283; B01D 2021/0081; B01D 43/00; B01D 17/04; B01D 17/06;
(Continued)

(56) References Cited

U.S. PATENT DOCUMENTS

| 2,667,944 A | 2/1954 | Crites |
| 3,555,311 A | 1/1971 | Weber |

(Continued)

FOREIGN PATENT DOCUMENTS

| DE | 30 27 433 A1 | 2/1982 |
| EP | 0 292 470 B1 | 11/1988 |

(Continued)

OTHER PUBLICATIONS

Alvarez et al.; Shock Waves, vol. 17, No. 6, pp. 441-447, 2008.
(Continued)

*Primary Examiner* — Walter D Griffin
*Assistant Examiner* — Cameron Allen
(74) *Attorney, Agent, or Firm* — Rick Klein, Esq.; Fay Sharpe, LLP.

(57) ABSTRACT

Acoustic perfusion devices for separating biological cells from other material in a fluid medium are disclosed. The devices include an inlet port, an outlet port, and a collection port that are connected to an acoustic chamber. An ultrasonic transducer creates an acoustic standing wave in the acoustic chamber that permits a continuous flow of fluid to be recovered through the collection port while keeping the biological cells within the acoustic chamber to be returned to the bioreactor from which the fluid medium is being drawn.

30 Claims, 40 Drawing Sheets

Related U.S. Application Data is a continuation-in-part of application No. 14/026,413, filed on Sep. 13, 2013, now Pat. No. 9,458,450, said application No. 14/026,413 is a continuation-in-part of application No. 13/844,754, filed on Mar. 15, 2013.

(60) Provisional application No. 62/256,952, filed on Nov. 18, 2015, provisional application No. 62/243,211, filed on Oct. 19, 2015, provisional application No. 62/211,057, filed on Aug. 28, 2015, provisional application No. 62/093,491, filed on Dec. 18, 2014, provisional application No. 61/761,717, filed on Feb. 7, 2013, provisional application No. 61/611,240, filed on Mar. 15, 2012, provisional application No. 61/611,159, filed on Mar. 15, 2012, provisional application No. 61/754,792, filed on Jan. 21, 2013, provisional application No. 61/708,641, filed on Oct. 2, 2012.

(51) Int. Cl.

| | | |
|---|---|---|
| *C12N 13/00* | (2006.01) | |
| *B01D 17/04* | (2006.01) | |
| *B01D 17/06* | (2006.01) | |
| *B01D 21/28* | (2006.01) | |
| *B06B 1/06* | (2006.01) | |
| *C12M 1/26* | (2006.01) | |
| *C12M 1/42* | (2006.01) | |
| *H01L 41/09* | (2006.01) | |

(52) U.S. Cl.
CPC ........... *B06B 1/0644* (2013.01); *C12M 29/10* (2013.01); *C12M 29/18* (2013.01); *C12M 33/08* (2013.01); *C12M 35/04* (2013.01); *C12N 13/00* (2013.01); *H01L 41/0973* (2013.01)

(58) Field of Classification Search
CPC ............ B01J 19/10; C02F 1/36; C12M 47/02; C12M 29/18; C12M 29/10; C12M 33/08; C12M 35/04; C12N 13/00; B06B 1/0644; H01L 41/0973
See application file for complete search history.

(56) References Cited

U.S. PATENT DOCUMENTS

| | | |
|---|---|---|
| 4,055,491 A | 10/1977 | Porath-Furedi |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,983,189 A | 1/1991 | Peterson et al. |
| 5,085,783 A | 2/1992 | Feke et al. |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,902,489 A | 5/1999 | Yasuda et al. |
| 5,912,182 A | 6/1999 | Coakley et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,332,541 B1 | 12/2001 | Coakley et al. |
| 6,391,653 B1 | 5/2002 | Letcher et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 2002/0134734 A1 | 9/2002 | Campbell et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0112841 A1* | 6/2004 | Scott ................. B01J 8/005 210/748.05 |
| 2005/0196725 A1 | 9/2005 | Fu |
| 2006/0037915 A1 | 2/2006 | Strand et al. |
| 2006/0037916 A1 | 2/2006 | Trampler |
| 2007/0224676 A1 | 9/2007 | Haq |
| 2007/0272618 A1 | 11/2007 | Gou et al. |
| 2007/0284299 A1 | 12/2007 | Xu et al. |
| 2008/0217259 A1 | 9/2008 | Siversson |
| 2008/0245745 A1 | 10/2008 | Ward et al. |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0098027 A1 | 4/2009 | Tabata et al. |
| 2009/0178716 A1 | 7/2009 | Kaduchak et al. |
| 2009/0194420 A1 | 8/2009 | Mariella, Jr. et al. |
| 2009/0226994 A1 | 9/2009 | Lemor et al. |
| 2009/0295505 A1 | 12/2009 | Mohammadi et al. |
| 2010/0000945 A1 | 1/2010 | Gavalas |
| 2010/0078384 A1 | 4/2010 | Yang |
| 2010/0124142 A1 | 5/2010 | Laugharn et al. |
| 2010/0192693 A1 | 8/2010 | Mudge et al. |
| 2010/0193407 A1 | 8/2010 | Steinberg et al. |
| 2010/0206818 A1* | 8/2010 | Leong ................. B01D 21/283 210/748.05 |
| 2010/0255573 A1 | 10/2010 | Bond et al. |
| 2010/0261918 A1 | 10/2010 | Chianelli et al. |

(56) References Cited

U.S. PATENT DOCUMENTS

| | | |
|---|---|---|
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0154890 A1 | 6/2011 | Holm et al. |
| 2011/0166551 A1 | 7/2011 | Schafer |
| 2011/0262990 A1 | 10/2011 | Wang et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0175012 A1 | 7/2012 | Goodwin et al. |
| 2012/0325727 A1 | 12/2012 | Dionne et al. |
| 2012/0328477 A1 | 12/2012 | Dionne et al. |
| 2012/0329122 A1 | 12/2012 | Lipkens et al. |
| 2013/0175226 A1 | 7/2013 | Coussios et al. |
| 2013/0277316 A1 | 10/2013 | Dutra et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |

FOREIGN PATENT DOCUMENTS

| | | |
|---|---|---|
| EP | 1 254 669 B1 | 11/2002 |
| GB | 2 420 510 A | 5/2006 |
| WO | WO 87/07178 A1 | 12/1987 |
| WO | WO 00/41794 | 7/2000 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/161463 A2 | 12/2011 |
| WO | WO 2013/043297 A1 | 3/2013 |
| WO | WO 2013/055517 A1 | 4/2013 |
| WO | WO 2014/124306 A1 | 8/2014 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
European Search Report of European Application No. 11769474.5 dated Oct. 10, 2012.
International Search Report and Written Opinion of International Application No. PCT/US2013/037404 dated Jun. 21, 2013.
Annex to Form PCT/ISA/206—Communication Relating to the Results of the Partial International Search Report, dated Jul. 18, 2013.
International Search Report and Written Opinion of International Application No. PCT/US2013/050729 dated Sep. 25, 2013.
International Search Report for corresponding PCT Application Serial No. PCT/US2014/015382 dated May 6, 2014.
International Search Report for PCT Application No. PCT/US2015/024365 dated Sep. 23, 2015.
International Search Report and Written Opinion for International Application No. PCT/US2015/066884, dated Mar. 22, 2016.

\* cited by examiner

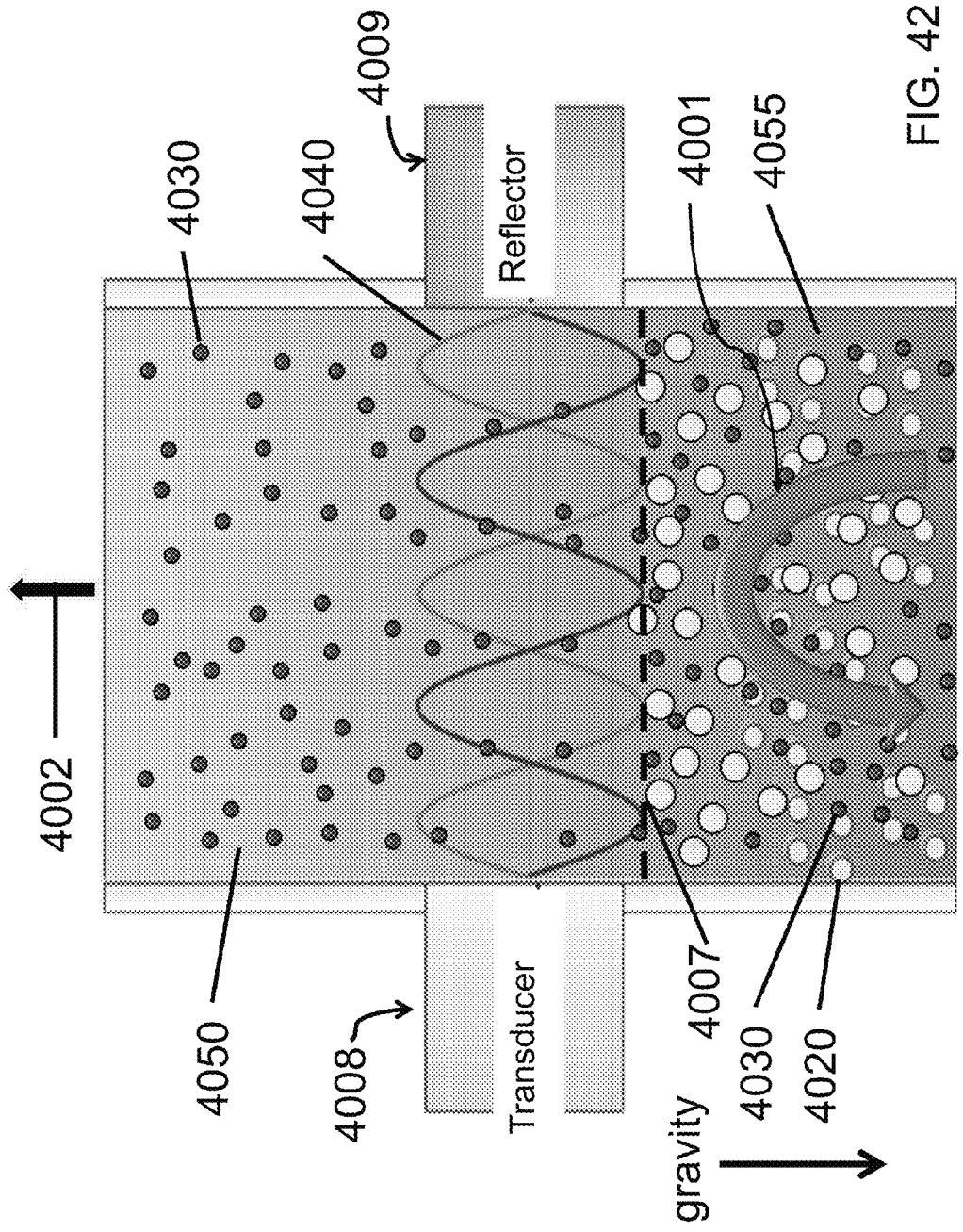

ACOUSTIC PERFUSION DEVICES

CROSS-REFERENCE TO RELATED APPLICATIONS

This application claims priority to U.S. Provisional Patent Application Ser. No. 62/256,952, filed on Nov. 18, 2015, and to U.S. Provisional Patent Application Ser. No. 62/243,211, filed on Oct. 19, 2015, and to U.S. Provisional Patent Application Ser. No. 62/211,057, filed on Aug. 28, 2015, and to U.S. Provisional Patent Application Ser. No. 62/093,491, filed on Dec. 18, 2014. This application is also a continuation-in-part of U.S. patent application Ser. No. 14/175,766, filed on Feb. 7, 2014, which claims priority to U.S. Provisional Patent Application Ser. No. 61/761,717, filed on Feb. 3, 2013, and is also a continuation-in-part of U.S. patent application Ser. No. 14/026,413, filed on Sep. 13, 2013. U.S. patent application Ser. No. 14/026,413 is a continuation-in-part of U.S. Ser. No. 13/844,754, filed Mar. 15, 2013, which claims the benefit of U.S. Provisional Patent Application Ser. No. 61/611,159, filed Mar. 15, 2012, and of U.S. Provisional Patent Application Ser. No. 61/611,240, filed Mar. 15, 2012, and of U.S. Provisional Patent Application Ser. No. 61/708,641, filed on Oct. 2, 2012, and of U.S. Provisional Patent Application Ser. No. 61/754,792, filed Jan. 21, 2013. These applications are incorporated herein by reference in their entireties.

STATEMENT REGARDING FEDERALLY SPONSORED RESEARCH

This invention was made with government support under Grant No. IIP-1330287 (Amendment 003, Proposal No. 1458190) awarded by the National Science Foundation. The government has certain rights in the invention.

BACKGROUND

The field of biotechnology has grown tremendously in the last 20 years. This growth has been due to many factors, some of which include the improvements in the equipment available for bioreactors, the increased understanding of biological systems and increased knowledge as to the interactions of materials (such as monoclonal antibodies and recombinant proteins) with the various systems of the human body.

Improvements in equipment have allowed for larger volumes and lower cost for the production of biologically derived materials such as recombinant proteins. This is especially prevalent in the area of pharmaceuticals, where the successes of many types of new drug therapies have been directly due to the ability to mass produce these materials through protein-based manufacturing methods.

One of the key components that is utilized in the manufacturing processes of new biologically based pharmaceuticals is the bioreactor and the ancillary processes associated therewith. An area of growth in the bioreactor field has been with the perfusion process. The perfusion process is distinguished from the fed-batch process by its lower capital cost and continuous (rather than batch) operation.

In the fed-batch process, a culture is seeded in a bioreactor. The gradual addition of a fresh volume of selected nutrients during the growth cycle is used to improve productivity and growth. The product is recovered after the culture is harvested. The discontinuous fed-batch bioreactor process has been attractive because of its simplicity and also due to carryover from well-known fermentation processes. However, a fed-batch bioreactor has high start-up costs, and generally has a large volume to obtain a cost-effective amount of product at the end of the growth cycle. After the batch is completed, the bioreactor must be cleaned and sterilized, resulting in nonproductive downtime.

A perfusion bioreactor processes a continuous supply of fresh media that is fed into the bioreactor while growth-inhibiting byproducts are constantly removed. The nonproductive downtime can be reduced or eliminated with a perfusion bioreactor process. The cell densities achieved in perfusion culture (30-100 million cells/mL) are typically higher than for fed-batch modes (5-25 million cells/mL). These improvements have led to lower contamination in the harvest and better yields without significant increase in cost. However, a perfusion bioreactor requires a cell retention device to prevent escape of the culture when byproducts are being removed. These cell retention systems add a level of complexity to the perfusion process, requiring management, control, and maintenance for successful operation. Operational issues such as malfunction or failure of the cell retention equipment has previously been a problem with perfusion bioreactors, which has limited their attractiveness in the past.

BRIEF DESCRIPTION

The present disclosure relates, in various embodiments, to acoustic devices which are used for perfusion biomanufacturing. More particularly, the devices are coupled to an associated bioreactor. Within the bioreactor, biomolecules, such as recombinant proteins or monoclonal antibodies, are produced. The acoustic device is then used for separating these desirable products from the cells on a continuous basis, and the cells are continuously returned to the bioreactor. Generally, a fluid medium containing the cells and the desired products are passed or flowed through the acoustic device and separated therein by multi-dimensional standing wave(s). The fluid medium can be continuously flowed into the device, with desired products being continuously removed. The acoustic perfusion device returns healthy viable cells to the bioreactor while desired products are harvested and flowed downstream for further processing, e.g., additional filtering, chromatography, etc. Additionally, the cell culture media in the bioreactor is clarified as cell fragments are also allowed to pass into the harvest stream and thereby out of the fluid medium being recycled to the bioreactor. This results in lower overall cell culture media usage, corresponding to a predicted cost savings of up to $20,000 per day for large bioreactors.

Disclosed in various embodiments are acoustic perfusion devices, comprising: an acoustic chamber; an inlet port, an inlet flow path leading from the inlet port to the acoustic chamber; an outlet port for recirculating fluid flowing through the device back to its source (e.g. a bioreactor); at least one collection or harvest port for collecting a product stream of fluid exiting the acoustic chamber; and at least one ultrasonic transducer in the acoustic chamber below the at least one harvest port, the at least one ultrasonic transducer including a piezoelectric material driven by a voltage signal to create an acoustic standing wave across a collection or harvest flow path leading from the acoustic chamber to the at least one collection or harvest port. The acoustic standing wave may be planar or multi-dimensional, or a combination of such waves may be present within the acoustic chamber (generally from multiple transducers). The acoustic standing wave can be thought of as a "force field" that holds back whole cells but permits smaller materials such as the desired biomolecules (e.g. recombinant proteins and/or monoclonal antibodies) and cell fragments, to pass through and be removed from the fluid that is returned to the bioreactor.

The outlet port is generally below the inlet port, and is generally located at a bottom end of the device.

As mentioned above, the device may have one or more collection or harvest ports at the top of the device. In some more specific embodiments, the device may have a total of two harvest ports spaced apart from each other on the top end of the device.

In particular embodiments, the inlet port is at a first end of the device at a first height, the at least one ultrasonic transducer is at a second height above the first height, and a bottom wall extends from the inlet port to the outlet port. The outlet port may be located at a second end of the device opposite the first end. The bottom wall may be concave, relative to a line between the inlet port and the outlet port. The device may include an upper wall above the inlet flow path. The inlet port, the outlet port, and the at least one harvest port are sometimes all located on a front wall of the device. The front wall itself may be planar (i.e. flat).

The device can further comprise a reflector located in the acoustic chamber opposite the at least one ultrasonic transducer. Alternatively, the device can have a total of two ultrasonic transducers located on opposite sides of the harvest flow path at the same height and facing each other, or additional ultrasonic transducers can be located on multiple sides of the collection/harvest flow path. A reflector may be located between the two ultrasonic transducers. There may also be a plurality of transducer/reflector pairs located as appropriate to form planar, multi-dimensional, or combinations of such acoustic standing wave(s).

In particular embodiments, the acoustic standing wave results in an acoustic radiation force having an axial force component and a lateral force component that are of the same order of magnitude.

In other embodiments of the device disclosed herein, the inlet flow path leads from the inlet port downwards towards a bottom end of the device and past the outlet port, and then upwards to the acoustic chamber. Sometimes, the inlet port and the at least one harvest port are both located on a top wall of the device, and the outlet port is located on a front wall of the device. The at least one ultrasonic transducer may be mounted in a rear wall or a front wall of the device. The bottom wall of this acoustic chamber can be a sloped planar surface. The reflector may be made of a transparent material.

The inlet flow path may be shaped to generate a tangential flow path below an acoustic field generated by the acoustic standing wave. In still additional versions seen herein, the inlet flow path enters the acoustic chamber on a first side of the device, and the outlet port is located (i) on the first side of the device or (ii) on a second opposite side. The inlet port can be located on a front side of the device, and the at least one harvest port can be located on a top wall of the device. The at least one transducer can be located on a front side or a rear side of the device. In more particular embodiments, there can be two transducers, one on the front side and one of the rear side. In yet other particular embodiments, there is an ultrasonic transducer on the front or rear side, and a reflector located on the respective rear or front side opposite the transducer.

The device may be attached to a mounting piece having holes for attachment.

Also disclosed are methods for separating cells from a fluid medium containing the cells. The fluid medium is flowed through an acoustic perfusion device of the structure described above, having at least one ultrasonic transducer.

The at least one ultrasonic transducer is driven to create the acoustic standing wave. A fluid enriched in cells can be collected from the outlet port and a clarified fluid, depleted in cells, can be collected from the at least one harvest port.

In particular embodiments, the flow rate through the collection/harvest flow path is at least one order of magnitude smaller than a flow rate through the inlet flow path. In specific embodiments, a flow rate of the fluid medium entering the device through the inlet port is about 1 liter per minute and a flow rate of the fluid depleted in cells exiting the device through the at least one collection/harvest port is about 10 milliliters per minute. Alternatively, the ratio of the flow rate entering through the inlet port to the flow rate exiting through the at least one collection/harvest port is such that the acoustic standing wave is not overcome by the main body of cells, or in other words so that a large volume of cells do not begin exiting the device through the collection/harvest port(s).

The methods may further comprise pulling the fluid medium through the device using a first pump attached to the at least one harvest port of the device and a second pump attached to the outlet port of the device.

Also disclosed herein are flow devices adapted to (i) receive a flowing mixture containing a primary fluid and cells; and (ii) to use a first acoustic standing wave to continuously draw off a harvest fluid stream depleted in cells from the flowing mixture, thereby changing the cell concentration of the flowing mixture. A pressure rise may be generated at an edge of the acoustic standing wave, along with an acoustic radiation force. This "edge effect" acts as a barrier at the edge of the acoustic standing wave. The frequency of the acoustic standing wave may be modified such that different contrast factor materials may be held back or allowed through the acoustic standing wave.

The device may further comprise a secondary flow chamber in which the harvest fluid stream depleted in cells passes through a second acoustic standing wave having a frequency higher than the first acoustic standing wave.

Also disclosed herein are flow devices that comprise: at least one inlet for receiving a flowing mixture of a primary fluid and cells, an ultrasonic transducer that produces a first ultrasonic acoustic standing wave and uses a pressure rise and an acoustic radiation force generated at an edge of the first ultrasonic acoustic standing wave to separate the flowing mixture into a primary high cell concentration fluid stream and a secondary harvest fluid stream; an outlet port for the primary high cell concentration fluid stream; and at least one collection port for the secondary harvest fluid stream. A bleed port can also be present for extracting a concentrated fluid/cell mixture.

The device may further comprise a secondary flow chamber in which the secondary harvest fluid stream passes through a second acoustic standing wave having a frequency higher than the first ultrasonic acoustic standing wave.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

In FIG. 29B, the y-axis is the particle count from 0 to 200 in intervals of 10. The x-axis is the particle diameter in microns from 6 to 50 in intervals of 2. The total number of particles is 5539, the mean particle size is 16.78 microns, standard deviation of 6.76 microns, and mode particle size of 10.56 microns.

In FIG. 30B, the y-axis is the particle count from 0 to 300 in intervals of 20. The x-axis is the particle diameter in microns from 6 to 50 in intervals of 2. The total number of particles is 2919, the mean particle size is 10.08 microns, standard deviation of 3.75 microns, and mode particle size of 8.99 microns.

FIG. 35A is at a frequency of 2.218 MHz. FIG. 35B is at a frequency of 2.2465 MHz. FIG. 35C is at a frequency of 2.3055 MHz. For all three graphs, the left-side scale is indicated with text at the top of the scale reading "×10$^{-6}$" or "×10$^{-7}$", and is in units of inches. The right-side scale is indicated with text at the top of the scale reading "×10$^6$", and is in units of Pascals. The y-axis runs from −0.8 to 1.6 in intervals of 0.2. The x-axis runs from −0.5 to 1.5 in intervals of 0.5.

FIG. 42 is a picture illustrating a second mode of operation during perfusion, in which cells are prevented from entering an acoustic standing wave field while smaller particles are permitted to pass through the field and into the harvest stream. The device is operated vertically, with an arrow indicating the direction of gravity.

DETAILED DESCRIPTION

Figure 1:
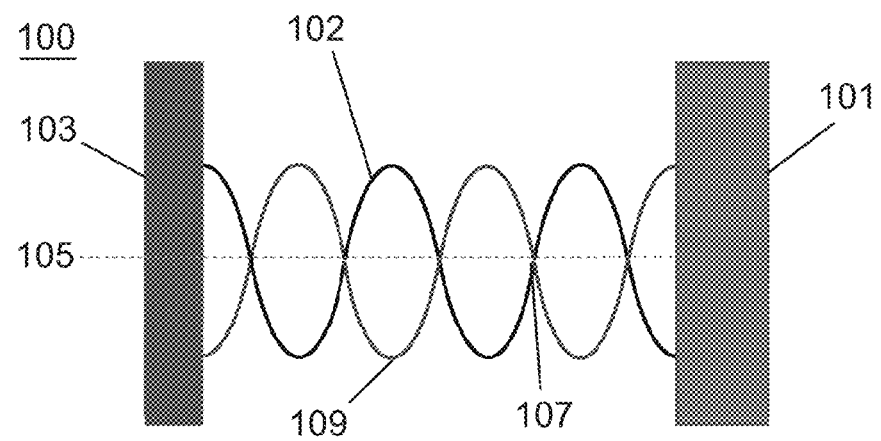
FIG. 1 illustrates a single standing acoustic wave generated by an ultrasonic transducer and a reflector.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The present application refers to "the same order of magnitude." Two numbers are of the same order of magnitude if the quotient of the larger number divided by the smaller number is a value less than 10.

Bioreactors are useful for making biomolecules such as recombinant proteins or monoclonal antibodies. Very generally, cells are cultured in a bioreactor vessel with media in order to produce the desired product, and the desired product is then harvested by separation from the cells and media in an acoustic perfusion device, such as the device of the present disclosure. The acoustic filtering device permits the withdrawal of some desired product, a small portion of the media, and cellular fragments/debris smaller than the cells, with the remainder being recycled back to the bioreactor (particularly the cells). The use of mammalian cell cultures including Chinese hamster ovary (CHO), NSO hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies used in various applications such as pharmaceuticals or vaccines. Two general types of bioreactor processes exist: fed-batch and perfusion.

While fed-batch reactors are the norm currently, due mainly to the familiarity of the process to many scientists and technicians, perfusion technology is growing at a very fast rate. Many factors favor the use of a perfusion bioreactor process, primarily because it is conducive to continuous production. The capital and start-up costs for perfusion bioreactors are lower, smaller upstream and downstream capacity is required, throughput can be higher, the process is continuous, and the process uses smaller volumes and fewer seed steps than fed-batch methods. A perfusion bioreactor process also lends itself better to development, scale-up, optimization, parameter sensitivity studies, and validation.

A perfusion bioreactor may also be utilized to generate cells that would be utilized in a cell therapy process. In this type of perfusion bioreactor, biological cells such as CAR T-cells, Jurkat T-cells and the like are cultured in a perfusion bioreactor. The acoustic standing wave used in the perfusion devices of the present disclosure can be used to separate viable and nonviable cells after the transfection process. This allows for improved efficacy of the inoculation of the patient with this T-cell therapy as only viable cells are utilized. The nonviable cells and cell fragments are separated out through the perfusion process, with these materials going into the secondary flow and exiting the bioreactor.

Recent developments in perfusion bioreactor technology also favor its use. Control technology and general support equipment is improving for perfusion bioreactors, increasing the robustness of perfusion processes. The perfusion process can now be scaled up to bioreactors having a volume up to 1000 liters (L). Better cell retention systems for perfusion bioreactors result in lower cell loss and greater cell densities than have been seen previously. Cell densities greater than 50 million cells/mL are now achievable, compared to fed-batch cell densities of around 20 million cells/mL. Lower contamination and infection rates have improved the output of perfusion bioreactors. Higher product concentrations in the harvest and better yields without significant increase in cost have thus resulted for perfusion processes.

Perfusion bioreactors are particularly attractive because of the continuous production of the biomolecules from the expressing cell culture, and shorter residence time of said biomolecules in the process prior to harvest. The target cells are held back by a filtration process, such as tangential flow filtration (TFF) or alternating tangential flow filtration (ATF) while the expressed biomolecules are extracted from the perfusion bioreactor. The cells are then returned to the bioreactor to ensure they receive the nutrition and oxygen to maintain the production of the overall cell culture. In the perfusion reactor process, the cells continue to multiply so it is also necessary to bleed off some of the cell culture population throughout the perfusion production process.

The TFF and ATF processes of filtration have several issues, such as clogging/fouling and loss of biomolecule product (particularly at high cell densities), all directly related to the nature of the hollow fiber membranes used in the filtration. It is therefore desirable to find a new filtration process that does not clog and minimizes loss of the desired biomolecule product. In addition, TFF and ATF will retain all cellular debris and fines within the bioreactor, which is not desirable. A process capable of distinguishing between cell retention while allowing for the passing of cell debris and fines may therefore be favorable.

Briefly, the present disclosure relates to acoustic perfusion devices capable of generating multi-dimensional acoustic standing wave(s) from one or more piezoelectric transducers, where the transducers are electrically such that they move in a multi-mode displacement pattern rather than a "piston" mode of vibration. Through this manner of acoustic standing wave generation, a higher lateral trapping force is generated than if the piezoelectric transducer is excited in a "piston" mode where only one large standing wave is generated. Thus, with the same input power to a piezoelectric transducer, the multi-dimensional acoustic standing waves can have a higher lateral trapping force compared to a planar acoustic standing wave. The input power is tunable for a controlled flow. This can be used to facilitate proteinaceous fluid purification of a fluid stream coming from a bioreactor. Alternatively, the acoustic standing wave may also be a planar standing wave where the piezoelectric transducer is excited in the piston mode, generating a planar wave. The acoustic standing wave(s) may also be a combination of planar and multi-dimensional acoustic standing waves. All of these standing waves generate an "edge effect" such that the cells from the bioreactor are held back and the biomolecule product expressed from the cells, cell fragments and small debris are allowed to pass through.

Acoustophoresis is a low-power, no-pressure-drop, no-clog, solid-state approach to particle separation from fluid dispersions (i.e., it is used to achieve separations that are more typically performed with porous filters, but it has none of the disadvantages of filters). In particular, the acoustic perfusion devices of the present disclosure are suitable for use with macro-scale bioreactors for separations in flowing systems with high flow rates. The acoustic perfusion device is designed to create a high intensity multi-dimensional ultrasonic standing wave that results in an acoustic radiation force that can overcome the combined effects of fluid drag and buoyancy or gravity at low flow rates. As a result, the radiation force acts as a filter that prevents targeted particles (e.g., biological cells) from crossing the plane of the standing wave. As explained above, the trapping capability of a standing wave may be varied as desired, for example by varying the flow rate of the fluid, the acoustic radiation force, and the shape of the acoustic filtering device to maximize cell retention through trapping and settling. This technology offers a green and sustainable alternative for separation of secondary phases with a significant reduction in cost of energy. Excellent particle separation efficiencies have been demonstrated for particle sizes as small as one micron.

Generally, the scattering of the acoustic field off the particles results in a three-dimensional acoustic radiation force, which acts as a three-dimensional trapping field. The acoustic radiation force is proportional to the particle volume (e.g., the cube of the radius) when the particle is small relative to the wavelength. It is proportional to frequency and the acoustic contrast factor. It also scales with acoustic energy (e.g., the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the lateral and axial acoustic forces on the trapped particles results in formation of tightly packed clusters through concentration, agglomeration and/or coalescence of particles that settle through enhanced gravity (particles heavier than the host fluid) or buoyancy (particles lighter than the host fluid). Additionally, secondary inter-particle forces, such as Bjerkness forces, aid in particle agglomeration.

Most biological cell types present a higher density and lower compressibility than the medium in which they are suspended, so that the acoustic contrast factor between the cells and the medium has a positive value. As a result, the axial acoustic radiation force (ARF) drives the cells towards the standing wave pressure nodes. The axial component of the acoustic radiation force drives the cells, with a positive contrast factor, to the pressure nodal planes, whereas cells or other particles with a negative contrast factor are driven to the pressure anti-nodal planes. The radial or lateral component of the acoustic radiation force is the force that traps the cells. The radial or lateral component of the ARF is larger than the combined effect of fluid drag force and gravitational force. For small cells or emulsions the drag force $F_D$ can be expressed as:

$$\vec{F}_D = 4\pi\mu_f R_p (\vec{U}_f - \vec{U}_p) \left[ \frac{1 + \frac{3}{2}\hat{\mu}}{1 + \hat{\mu}} \right],$$

where $U_f$ and $U_p$ are the fluid and cell velocity, $R_p$ is the particle radius, $\mu_f$ and $\mu_p$ are the dynamic viscosity of the fluid and the cells, and $\hat{\mu}=\mu_p/\mu_f$ is the ratio of dynamic viscosities. The buoyancy force $F_B$ is expressed as:

$$F_B = \frac{4}{3}\pi R_p^3 (\rho_f - \rho_p) g.$$

For a cell to be trapped in the multi-dimensional ultrasonic standing wave, the force balance on the cell must be zero, and, therefore, an expression for lateral acoustic radiation force $F_{LRF}$ can be found, which is given by:

$$F_{LRF} = F_D + F_B.$$

For a cell of known size and material property, and for a given flow rate, this equation can be used to estimate the magnitude of the lateral acoustic radiation force.

The theoretical model that is used to calculate the acoustic radiation force is based on the formulation developed by Gor'kov. The primary acoustic radiation force $F_A$ is defined as a function of a field potential U, $F_A=-\nabla(U)$, where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda\sigma^2},$$

$$f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $<>$ indicates time averaging over the period of the wave.

Gor'kov's theory is limited to particle sizes that are small with respect to the wavelength of the sound fields in the fluid and the particle, and it also does not take into account the effect of viscosity of the fluid and the particle on the radiation force. Additional numerical models have been developed for the calculation of the acoustic radiation force for a particle without any restriction as to particle size relative to wavelength. These models also include the effect of fluid and particle viscosity, and therefore are a more accurate calculation of the acoustic radiation force. The models that were implemented are based on the theoretical work of Yurii Ilinskii and Evgenia Zabolotskaya as described in AIP Conference Proceedings, Vol. 1474-1, pp. 255-258 (2012).

Desirably, the ultrasonic transducer(s) generates a multi-dimensional standing wave in the fluid that exerts a lateral force on the suspended particles to accompany the axial force. Typical results published in literature state that the lateral force is two orders of magnitude smaller than the axial force. In contrast, the technology disclosed in this application provides for a lateral force to be of the same order of magnitude as the axial force. However, in certain embodiments described further herein, the device use both transducers that produce multi-dimensional acoustic standing waves and transducers that produce planar acoustic standing waves. For purposes of this disclosure, a standing wave where the lateral force is not the same order of magnitude as the axial force is considered a "planar acoustic standing wave." The lateral force component of the total acoustic radiation force (ARF) generated by the ultrasonic transducer(s) of the present disclosure is significant and is sufficient to overcome the fluid drag force at linear velocities of up to 1 cm/s, and to create tightly packed clusters, and is of the same order of magnitude as the axial force component of the total acoustic radiation force.

Figure 40:
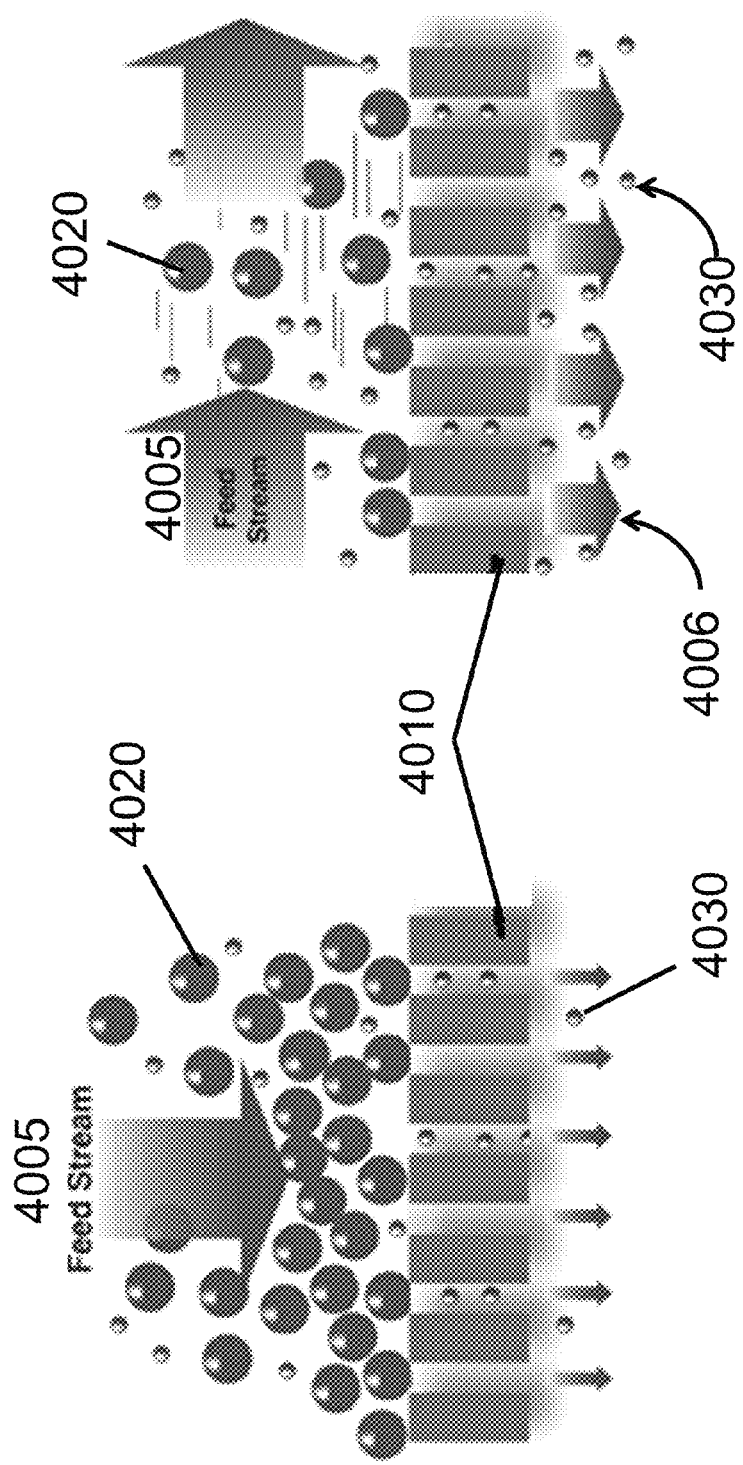
FIG. 40 is a prior art illustration showing direct flow filtration (DFF) and tangential flow filtration (TFF).

It may be helpful to contrast the technology of the present disclosure with that of prior filtration technology. FIG. 40 shows two prior art filtration methods. The left-hand side of FIG. 40 illustrates direct flow filtration (DFF). In DFF, the entire feed stream 4005 of fluid and particles is directed towards the filter. The filter 4010 holds back the particles 4020 that are larger than the filter's pore size, whereas smaller particles 4030 and the fluid pass through the filter. The right-hand side of FIG. 40 illustrates tangential flow filtration (TFF). In TFF, the feed stream is not directed towards the filter. Rather, the feed stream is directed tangentially to the filter, such that a majority of the feed stream passes tangentially over the filter surface. Typically, this feed stream is recirculated to pass by the filter more than once. A much smaller filtrate stream 4006 is pulled through the filter membrane containing the smaller particles 4030. One advantage of TFF over DFF is that the tangential stream reduces the clogging and fouling of the filter and the formation of a gel layer that sits on top of the filter.

In the devices of the present disclosure, during startup, the fluid ensonified by the acoustic standing wave is clarified by the process of trapping cells and growing them into tightly packed clusters, such that continuous gravitational separation of the clusters of cells takes place. Since there is a limited amount of new cells flowing into this volume, this results in a rapid clarification of the fluid subjected to the acoustic standing wave. When this state is reached, the system can be described as including two fluids: a first fluid containing the desired product and small cell fragments/debris (which has passed through the acoustic standing wave), and a second fluid containing the bioreactor fluid and all of the cells (which are held back by the acoustic standing wave). The two fluids may be of different effective acoustic properties, such as density and speed of sound, with a well-defined interface between these two fluids. The interface is generally located near the lower edge of the acoustic standing wave field, generating an "acoustic edge effect". The first fluid (i.e., the fluid that has been clarified and contains the product, some cells, and cell fragments) is downstream of the interface and represents the harvest flow and occupies the volume of fluid ensonified by the acoustic standing wave field. The second fluid (i.e., the fluid containing the bioreactor fluid and most of the cells) is upstream of the interface. These two different fluids can be seen in FIG. 33.

The acoustic standing wave field exerts an acoustic radiation pressure (i.e. a pressure rise) and a force at the acoustic edge of the acoustic field on the interface between the two fluids, thereby keeping the upstream cells from entering the acoustic field. The occurrence of the radiation pressure and the force on the interface allows for the first fluid containing the product to pass through the interface while retaining the cells in the upstream fluid. The cells that are held back by the effect of the acoustic radiation force at the interface between the two fluids can be continuously returned to the bioreactor to ensure they receive the nutrition and oxygen to maintain the production of the overall cell culture.

The circulating motion of the flow field underneath the interface transports the cells that are retained by the acoustic field back to the bioreactor. The circulating flow motion is driven by the primary recirculation stream and can be optimized with acoustic chamber geometry variations for maximum system efficiency. This will be discussed further below with respect to FIG. 33 below.

Figure 41:
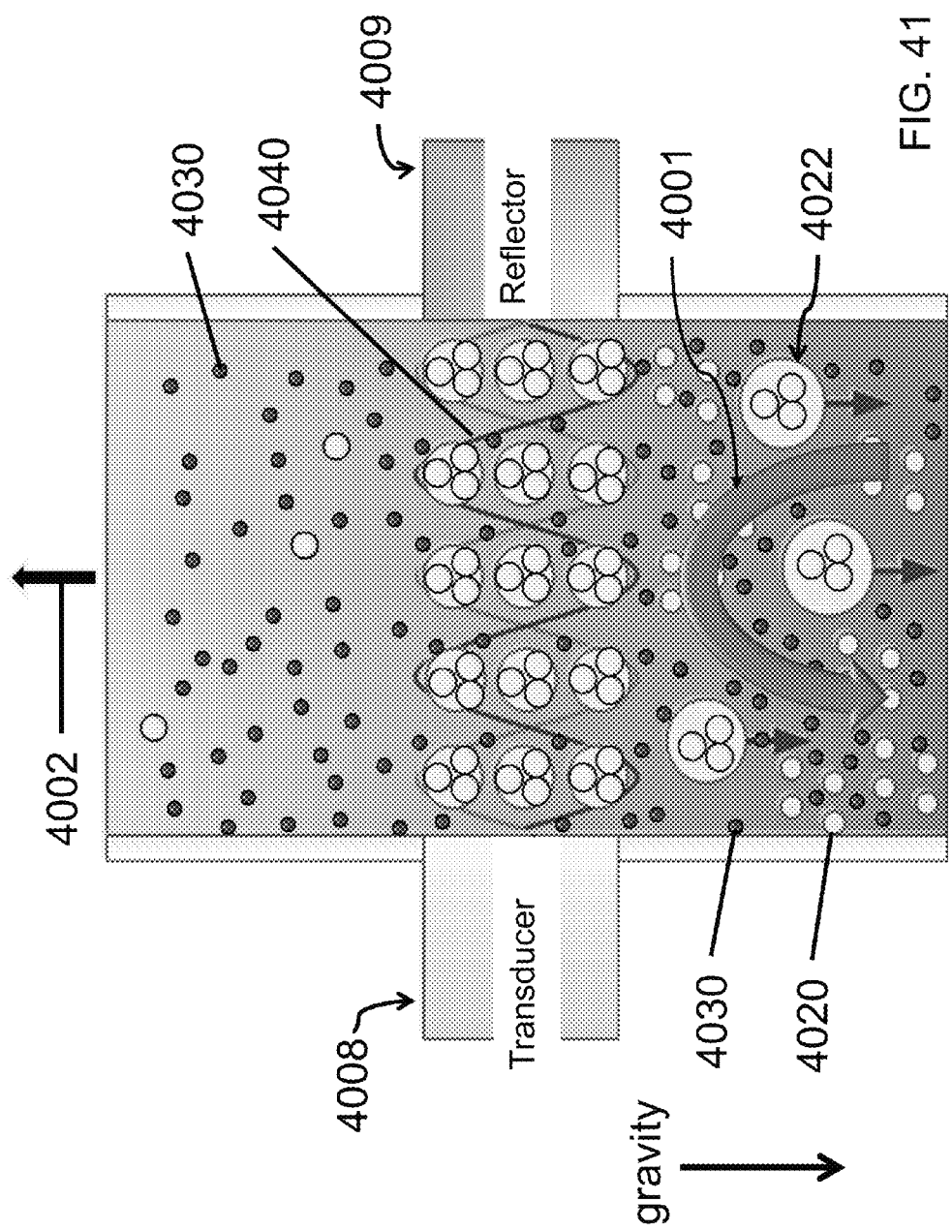
FIG. 41 is a picture illustrating a first mode of operation during perfusion, in which cells are trapped, clustered, and separated from a harvest stream. The device is operated vertically, with an arrow indicating the direction of gravity.

During perfusion, the acoustic perfusion devices of the present disclosure have multiple possible modes of operation. One of these modes may be dominant in the device or they may occur concurrently depending on the distribution of cells and fluid within the device. In a first mode of operation illustrated in FIG. 41 (Mode 1), the fluid containing cells 4020 (light color) enters the acoustic standing wave field 4040, which is produced here between transducer 4008 and reflector 4009. A multi-dimensional acoustic standing wave traps the cells at specific points, packs the cells into tightly packed clusters 4022, and continuously separates the clusters through enhanced gravitational settling. The cell clusters settle out, enter the tangential flow path (indicated by arrow 4001) and are redirected to the bioreactor by the recirculation stream. Smaller particles 4030 (darker color) are not trapped by, and pass through, the acoustic standing wave, to be harvested. The harvest flow direction is indicated by arrow 4002. The orientation of this device is significant, and the direction of gravity is also indicated.

The second mode of operation (Mode 2) is illustrated in FIG. 42, where the acoustophoretic system creates a strong barrier for cells and prevents cells from entering the acoustic field. Here, a barrier of cells is established between the two fluids through the edge effect of the acoustic standing wave. A first clarified fluid stream 4050 contains the smaller particles/desired byproducts 4030 within the acoustic standing wave field and the harvest stream. A second fluid stream 4055 contains the retained cells 4020 upstream of the acoustic standing wave field. The harvest flow direction is indicated by arrow 4002. In this mode of operation, an acoustic edge effect (indicated by dotted line 4007) is realized. Very generally, the acoustic edge effect holds the cells back and prevents them from entering the acoustic field while a portion of the fluid stream containing the produced biomolecules and cell fragments is permitted to pass through the barrier created by the acoustic edge. The tangential flow path underneath the acoustic edge (arrow 4001) collects the retained cells and flows them back into the main recirculation stream and back to the bioreactor. This will also be discussed further below with respect to FIG. 32. Again, the direction of gravity is indicated.

Figure 32:
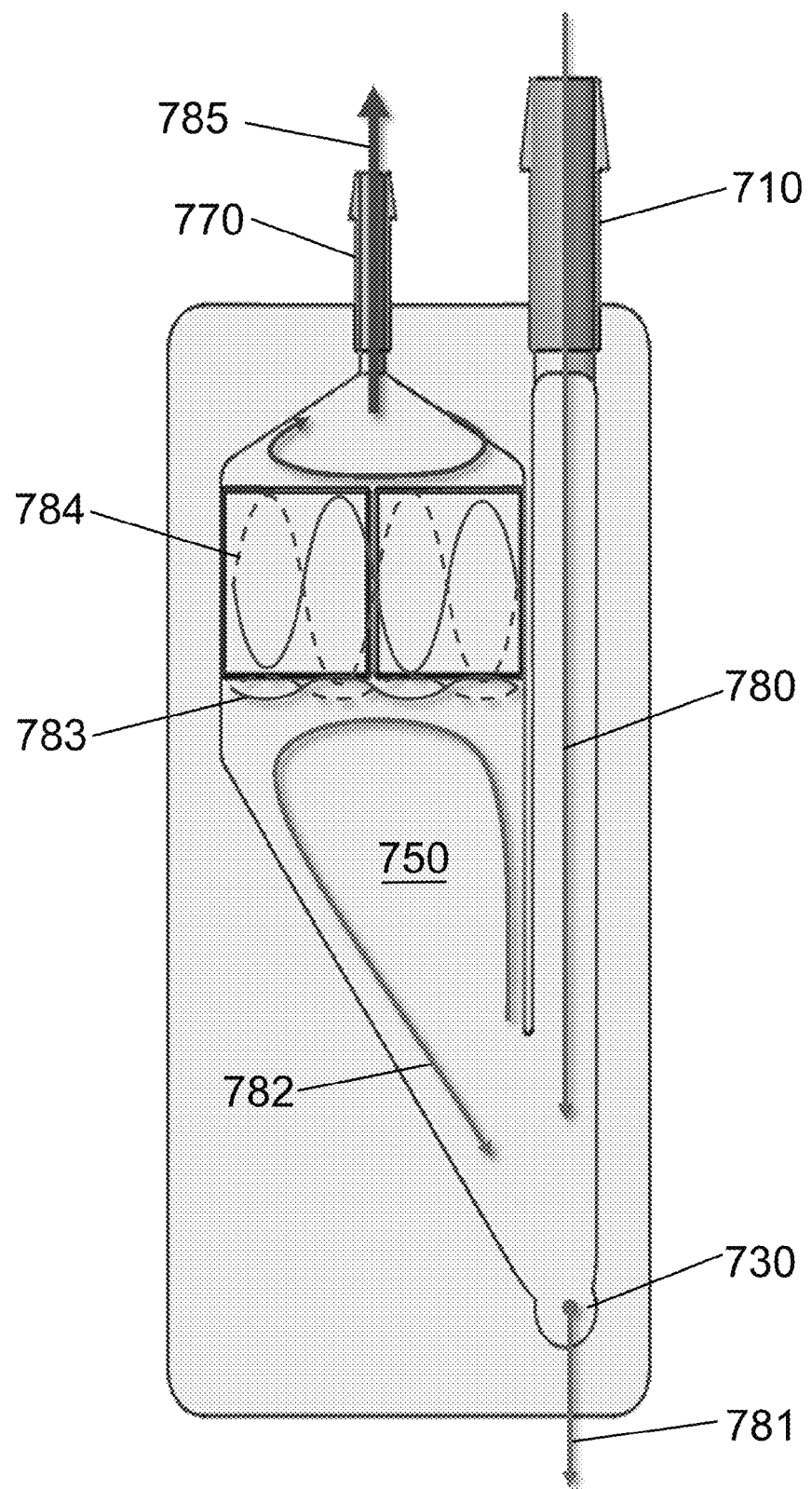
FIG. 32 is a front view of the device of FIG. 27, showing the flow paths, acoustic field, and acoustic edge effect.

In perfusion applications, the setup of the acoustophoretic device is similar to that of TFF. A feed stream containing the cells, cell debris, fines, and product, i.e., protein, flows from the bioreactor into the perfusion system. A portion of the stream flows in a tangential fashion along the lower edge of the acoustic standing wave and is recirculated back to the bioreactor. A smaller portion of the feed stream is harvested, i.e., diverted and flows through the acoustic standing wave. Here the acoustic standing wave functions very similarly to the filter in TFF, preventing the cells from entering the acoustic field. The harvest stream contains smaller particles such as cell debris and fines as well as the desired biomolecule product. The cells that are retained by the acoustic standing wave are transported by the recirculation stream back to the bioreactor. FIG. 32, discussed further herein, also illustrates a perfusion device that uses a tangential flow stream.

Perfusion applications typically entail high cell densities, e.g., >50 million cells/mL, and lower harvest velocities contrary to cell clarification or oil/water applications. The two fluid streams also have different effective acoustic properties, i.e., speed of sound and density of the media/cell mixture. As cell density increases, the difference in acoustic properties of the two fluid streams will be more pronounced as well. The acoustic standing wave field will now exert an acoustic radiation pressure, i.e., a pressure rise, on the second fluid stream, enriched with cells, as well as acoustic radiation forces on the cells suspended in the fluid. This radiation pressure and radiation force act at the interface between the two fluids which coincides with the upstream edge of the acoustic field. When this "acoustic edge" effect of acoustic radiation force is sufficiently strong, it will prevent the cells from entering the acoustic field. Equally important is a tangential flow path to collect the retained cells and transport them back to the bioreactor.

Figure 37:
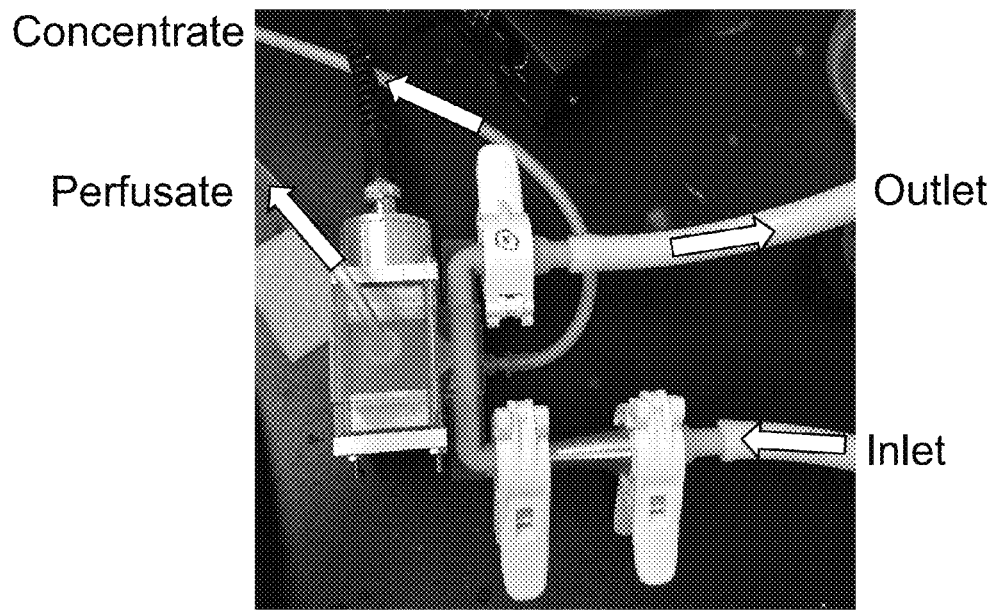
FIG. 37 is a picture (top view) of an acoustic perfusion device of the present disclosure. Arrows indicate the flow into the inlet port; the flow out of the outlet port; the clarified fluid flow out the top of the device and the flow of concentrate out the bottom of the device.

The acoustic edge effect may also be referred to as an acoustic wall effect and results from the edge of the acoustic field exerting a strong lateral force, i.e., in the direction of the harvest flow and perpendicular to the axis of the acoustic standing wave, on the suspended particles, thereby keeping the relatively larger sized particles from entering the acoustic field and allowing only clarified fluid (i.e., the fluid containing the smaller-sized product) to enter the acoustic field, thereby creating an acoustic perfusion cell retention device. In this way, only the clarified fluid can escape and the cells are held down by the radiation force. This force is never positive, meaning that it always holds the cells down at the interface, i.e., the force is acting in the upstream flow direction, not allowing them to escape the acoustic edge. The multiple peaks in the power curve (see discussion of FIG. 37 below) show the existence of multiple modes of operation including planar resonance modes and multi-dimensional modes of operation, indicating that this type of operation can be generated through utilization of planar and multi-dimensional standing waves alike. In systems having 1"×1" dimensions, there exists a planar resonance about every 30 kHz. FIG. 37 shows evidence of additional peaks indicating the existence of the multi-dimensional modes. Per unit power, these modes can be equally or even more effective as the planar resonance modes. As explained above, the cells that are held back by the acoustic radiation force may then picked up by the scrubbing motion of the flow field (i.e., the recirculating flow underneath the interface), and be continuously returned to the bioreactor to ensure they receive the nutrition and oxygen to maintain the production of the overall cell culture.

The clarified fluid contains both the desired products and cell fragments, all of which are smaller than whole viable cells. In this way, the media that is returned to the bioreactor is clarified of cell fragments. Cell fragments absorb media without producing desired product, making the perfusion process less efficient. Thus, there is an efficiency gain and a cost savings obtained by removing these cell fragments using the acoustic perfusion devices of the present disclosure. Further clarification of the clarified fluid may be achieved downstream using a second device or a secondary flow chamber that contains another transducer-reflector pair that operates at a higher frequency. This traps and agglomerates particles having a size of about 10 microns or less that may have inadvertently passed through the original acoustic standing wave, in the same manner as described before. Yet another transducer-reflector pair operating at still higher frequencies, 3 MHz to 20 MHz, may be utilized to trap, agglomerate and drop out the small cell fragments and debris that have passed through the initial acoustic standing wave and the "edge effect". This triple-clarified fluid containing the desired biomolecules can then directly enter a sterile filter. For example, the original acoustic perfusion device may operate at frequencies up to about 4 MHz. It is contemplated that the frequency of this second and third acoustic standing wave field would be from about 6 MHz to about 20 MHz, and possibly higher, to trap smaller sized cell fragments.

Figure 33:
FIG. 33 is a composite photograph showing the acoustic perfusion device of FIG. 27 in two operating modes. On the left, the device is in startup or cell settling mode. On the right, the device is in steady cell retention mode.

During startup of a bioreactor at low cell density, e.g., 2 million cells/mL, the first described mode of operation dominates (FIG. 33, left image). As cell density in the bioreactor increases over time, the mode of operation gradually switches from mode 1 to mode 2, and both modes may coexist at the same time.

When an acoustic standing wave is employed for perfusion in a bioreactor with an already high cell density, e.g., 50 million cells/mL, the device typically starts in the first mode of operation (FIG. 33, left image), until the volume of fluid within the acoustic standing wave is clarified, at which point the operation gradually switches to the second described mode of operation (FIG. 33, right image). At times, during operation, an instability, usually manifested as a perturbation or oscillation of the interface between the two fluids, may grow sufficiently strong such that cells enter the volume of fluid within the acoustic standing wave, at which point, for a short period of time, the device acts in a combined mode of operation, where both modes are active (i.e., the edge effect prevents cells from entering the acoustic field as explained above, while the acoustic field clarifies the cells that have entered the volume of fluid within the acoustic standing wave field). Once the tightly packed cell clusters have settled out (i.e., once the volume of fluid within the acoustic standing wave has been sufficiently clarified), the mode of operation is then again that of the second described mode of operation including the acoustic edge effect. It is important to note that the device can operate in both/either of the modes of operation, as described above, without external switching. In other words, the properties of the fluid streams, e.g., cell concentrations in the streams, and acoustic field dictate which mode dominates.

The acoustic standing wave(s) perfusion devices of the present disclosure are operated differently compared to prior acoustic filter usages, previously described in literature. Previously, acoustophoresis was operated such that the protein-producing materials, such as Chinese hamster ovary cells (CHO cells), the most common host for the industrial production of recombinant protein therapeutics, were trapped within the ultrasonic standing wave (i.e., remain in a stationary position). Cells were retained in an acoustic field by causing individual cells to migrate towards the pressure nodal planes of the planar acoustic standing wave. There, as the cells were retained in the standing wave, there was also a physical scrubbing of the cell culture media flowing past, whereby more cells were trapped as they came in contact with the cells that were already held within the standing wave. The standing wave was then intermittently shut off to allow the cells to drop out of the standing wave and return to the bioreactor.

In contrast, in the present disclosure, the ultrasonic standing waves are used as a blanket or selector or "force field". Rather than trapping the biological cells within the standing wave, fluid flows through the perfusion device in a manner such that gravity first operates on the biological cells, causing them to sink. The standing wave is created near the top of the filtering device and acts like a filter to prevent the cells from entering the acoustic field and exiting through the top of the filtering device (i.e., acting similar to a force field holding the cells back from entering the acoustic field). Thus, two output streams are created, one output stream retaining the cells and exiting through a port at the bottom of the device, and the other output stream being depleted in cells and exiting through a port at the top of the device (the cell concentration in the two output streams being compared to each other). There is almost no reliance on agglomeration of the cells within the acoustic field, which is particularly advantageous in certain applications because no retention time of the cells in the acoustic filtering device is required.

Described another way, the acoustic perfusion device has two fluid streams flowing at different rates. The main fluid stream, carrying the expressing cell culture, culture media, product, and other bioreactor constituents, enters the device and is partially diverted into a secondary, lower volume, lower flow fluid stream. This secondary fluid stream passes through the multi-dimensional acoustic standing wave, where the multi-dimensional acoustic standing wave (or generally an acoustic standing wave) holds back the main cell culture and allows the expressed biomolecules, the monoclonal antibodies and recombinant proteins, along with other small particles such as submicron and micron-sized cell debris, to pass through and be further collected and processed outside/downstream of the bioreactor. The main fluid stream, containing the main cell culture, is then recycled back to the bioreactor.

In another application, the acoustic perfusion devices can act as a retention device and cell washing device for cell therapy applications. In continuous cell-culture applications, such as autologous and allogeneic cell therapy, it is necessary to purify, isolate, and then proliferate cells that are initially harvested at a very low cell-density. Relatively few cells seed a bioreactor, in which cell numbers must be increased. Further processing steps such as concentrating, washing, and media exchange are all needed for various applications. The commonality in all these applications is the need to continuously circulate, add, and/or remove media while retaining cells in a bioreactor (which may be traditional or single-use) with no effect to their viability. The acoustic cell retention systems described herein operate over a range of cell recirculation rates, efficiently retain cells over a range of perfusion (or media removal rates), and can be tuned to fully retain or selectively pass some percentage of cells through power or frequency manipulation. Power and flow rates can all be monitored and used as feedback in an automated control system. Specialty flow paths may also be used such that a small volume of the main fluid flow is "sipped" off and the expressed biomolecules are separated from the main cell culture.

One advantage of acoustophoresis is that the acoustic radiation force does not harm or negatively affect the biological cells or the desired biomolecule product. Moreover, perfusion is continuous, such that the cell culture is kept viable and desired products can be continually recovered therefrom.

In a perfusion bioreactor system, it is desirable to be able to filter and separate the viable biological cells from the expressed materials that are in the fluid stream (i.e., cell culture media) and cellular debris. As previously mentioned, such biological cells may include Chinese hamster ovary (CHO) cells, whose cell genome is manipulated to express large biomolecules. Such biomolecules can include recombinant proteins or monoclonal antibodies, and are the desired product to be recovered.

The acoustic perfusion devices of the present disclosure are designed to maintain a high intensity multi-dimensional acoustic standing wave that can act as a filter, permitting smaller particles (such as recombinant proteins or cellular debris) to pass through while excluding larger particles (such as viable cells). Generally, the device is driven by an oscillator and amplifier (not shown), and the device performance is monitored and controlled by a computer (not shown). It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results (i.e. the acoustic beam may be turned on and shut off at different time periods or rates).

FIG. 1 illustrates a single standing wave system 100 that is comprised of a reflector plate 101 and an ultrasonic transducer 103 that is set to resonate so as to form a standing wave 102. Excitation frequencies typically in the range from 100 kHz to 100 MHz are applied by the transducer 103. One or more multi-dimensional standing waves are created between the transducer 103 and the reflector 101. An ideal standing wave is the sum of two propagating waves that are equal in frequency and intensity and that are traveling in opposite directions, i.e. from the transducer to the reflector and back. The propagating waves constructively interfere with each other and thus generate the standing wave. A dotted line 105 is used to indicate the zero-amplitude of the wave. A node is a point where the wave has minimum amplitude, and is indicated with reference numeral 107. An anti-node is a point where the wave has maximum amplitude, and is indicated with reference numeral 109.

Figure 2:
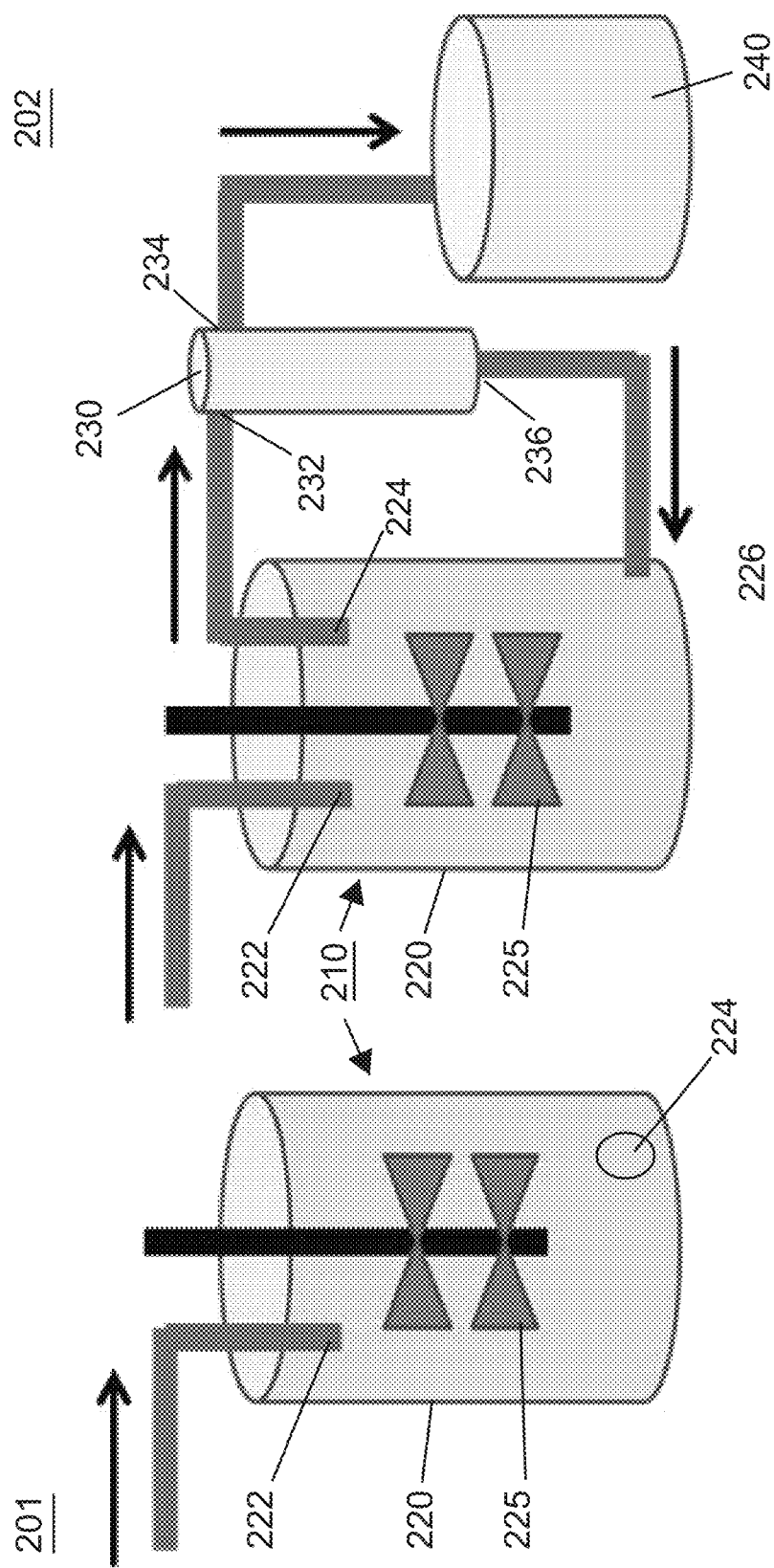
FIG. 2 is an illustration comparing a fed-batch bioreactor system with a perfusion bioreactor system.

FIG. 2 is a schematic diagram that compares a fed-batch bioreactor system 201 (left side) with a perfusion bioreactor system 202 (right side). Beginning with the fed-batch bioreactor on the left, the bioreactor 210 includes a reaction vessel 220. The cell culture media is fed to the reaction vessel through a feed inlet 222. An agitator 225 is used to circulate the media throughout the cell culture. Here, the agitator is depicted as a set of rotating blades, though any type of system that causes circulation is contemplated. The bioreactor permits growth of a seed culture through a growth/production cycle, during which time debris, waste and unusable cells will accumulate in the bioreactor and the desired product (e.g. biomolecules such as monoclonal antibodies, recombinant proteins, hormones, etc.) will be produced as well. Due to this accumulation, the reaction vessel of a fed-batch process is typically much larger than that in a perfusion process. The desired product is then harvested at the end of the production cycle. The reaction vessel 220 also includes an outlet 224 for removing material.

Turning now to the perfusion bioreactor 202 on the right-hand side, again, the bioreactor includes a reaction vessel 220 with a feed inlet 222 for the cell culture media. An agitator 225 is used to circulate the media throughout the cell culture. An outlet 224 of the reaction vessel is fluidly connected to the inlet 232 of an acoustic perfusion device 230 of the present disclosure, and continuously feeds the bioreactor contents (containing cells and desired product) to the filtering device. The perfusion device is located downstream of the reaction vessel, and separates the desired product from the cells. The acoustic perfusion device 230 has two separate outlets, a product outlet 234 and a recycle outlet 236. The product outlet 234 fluidly connects the acoustic perfusion device 230 to a containment vessel 240 downstream of the perfusion device, which receives the flow of the desired product (plus media) from the perfusion device. From there, further processing/purification can occur to isolate/recover the desired product. For example, further downstream of this acoustic perfusion device may be additional filters such as an ATF, TFF, depth filter, centrifuge, etc. The recycle outlet 236 fluidly connects the acoustic perfusion device 230 back to a recycle inlet 226 of the reaction vessel 220, and is used to send the cells and cell culture media back into the reaction vessel for continued growth/production. Put another way, there is a fluid loop between the reaction vessel and the perfusion device. The reaction vessel 220 in the perfusion bioreactor system 202 has a continuous throughput of product and thus can be made smaller. The filtering process is critical to the throughput of the perfusion bioreactor. A poor filtering process will allow for only low throughput and result in low yields of the desired product.

Figure 3:
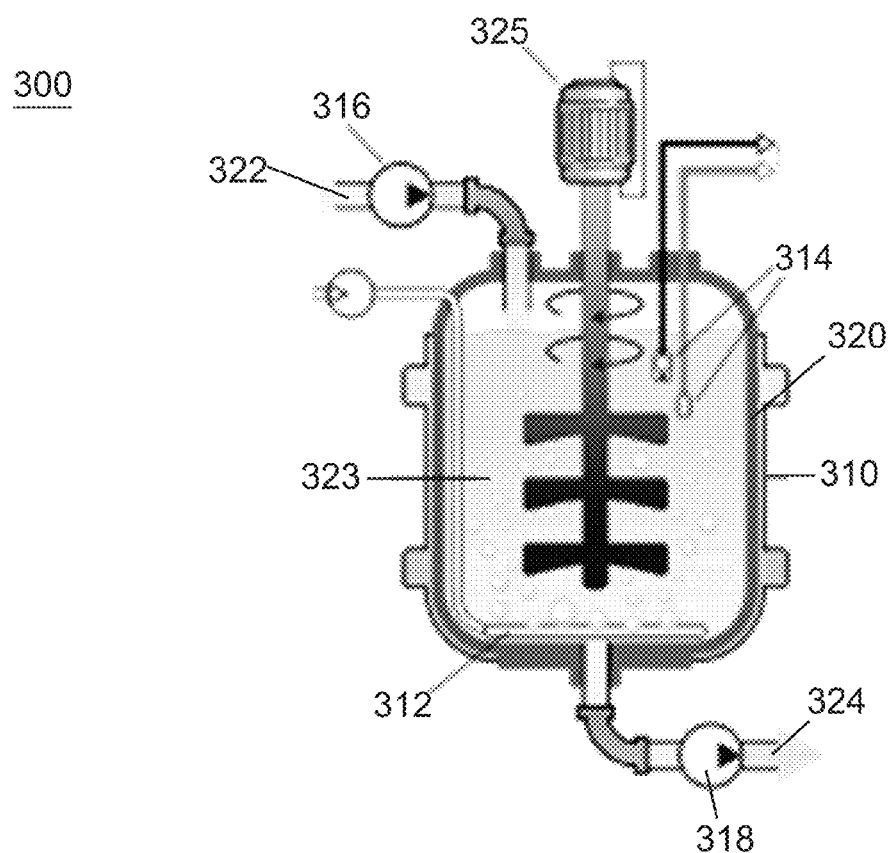
FIG. 3 is a cross-sectional view that shows the various components of a stirred-tank bioreactor.

FIG. 3 is a cross-sectional view of a generic bioreactor 300 that is useful for the systems of the present disclosure. As illustrated here, the bioreactor includes a reaction vessel 320 having an internal volume 323. A feed inlet 322 at the top of the vessel is used to feed cell culture media into the vessel. An agitator 325 is present. An outlet 324 is shown at the bottom of the vessel. A thermal jacket 310 surrounds the reaction vessel, and is used to regulate the temperature of the cells/media. An aerator 312 is located on the bottom of the vessel for providing gas to the internal volume. Sensors 314 are shown at the top right of the vessel. A pump 316 is illustrated for feeding the cell culture media into the vessel, as is another pump 318 for removing cell culture media from the vessel.

The perfusion systems described above use an acoustic perfusion device of the present disclosure. The contents of the bioreactor are continuously flowed through the acoustic perfusion device to capture the desired products.

Figure 4:
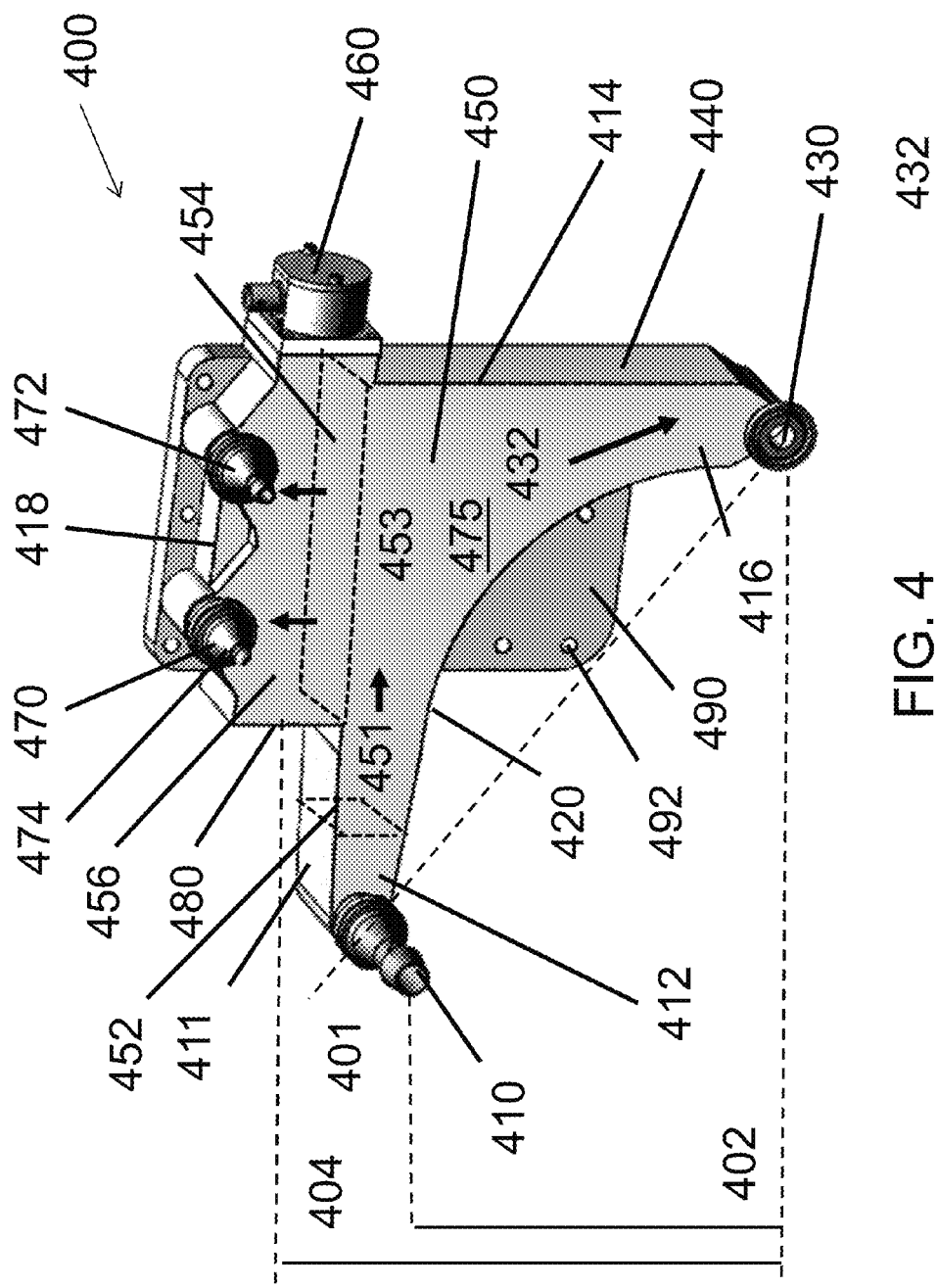
FIG. 4 is a perspective view of one exemplary embodiment of an acoustic perfusion device of the present disclosure, having two collection or harvest ports and a single ultrasonic transducer.

FIG. 4 is a first embodiment of an acoustic perfusion device 400 that can be used with the previously-described systems. The device includes an inlet port 410, an outlet port 430, a first collection port 470, a bottom wall 420, and an acoustic chamber 450. The acoustic chamber 450 can also be referred to as a fluid cell.

The inlet port 410 is located at a first end 412 of the device. Generally, the inlet port 410 is fluidly connected to an associated bioreactor and serves as the inlet through which the fluid medium with cells, fines, and product is introduced to the device. An inlet flow path 451 leads from the inlet port 410 to the acoustic chamber 450, which contains an internal volume. An upper wall 411 can be present above the inlet flow path leading from the inlet port to the acoustic chamber, the upper wall having a substantially horizontal orientation. The inlet flow path has a cross-sectional area 452 (illustrated by the dotted square).

The inlet port 410 is located at a first height 402 above the outlet port 430, which defines a bottom end of the device. Put another way, the outlet port 430 is located below the acoustic chamber 450 or below the inlet port 410, or at the bottom end 416 of the device. The placement of the outlet port 430 below the inlet port 410 ensures that fluid flow through the device is passively urged by gravity towards the outlet port 430, and that a hydraulic head is created within the device. The outlet port 430 may also be referred to as a fluid recycle port because the host fluid is recycled or returned from the device to the associated bioreactor through the outlet port 430. As illustrated here, the outlet port 430 is also located at a second end 414 of the device, opposite the first end 412. The first end 412 and second end 414 can be considered as being opposite ends of an x-axis, while the bottom end 416 and top end 418 can be considered as being opposite ends of a z-axis.

The first collection port 470 is located above the acoustic chamber 450 at the top end 418 of the device, and is fluidly connected to the acoustic chamber. The device may include additional collection ports, such as second collection port 472, which is spaced apart from the first collection port 470. The first and second collection ports 470, 472 are generally used to harvest and recover a portion of the desired biomolecule byproducts from the device. A collection or harvest flow path 453 leads from the acoustic chamber to the collection ports 470, 472. The collection flow path has a cross-sectional area 454 (illustrated by the dotted square). In some particular embodiments, the cross-sectional area 454 of the collection flow path is greater than the cross-sectional area 452 of the inlet flow path. This is one method by which the flow rate of fluid through the collection ports 470, 472 can be made much lower than the incoming flow rate of fluid. When used in perfusion biomanufacturing, the collection ports can also be referred to as perfusion or harvest ports. Because fluid depleted in cells and enriched in desired biomolecule products, cell debris, and other fines is harvested, the collection ports can also be referred to as harvest ports, and the collection flow path can also be referred to as the harvest flow path.

In this embodiment, the bottom wall 420 extends from the inlet port 410 to the outlet port 430 of the device. The exact shape of the bottom wall 420 can vary to obtain the desired fluid flow. As illustrated here, the bottom wall 420 curves from the inlet port 410 to the outlet port 430 of the device. Relative to a line between the inlet port 410 and the outlet port 430, illustrated as dotted line 401, the bottom wall 420 has a concave curve. An outlet flow path 432 leads from the acoustic chamber 450 to the outlet port 430.

As illustrated here, a first ultrasonic transducer 460 is located on a sidewall 440 of the device at a second height 404 that is above the first height 402 (i.e. closer to the top end 418 of the device) and below the collection ports 470, 472. This volume above the acoustic chamber 450 and below the collection ports 470, 472 is identified here as a harvest or collection zone 456. The first ultrasonic transducer 460 includes a piezoelectric material that can be driven by a voltage signal to create a multi-dimensional standing wave in the acoustic chamber 450 across the collection flow path 453. An acoustic radiation force field thus separates the acoustic chamber 450 from the collection ports 470, 472.

In the embodiment of FIG. 4, the device includes a reflector 480 located on a wall opposite from the first ultrasonic transducer 460. The reflector is also located at the second height (i.e. the same height as the transducer). Together, the transducer 460 and reflector 480 generate a multi-dimensional acoustic standing wave, as illustrated in FIG. 1.

The inlet port 410, outlet port 430, and the collection ports 470, 472 are, in this illustrated embodiment, all located on a front wall 475 of the device. It is also contemplated that these ports can face in any other direction, as desired. The front wall 475 is illustrated here as having a flat or planar face, and has a constant thickness. However, the shape of the front wall may also vary if desired, for example to change the cross-sectional areas 452, 454. Finally, the rear wall of the device is attached to a mounting piece 490, which contains holes 492 for attaching the perfusion device to a surface for operation.

In use, the fluid medium containing biological cells and smaller molecules enters the acoustic chamber 450 through the inlet port 410. Inside the acoustic chamber, gravity acts to drag the biological cells downwards towards the outlet port 430. A passive settling process occurs in the acoustic chamber, creating a fluid with a relatively high concentration of biological cells at the bottom end 416 of the device, and a fluid with a relatively lower concentration of biological cells at the top end 418 of the device. The vast majority of incoming fluid, and thereby, the large majority of the cell population never passes through the acoustic standing wave(s). The fluid with the high concentration of biological cells is pumped back to the bioreactor, and the fluid with the relatively low concentration of biological cells (and also containing desired biomolecules) is pumped out and collected though the collection port(s) 470, 472. The acoustic standing wave(s) of the device act to prevent significant numbers of biological cells from exiting through the collection port(s) 470, 472.

The flow rate through the collection or harvest flow path 453 is, in various embodiments, at least one order of magnitude smaller than the flow rate through the inlet flow path 451. In more particular embodiments, the flow rate of the fluid medium entering the device through the inlet port is about 1 liter per minute (L/min) and the flow rate of the fluid depleted in cells exiting the device through the collection port(s) is about 10 milliliters per minute (mL/min). In some tests, bioreactors having a size of 2 liters to 10 liters have been tested with solutions containing up to 10% yeast and up to 50 million cells/m L. The flow rate through the inlet port has been from about 0.75 L/min to about 3 L/min, with the flow rate through the collection flow path (i.e. all collection ports together) being about 1 mL/min to about 30 mL/min. A 95% cell recovery rate has been achieved.

The acoustic perfusion devices of the present disclosure can filter very high cell densities, around 100 million cells per mL and possibly in the range of about 60 million to about 120 million cells per mL, whereas other filtering technologies such as ATF can only filter at densities less than 80 million cells per mL. Unlike hollow fiber membranes, the acoustic standing wave(s) can also be tuned to allow passage of cells if desired, as well as allow the passage of fines/debris. This can act as a cleaning operation for the bioreactor. Continuous, steady-state operation is possible without pressure fluctuations, and the product stream does not accumulate in the bioreactor or the filtering device.

The acoustic perfusion device can be made of appropriate materials known in the art. Such materials include high density polyethylene (HDPE), other plastics, and potentially metals and glasses. It has been found very convenient for the device to be transparent, so that fluid flow and ultrasonic transducer operation can be visually confirmed.

Figure 5:
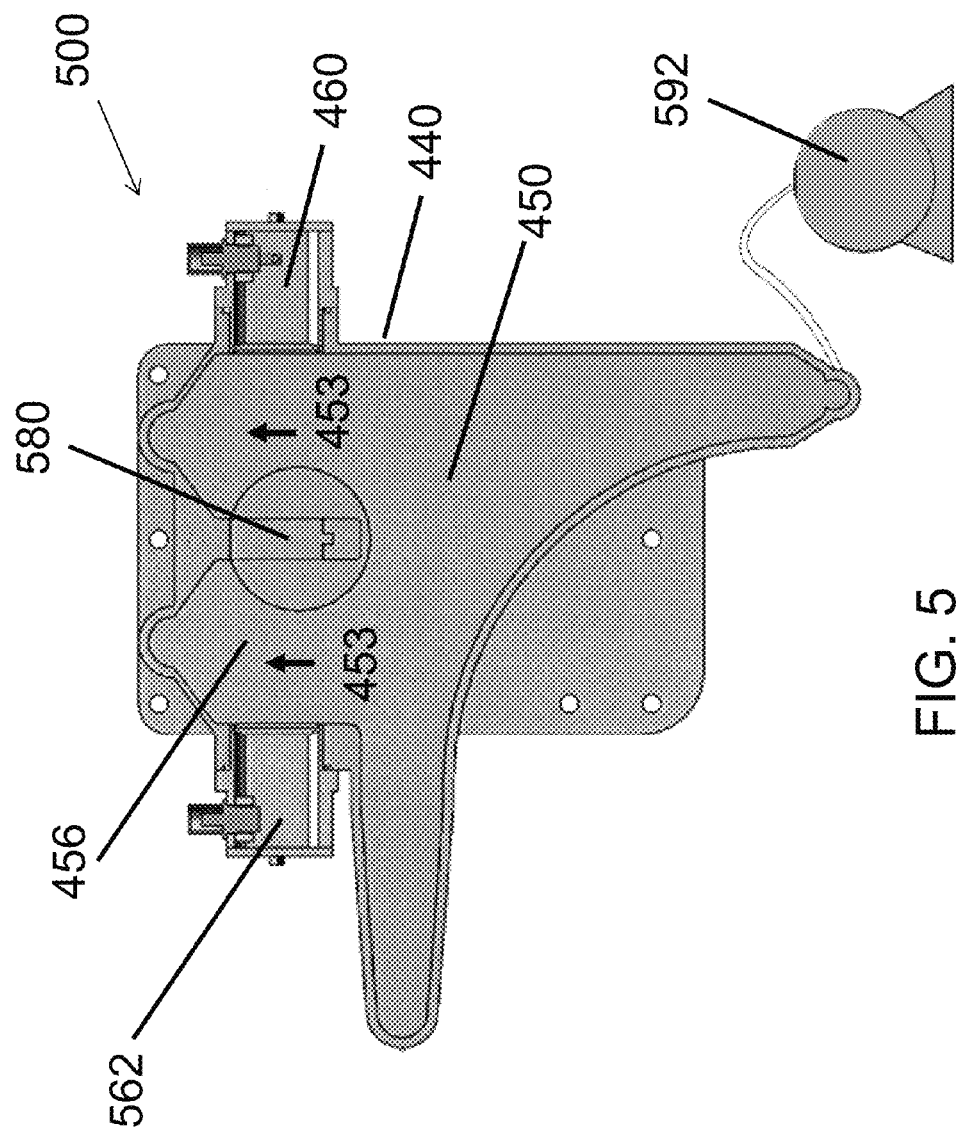
FIG. 5 shows a second exemplary embodiment of an acoustic perfusion device of the present disclosure, with a single reflector located between two ultrasonic transducers.

FIG. 5 shows another embodiment of an acoustic perfusion device 500. This embodiment is very similar to the device 400 depicted in FIG. 4. The main difference is that the acoustic perfusion device 500 of FIG. 5 has a first ultrasonic transducer 460 on one sidewall of the device and a second ultrasonic transducer 562 on an opposite sidewall 440 thereof in the collection zone 456. Put another way, the two transducers 460, 562 are located on opposite sides of the collection flow path 453. With this arrangement, the reflector 580 is located within the collection zone 456 between the first and second ultrasonic transducers 460, 562. The transducers are oriented so that the reflector 580 and first and second ultrasonic transducers 460, 562 create multi-dimensional standing wave(s) in the fluid cell 450 as described above, or put another way the transducers are facing each other. Also illustrated is the outflow pump 592 attached to the outlet port 430 of the device, which is used to control the flow rate of the fluid medium flowing through the device. Not illustrated here is the pump attached to the collection ports (not visible) of the filtering device 500.

Figure 6:
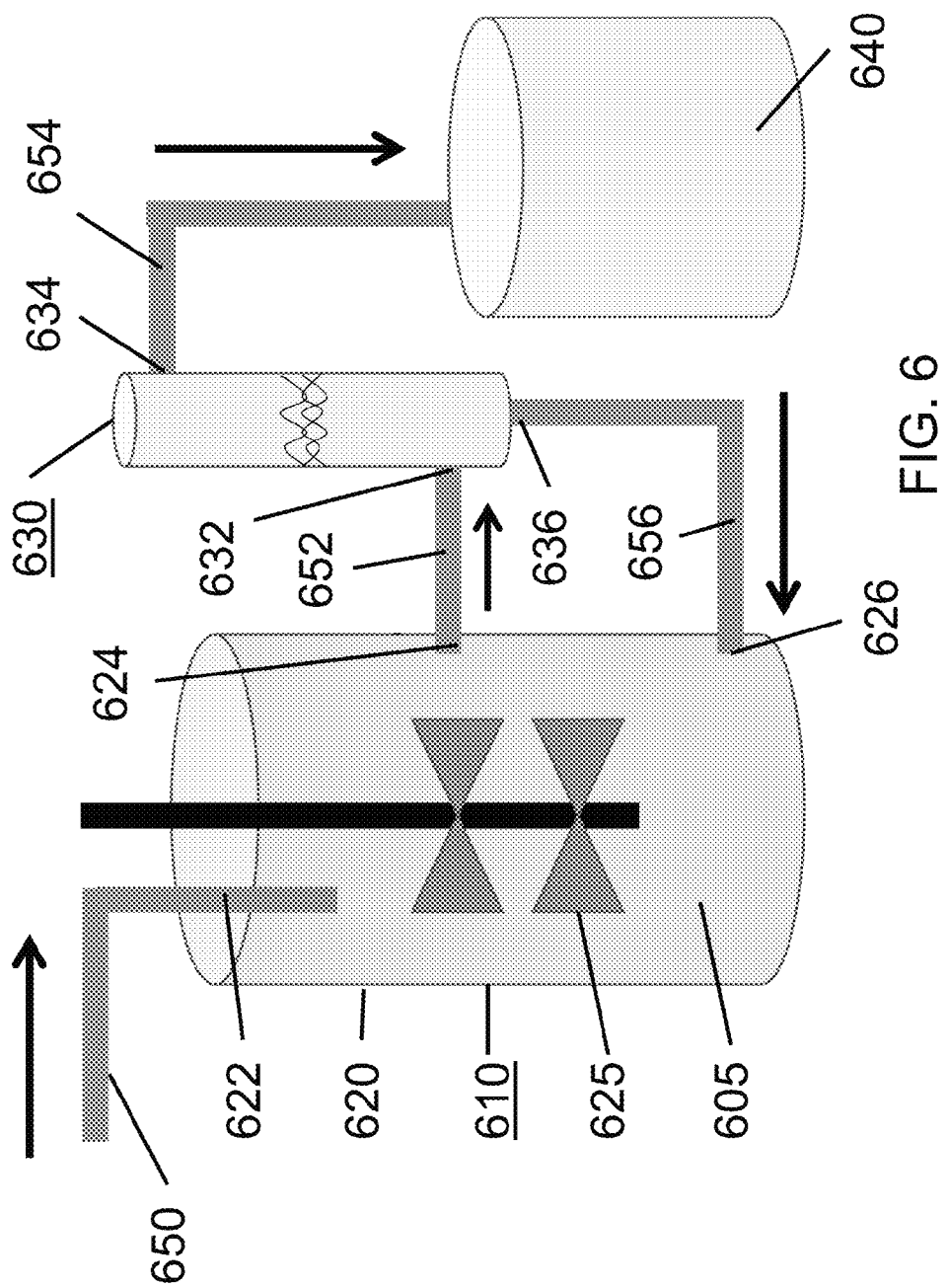
FIG. 6 is a schematic view illustrating a perfusion bioreactor coupled with an acoustic perfusion device of the present disclosure, and a recycle path.

Turning now to FIG. 6, a processing system is shown including an associated bioreactor 610 and an acoustic perfusion device 630 of the present disclosure. The system is set up for use as a perfusion bioreactor. The bioreactor 610 includes a reaction vessel 620 having a feed inlet 622, an outlet 624, and a recycle inlet 626. Fresh media is added into the feed inlet 622 by an addition pipe 650. Some reactors will also include an outlet or bleed port (not shown here) to remove or "bleed" cells in order to maintain a constant cell density within a reactor. The contents of the reaction vessel (reference numeral 605) are mixed with an agitator 625. The desired product (e.g., recombinant proteins) is continuously produced by cells located within the vessel 620, and are present in the media of the bioreactor. The product and the cells in the perfusion bioreactor are drawn from the reaction vessel through pipe 652, and enter the acoustic perfusion device 630 through inlet port 632. Therein, a portion of the desired product is separated from the cells. The desired product can be drawn off through a first collection port 634 (which is a product recovery port) and pipe 654 into a containment vessel 640, or in the case of a truly continuous production system, some other downstream purification process. The cells are returned to the perfusion bioreactor after separation, passing from outlet port 636 (which is a fluid recycle port) of the acoustic perfusion device through pipe 656 to recycle inlet 626 of the reaction vessel, which form a recycle path. The multi-dimensional standing wave(s) of the acoustic perfusion device are used to create a separation barrier between the fluid cell of the device and the collection port, so that a highly reduced number of biological cells are collected in collection port 634.

Figure 7:
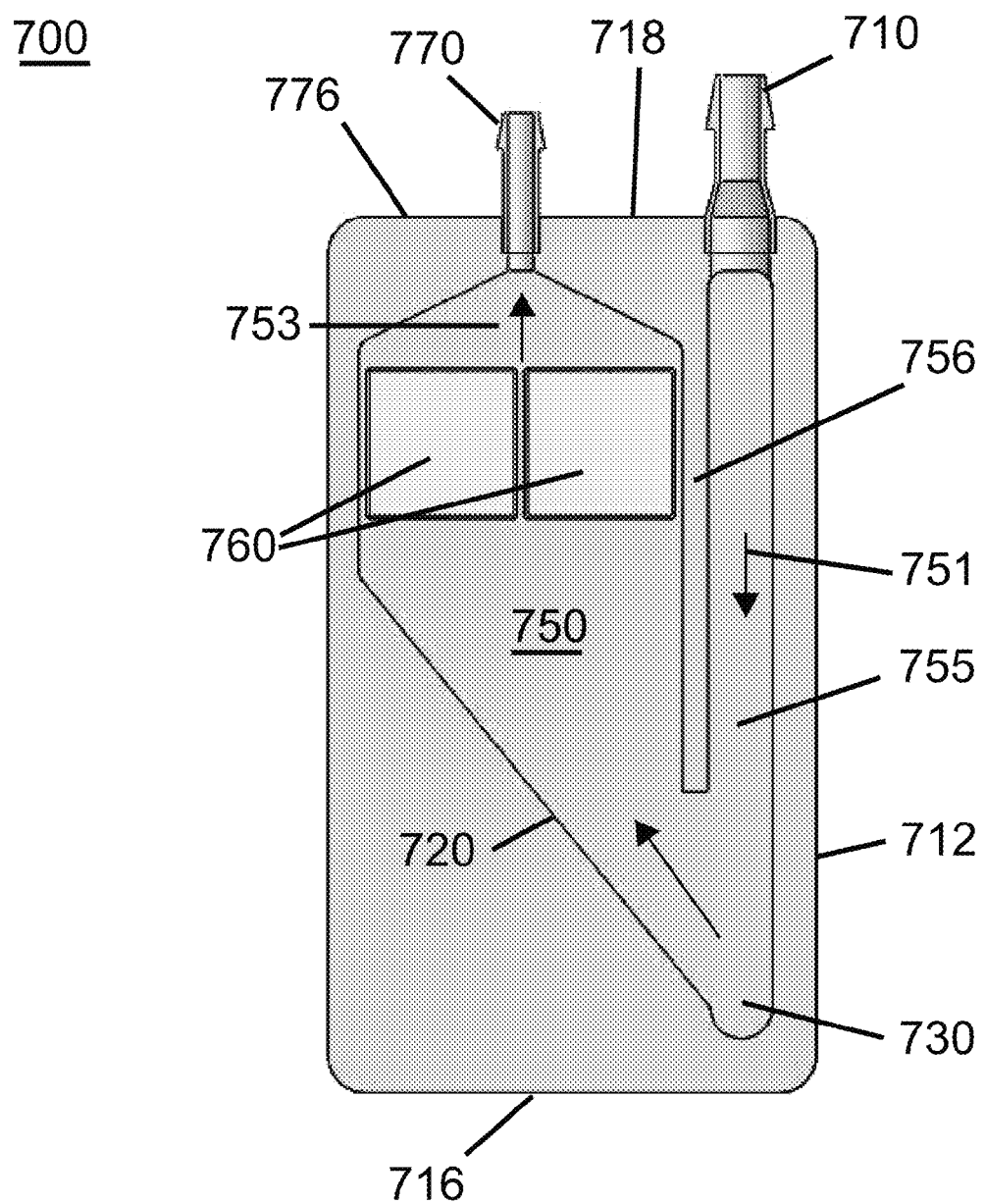
FIG. 7 is a front cross-sectional view of a third exemplary embodiment of an acoustic perfusion device of the present disclosure.
Figure 8:
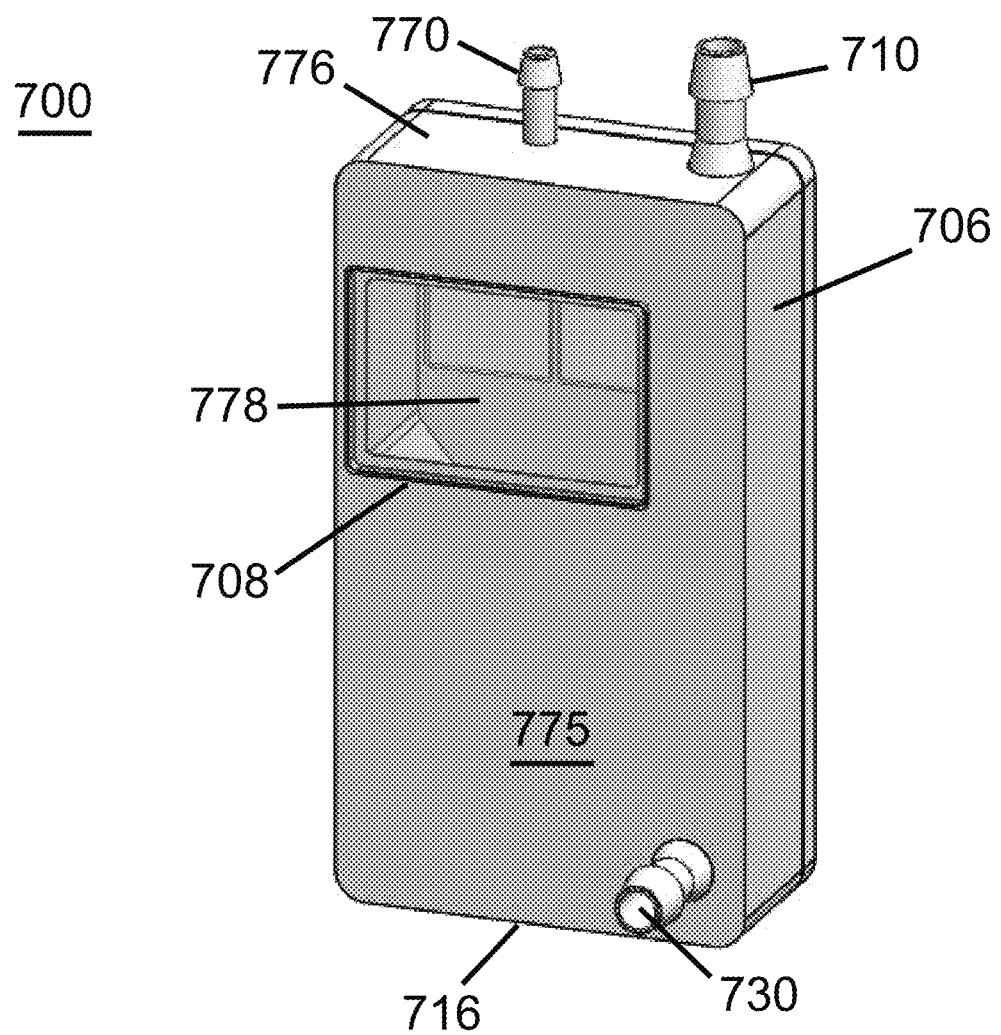
FIG. 8 is an exterior perspective view of the acoustic perfusion device of FIG. 7.

FIG. 7 and FIG. 8 are views of another exemplary embodiment of an acoustic perfusion device. FIG. 7 is a front cross-sectional view, and FIG. 8 is an exterior perspective view. Notably, this embodiment is specifically designed such that it can be fabricated with clean machining techniques, using Class VI materials (medical device grade HDPE, for example), or even as single or welded injection molded part. In this manner, this embodiment is an example of a single-use device, which is gamma-stable. The devices are flushed to remove bioburden and then gamma-irradiated (generally from 25-40 kGy) to sterilize any potential contamination that could destroy a healthy cell culture, such as that present in a perfusion bioreactor.

Referring first to FIG. 7, in this device 700, the inlet port 710 and the collection port 770 are both located at the top end 718 of the device, or on the top wall 776 of the device. The outlet port 730 is located at a bottom end 716 of the device. Here, the inlet port 710 and the outlet port 730 are both on a first side 712 of the device. The inlet flow path 751 is in the form of a channel 755 that runs from the inlet port downwards towards the bottom end and past the outlet port, the channel being separated from the acoustic chamber 750 (here, the separation occurring by an internal wall 756). Fluid will flow downwards in the channel, then rise upwards into the acoustic chamber 750. The bottom wall 720 of the acoustic chamber is a sloped planar surface that slopes down towards the outlet port 730. The location of the ultrasonic transducers 760 are shown here as two squares, between the top end and the bottom end of the device. The collection flow path 753 is located above the transducers.

Referring now to FIG. 8, the device 700 is shown as being formed within a three-dimensional rectangular housing 706. It can be seen that the outlet port 730 at the bottom end 716 of the device is located on a front wall 775. Again, the collection port 770 and the inlet port 710 are located on a top wall 776. A viewing window 708 made of a transparent material is present in the front wall. Through that viewing window, it can be seen that the ultrasonic transducers are mounted in the rear wall 778 of the device housing. The viewing window acts as a reflector to generate the multi-dimensional acoustic standing waves.

Figure 9:
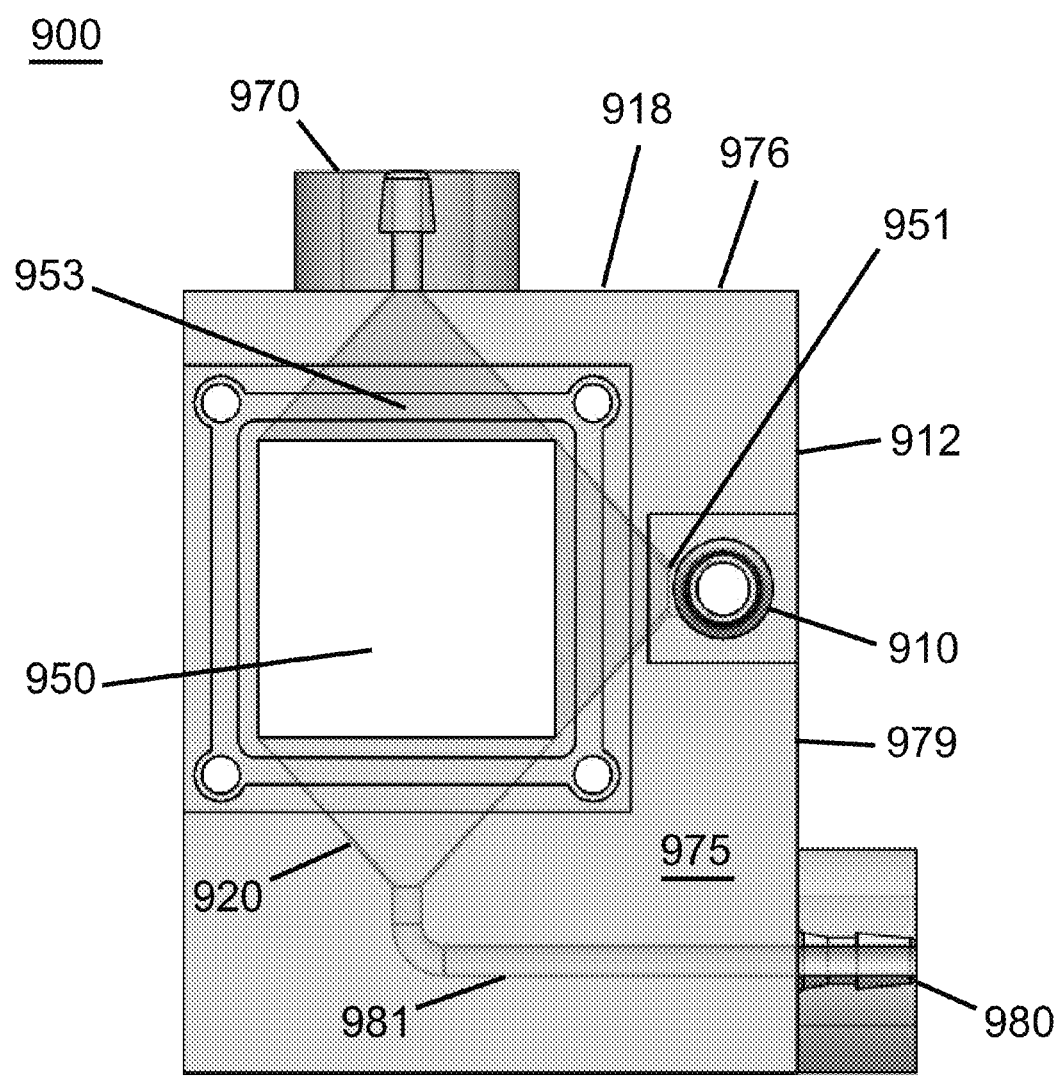
FIG. 9 is a front cross-sectional view of a fourth exemplary embodiment of an acoustic perfusion device of the present disclosure.
Figure 10:
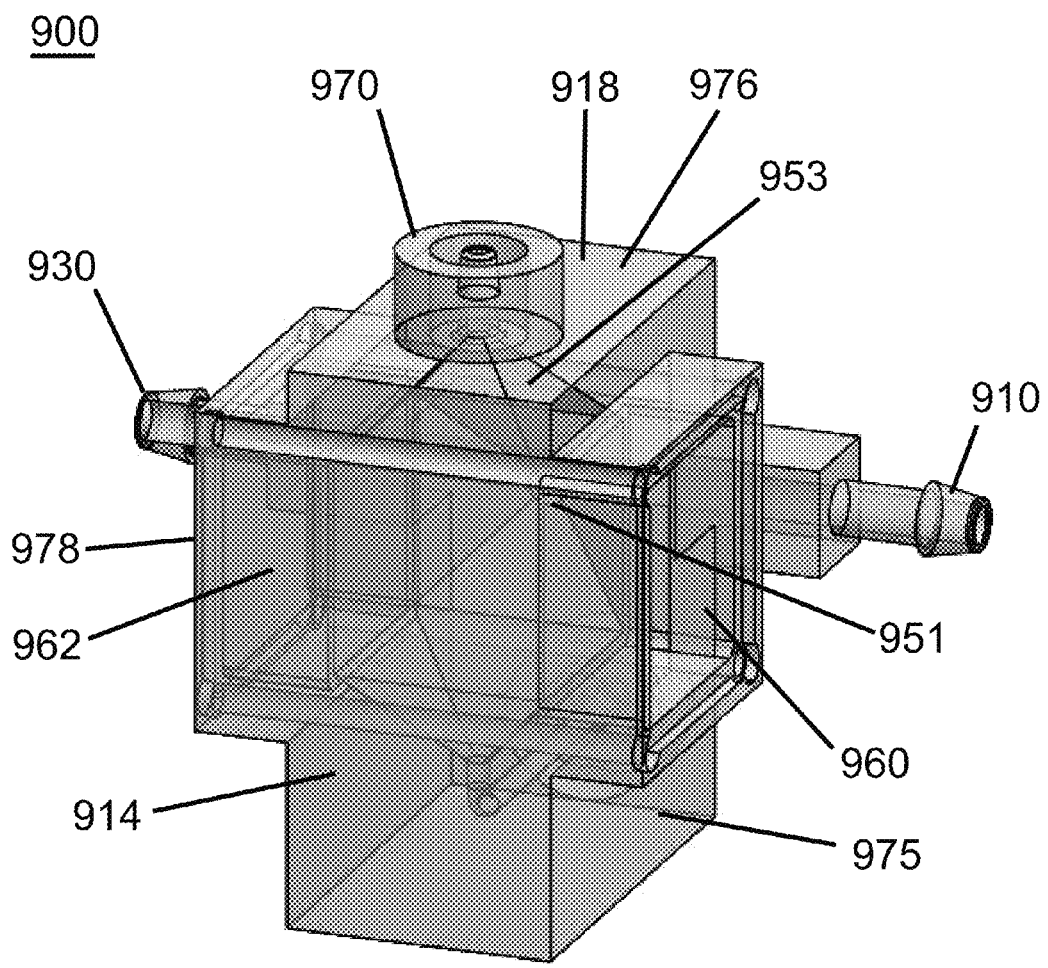
FIG. 10 is a perspective view of the acoustic perfusion device of FIG. 9.

FIG. 9 and FIG. 10 are views of yet another exemplary embodiment of an acoustic perfusion device. FIG. 9 is a front cross-sectional view, and FIG. 10 is a perspective view.

Referring first to FIG. 9, in this device 900, there is an inlet port 910 present on a front side 975 of the device along the first side 912 of the device. An outlet port 930 (best seen in FIG. 10) is located directly opposite and at the same height as the inlet port 910, and is also located on first side 912. In this embodiment, there is a main fluid stream that flows almost directly from the inlet port 910 to the outlet port 930, and the inlet flow path 951 diverts only a small side flow into the acoustic chamber 950 from the first side 912 of the device. The collection port 970 is located at the top end 918 of the device, or on the top wall 976 of the device. A secondary outlet port 980 is located on the first side 912 of the device as well, extending from first side wall 979, and located below the inlet port 910, and can act as a bleed port. The bottom wall 920 of the acoustic chamber is shaped in a pyramid-like fashion to taper downwards to a vertex. A drain line 981 runs from the bottom of the acoustic chamber 950 to the secondary outlet port 980. It is contemplated that here, the secondary outlet port can be used to capture a small flow of highly concentrated cells, which can either be discarded (cell bleed) or can also be returned back to the bioreactor.

Referring now to FIG. 10, the front wall 975 of the device has a rectangular space 960, and the rear wall 978 of the device has a rectangular space 962. It is contemplated that one transducer and one reflector can be placed in these two rectangular spaces 960/962 in either orientation, or that two transducers could be placed in the two rectangular spaces. The inlet port 910 and outlet port 930 are both visible in this view. The inlet port 910 is located on the front side of the device, and the outlet port 930 is located on the rear side of the device (though this could be reversed if desired). The clarification flow path 953 is located above the transducers. Although not depicted here, a mounting piece similar to that in FIG. 4 could be attached to the second side 914 of the device.

Figure 11:
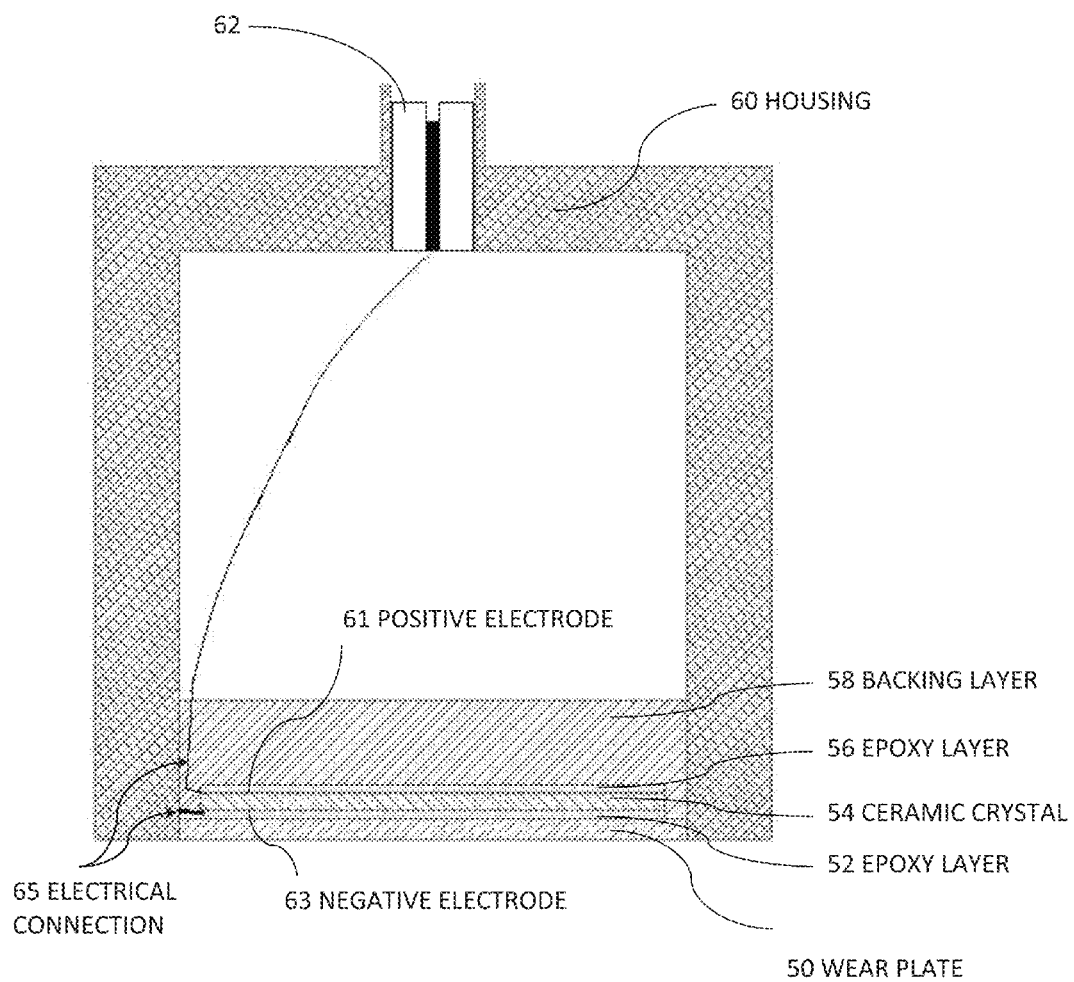
FIG. 11 is a cross-sectional diagram of a conventional ultrasonic transducer.

It may be helpful now to describe the ultrasonic transducer(s) used in the acoustic filtering device in more detail. FIG. 11 is a cross-sectional diagram of a conventional ultrasonic transducer. This transducer has a wear plate 50 at a bottom end, epoxy layer 52, ceramic piezoelectric element 54 (made of, e.g. Lead Zirconate Titanate (PZT)), an epoxy layer 56, and a backing layer 58. On either side of the ceramic piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. The housing is used as the ground electrode. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation of particular vibrational eigen-modes of the piezoelectric element. Wear plates are usually designed as impedance transformers to better match the characteristic impedance of the medium into which the transducer radiates.

Figure 12:
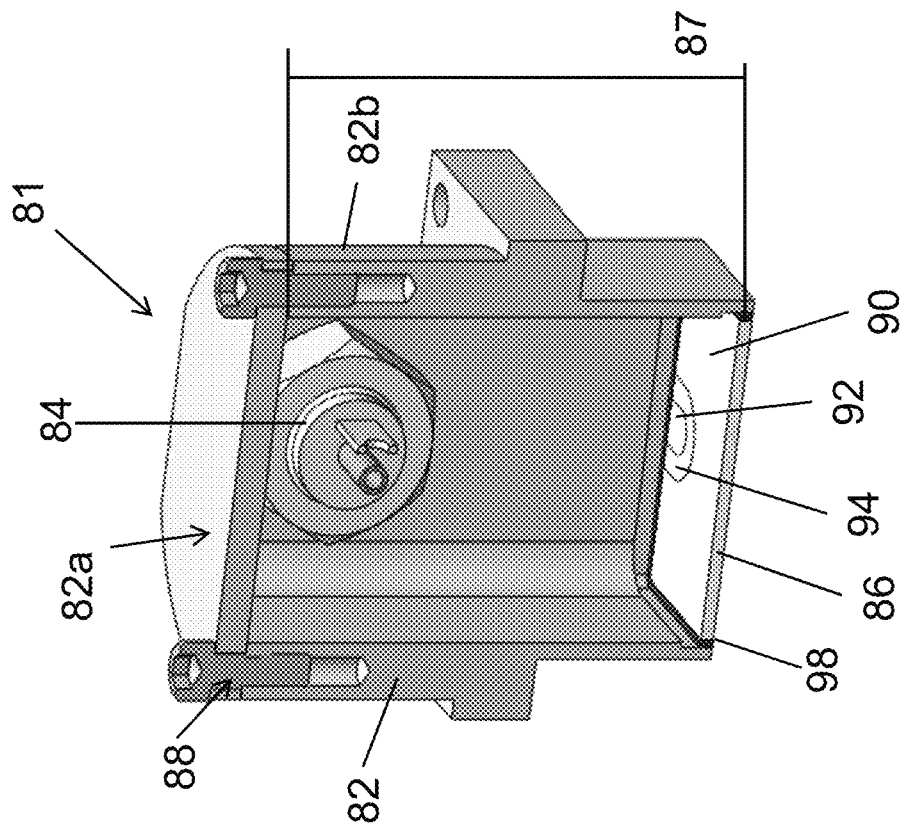
FIG. 12 is a cross-sectional diagram of an ultrasonic transducer of the present disclosure. An air gap is present within the transducer, and no backing layer or wear plate are present.

FIG. 12 is a cross-sectional view of an ultrasonic transducer 81 of the present disclosure, which is used in the acoustic filtering device of the present disclosure. Transducer 81 is shaped as a square, and has an aluminum housing 82. The aluminum housing has a top end and a bottom end. The transducer housing may also be composed of plastics, such as medical grade HDPE or other metals. The piezoelectric element is a mass of perovskite ceramic, each consisting of a small, tetravalent metal ion, usually titanium or zirconium, in a lattice of larger, divalent metal ions, usually lead or barium, and $O^{2-}$ ions. As an example, a PZT (lead zirconate titanate) piezoelectric element 86 defines the bottom end of the transducer, and is exposed from the exterior of the bottom end of the housing. The piezoelectric element is supported on its perimeter by a small elastic layer 98, e.g. epoxy, silicone or similar material, located between the piezoelectric element and the housing. Put another way, no wear plate or backing material is present. However, in some embodiments, there is a layer of plastic or other material separating the piezoelectric element from the fluid in which the acoustic standing wave is being generated. The piezoelectric element/crystal has an exterior surface (which is exposed) and an interior surface as well.

Figure 13:
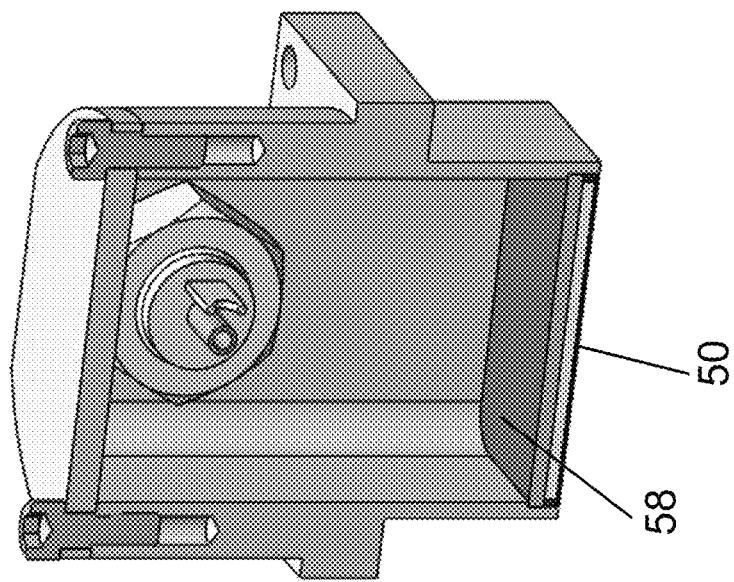
FIG. 13 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT piezoelectric element 86 is connected to a positive electrode 90 and a negative electrode 92, which are separated by an insulating material 94. The electrodes can be made from any conductive material, such as silver or nickel. Electrical power is provided to the PZT piezoelectric element 86 through the electrodes on the piezoelectric element. Note that the piezoelectric element 86 has no backing layer or epoxy layer. Put another way, there is an interior volume or an air gap 87 in the transducer between aluminum top plate 82a and the piezoelectric element 86 (i.e. the air gap is completely empty). A minimal backing 58 and/or wear plate 50 may be provided in some embodiments, as seen in FIG. 13.

The transducer design can affect performance of the system. A typical transducer is a layered structure with the ceramic piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes with a high Q-factor, or in a combination of several eigenmodes. The vibrating ceramic piezoelectric element/disk is directly exposed to the fluid flowing through the fluid cell.

Removing the backing (e.g. making the piezoelectric element air backed) also permits the ceramic piezoelectric element to vibrate at higher order modes of vibration with little damping (e.g. higher order modal displacement). In a transducer having a piezoelectric element with a backing, the piezoelectric element vibrates with a more uniform displacement, like a piston. Removing the backing allows the piezoelectric element to vibrate in a non-uniform displacement mode. The higher order the mode shape of the piezoelectric element, the more nodal lines the piezoelectric element has. The higher order modal displacement of the piezoelectric element creates more trapping lines, although the correlation of trapping line to node is not necessarily one to one, and driving the piezoelectric element at a higher frequency will not necessarily produce more trapping lines.

It is contemplated that, in some embodiments of the acoustic filtering device of the present disclosure, the piezoelectric element may have a backing that minimally affects the Q-factor of the piezoelectric element (e.g. less than 5%). The backing may be made of a substantially acoustically transparent material such as balsa wood, foam, or cork which allows the piezoelectric element to vibrate in a higher order mode shape and maintains a high Q-factor while still providing some mechanical support for the piezoelectric element. The backing layer may be a solid, or may be a lattice having holes through the layer, such that the lattice follows the nodes of the vibrating piezoelectric element in a particular higher order vibration mode, providing support at node locations while allowing the rest of the piezoelectric element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments of the transducer(s) may have wear plates or a wear surface to prevent the PZT, which contains lead, contacting the host fluid. This may be desirable in, for example, biological applications such as separating blood, biopharmaceutical perfusion, or fed-batch filtration of mammalian cells. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

In some embodiments, for applications such as oil/water emulsion splitting and others such as perfusion, the ultrasonic transducer has a nominal 2 MHz resonance frequency. Each transducer can consume about 28 W of power for droplet trapping at a flow rate of 3 GPM. This translates to an energy cost of 0.25 kW hr/m$^3$. This is an indication of the very low cost of energy of this technology. Desirably, each transducer is powered and controlled by its own amplifier. In other embodiments, the ultrasonic transducer uses a square piezoelectric element, for example with 1"×1" dimensions. Alternatively, the ultrasonic transducer can use a rectangular piezoelectric element, for example with 1"×2.5" dimensions. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired multi-dimensional acoustic standing wave patterns.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more trapping locations for the cells/biomolecules. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

To investigate the effect of the transducer displacement profile on acoustic trapping force and separation efficiencies, an experiment was repeated ten times using a 1"×1" square transducer, with all conditions identical except for the excitation frequency. Ten consecutive acoustic resonance frequencies, indicated by circled numbers 1-9 and letter A on FIG. 14, were used as excitation frequencies. The conditions were experiment duration of 30 min, a 1000 ppm oil concentration of approximately 5-micron SAE-30 oil droplets, a flow rate of 500 ml/min, and an applied power of 20 W. Oil droplets were used because oil is less dense than water, and can be separated from water using acoustophoresis.

Figure 14:
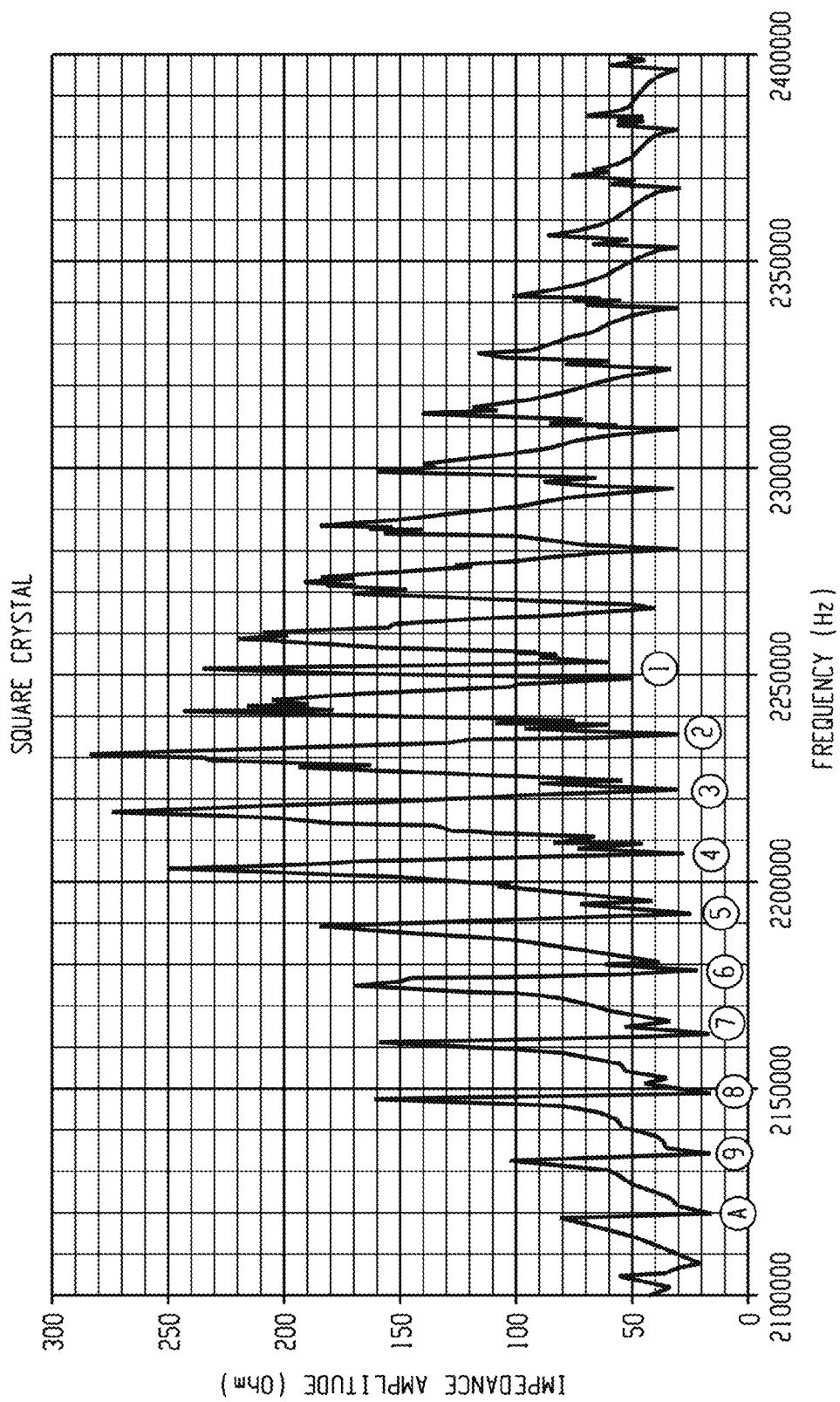
FIG. 14 is a graph of electrical impedance amplitude versus frequency for a square transducer driven at different frequencies.

FIG. 14 shows the measured electrical impedance amplitude of a square transducer as a function of frequency in the vicinity of the 2.2 MHz transducer resonance. The minima in the transducer electrical impedance correspond to acoustic resonances of the water column and represent potential frequencies for operation. Additional resonances exist at other frequencies where multi-dimensional standing waves are excited. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

Figure 15:
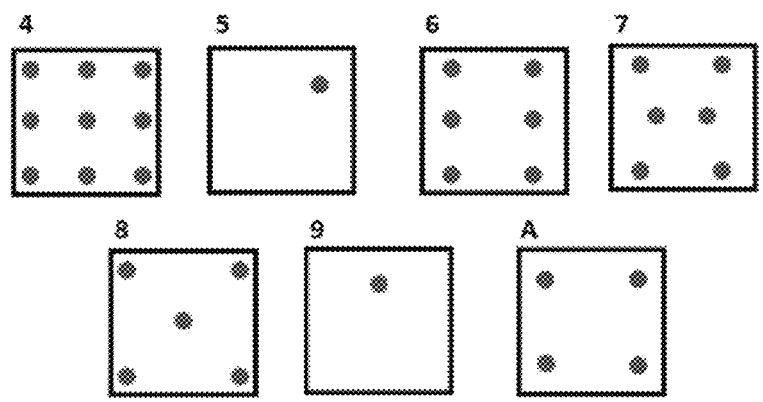
FIG. 15 illustrates the trapping line configurations for seven of the resonance frequencies (minima of electrical impedance amplitudes) of FIG. 14 from the direction orthogonal to fluid flow.

As the oil-water emulsion passed by the transducer, the trapping lines of oil droplets were observed and characterized. The characterization involved the observation and pattern of the number of trapping lines across the fluid channel, as shown in FIG. 15, for seven of the ten resonance frequencies identified in FIG. 14. Different displacement profiles of the transducer can produce different (more) trapping lines in the standing waves, with more gradients in displacement profile generally creating higher trapping forces and more trapping lines.

Figure 16:
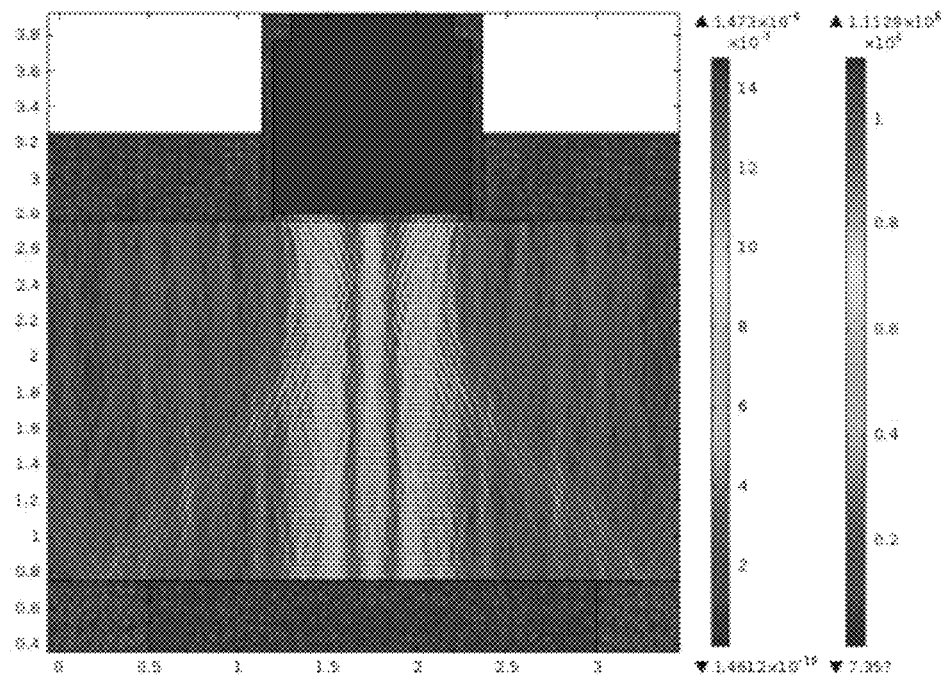
FIG. 16 is a computer simulation of the acoustic pressure amplitude (right-hand scale in Pa) and transducer out of plane displacement (left-hand scale in meters). The text at the top of the left-hand scale reads "$\times 10^{-7}$". The text at the top of the left-hand scale by the upward-pointing triangle reads "$1.473 \times 10^{-6}$". The text at the bottom of the left-hand scale by the downward-pointing triangle reads "$1.4612 \times 10^{-10}$". The text at the top of the right-hand scale reads "$\times 10^{6}$". The text at the top of the right-hand scale by the upward-pointing triangle reads "$1.1129 \times 10^{6}$". The text at the bottom of the right-hand scale by the downward-pointing triangle reads "7.357". The triangles show the maximum and minimum values depicted in this figure for the given scale. The horizontal axis is the location within the chamber along the X-axis, in inches, and the vertical axis is the location within the chamber along the Y-axis, in inches.

FIG. 16 is a numerical model showing a pressure field that matches the 9 trapping line pattern. The numerical model is a two-dimensional model; and therefore only three trapping lines are observed. Two more sets of three trapping lines exist in the third dimension perpendicular to the plane of the page.

The lateral force of the acoustic radiation force generated by the transducer can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage. The transducer is typically a thin piezoelectric plate, with electric field in the z-axis and primary displacement in the z-axis. The transducer is typically coupled on one side by air (i.e., the air gap within the transducer) and on the other side by the fluid medium of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Figure 17:
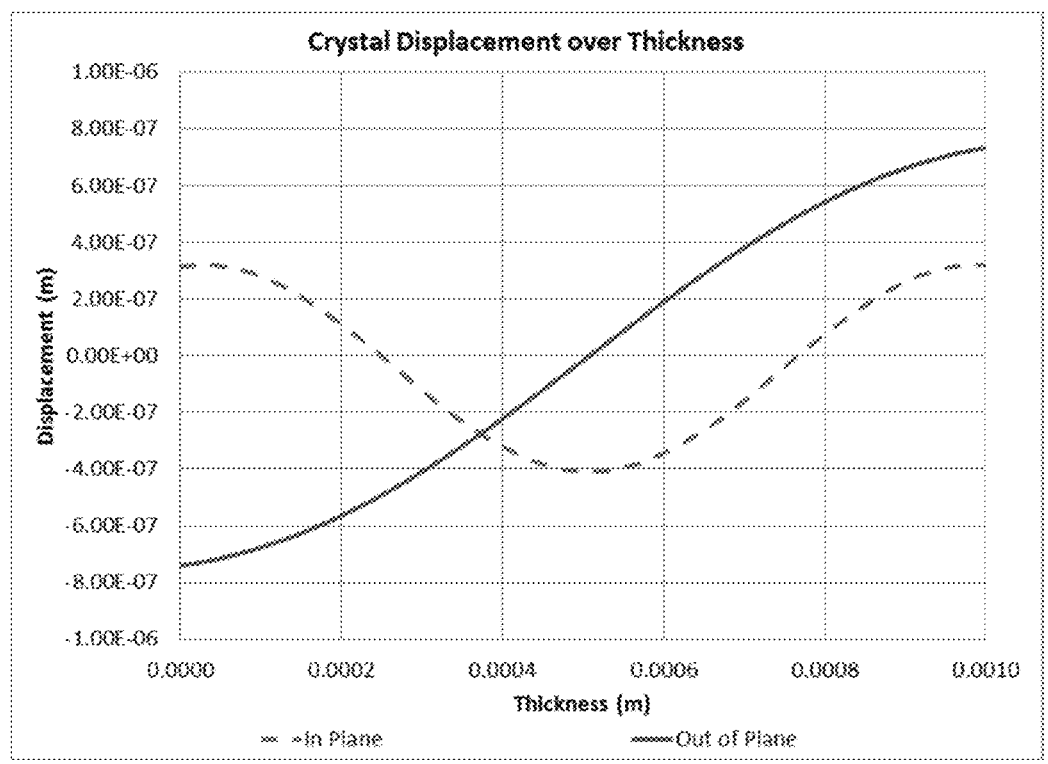
FIG. 17 shows the In-Plane and Out-of-Plane displacement of a crystal where composite waves are present.

FIG. 17 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. In general, a (m,n) mode is a displacement mode of the transducer in which there are m undulations in transducer displacement in the width direction and n undulations in the length direction, and with the thickness variation as described in FIG. 17. The maximum number of m and n is a function of the dimension of the crystal and the frequency of excitation. Additional three-dimensional modes exist that are not of the form (m,n).

The transducers are driven so that the piezoelectric element vibrates in higher order modes of the general formula (m, n), where m and n are independently 1 or greater. Generally, the transducers will vibrate in higher order modes than (2,2). Higher order modes will produce more nodes and antinodes, result in three-dimensional standing waves in the water layer, characterized by strong gradients in the acoustic field in all directions, not only in the direction of the standing waves, but also in the lateral directions. As a consequence, the acoustic gradients result in stronger trapping forces in the lateral direction.

In embodiments, the voltage signal driving the transducer can have a sinusoidal, square, sawtooth, pulsed, or triangle waveform; and have a frequency of 500 kHz to 10 MHz. The voltage signal can be driven with pulse width modulation, which produces any desired waveform. The voltage signal can also have amplitude or frequency modulation start/stop capability to eliminate streaming.

The transducers are used to create a pressure field that generates acoustic radiation forces of the same order of magnitude both orthogonal to the standing wave direction and in the standing wave direction. When the forces are roughly the same order of magnitude, particles of size 0.1 microns to 300 microns will be moved more effectively towards "trapping lines", so that the particles will not pass through the pressure field and continue to exit through the collection ports of the filtering device. Instead, the particles will remain within the acoustic chamber to be recycled back to the bioreactor.

The following examples are provided to illustrate the devices, components, and methods of the present disclosure. The examples are merely illustrative and are not intended to limit the disclosure to the materials, conditions, or process parameters set forth therein.

EXAMPLES

Example 1

Figure 18:
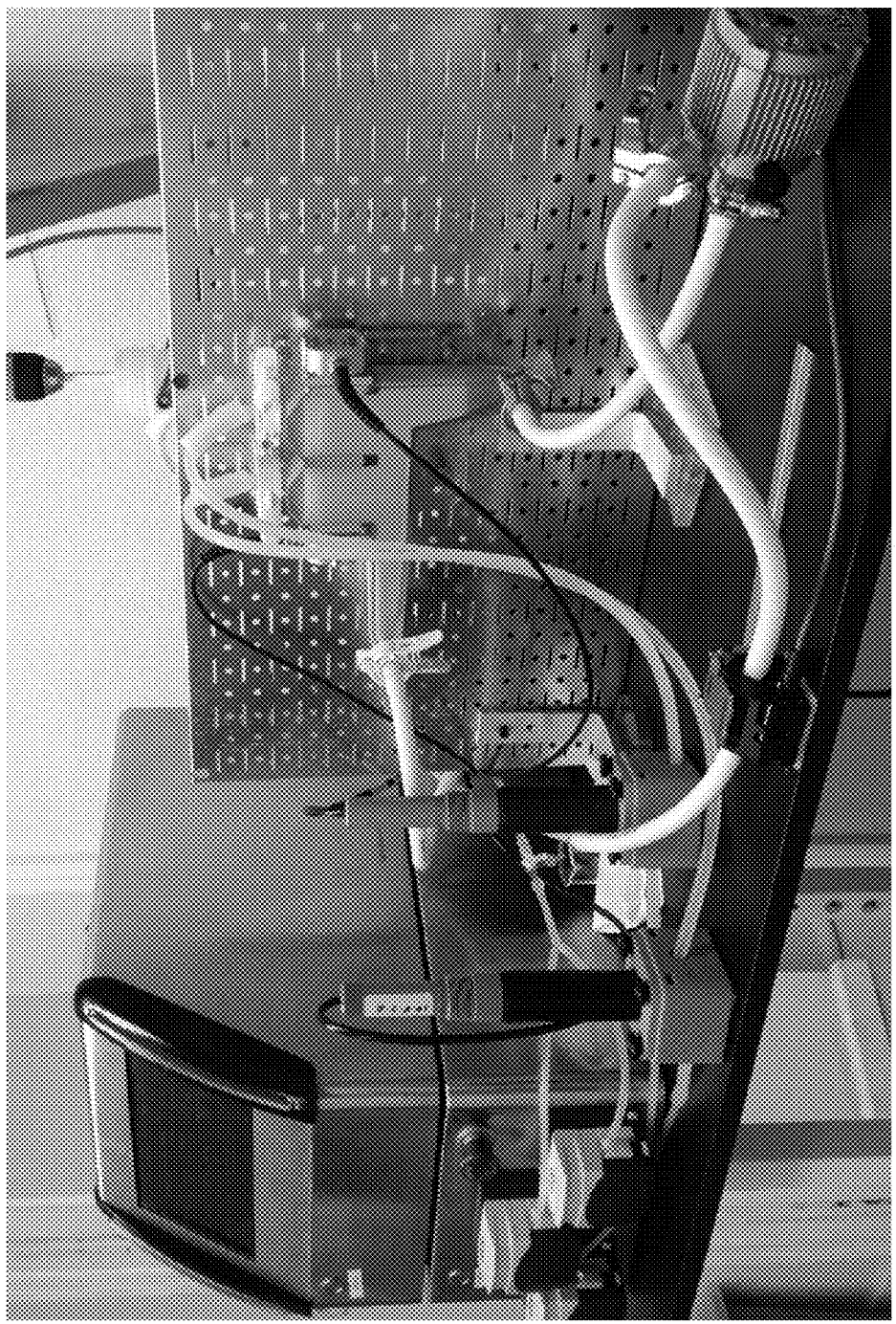
FIG. 18 is a view of a first acoustic perfusion device of the present disclosure fluidly connected to an associated bioreactor, showing a plurality of hoses fluidly connecting the various ports of the device to the associated bioreactor and an outflow pump fluidly connecting the outlet port of the device to the associated bioreactor.

FIG. 18 shows an experimental setup for an acoustic perfusion device as described in detail above. This acoustic perfusion device is very similar to that illustrated in FIG. 5, except the bottom wall is not curved, but rather runs horizontally from the first end and then angles directly to the outlet port. Tubes are connected to the inlet port, outlet port, and the two collection ports. A pump is also visibly fluidly connected to the outlet port.

Figure 19:
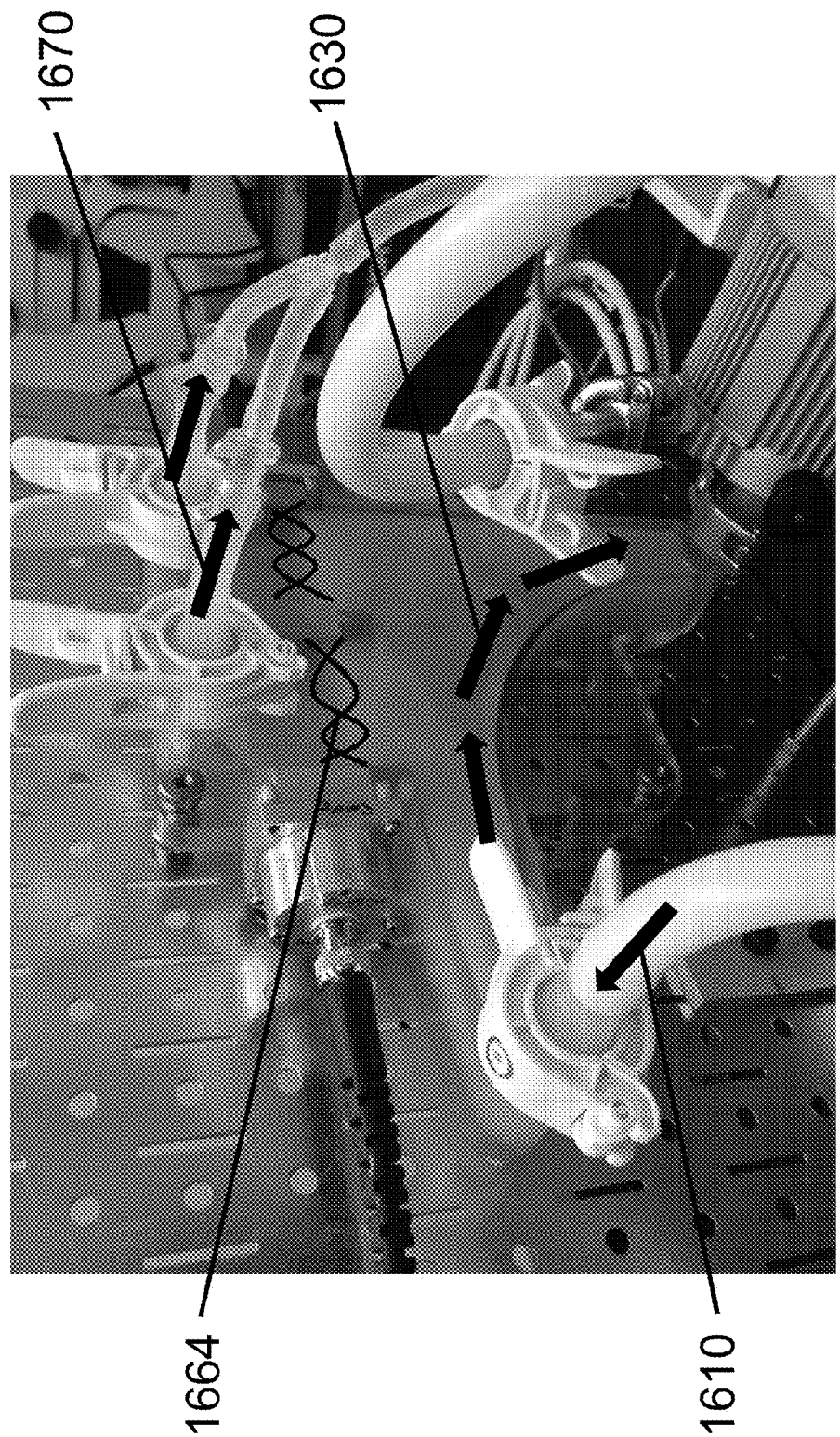
FIG. 19 is a view of another acoustic perfusion device of FIG. 5, showing a reflector in the acoustic chamber between first and second transducers. A fluid medium is also present in the device and arrows are shown indicating the direction of flow in addition to waves indicating the acoustic field between the reflector and first and second transducers.

FIG. 19 is a picture of another acoustic perfusion device of the present disclosure, similar to the embodiment shown in FIG. 5, having two ultrasonic transducers and a concave bottom wall leading from the inlet port to the outlet port at the bottom end of the device. A cell containing fluid medium is also present in the device. In this picture, acoustic standing waves are created in the collection zone between the reflector and first and second transducers as described above. The acoustic field generated thereby is indicated by waves and reference numeral 1664. The flow pattern of the fluid medium through the device from the inlet port to the outlet port is shown with an arrow (reference numeral 1610) indicating the direction of fluid flow into the device and arrows (reference numeral 1630) indicating the direction of fluid flow through the device towards the outlet port. Finally, the general flow pattern of the desired product out of the device through the first and second collection ports is shown with arrows (reference numeral 1670) indicating the direction of flow.

Acoustophoretic separation has been tested using the acoustic perfusion device of FIG. 19 and the methods of separation of the present disclosure on different lines of Chinese hamster ovary (CHO) cells. FIGS. 20-28 show various test results varying different parameters and measuring different values using a Beckman Coulter Cell Viability Analyzer.

The perfusion flow rates with the acoustic filtering device were from about 2 mL/min to about 10 mL/min, or the flow rates were about 1 VVD to about 5 VVD for a 2.7 L working volume bioreactor. The VVD refers to the "vessel volume per day", or how many times the volume of the bioreactor vessel is cycled through the acoustic filtering device in one day. The perfusion flow rate (Qp) was collected through the perfusion ports. In contrast, the feed flow rates (Qf) were from about 40 mL/min to about 200 mL/min.

The feed solution had a starting CHO cell density of $50\times10^6$ cells/mL. The reactor size was 2.7 L and the feed volume of the host fluid was 1.5 L. In total, a series of seven tests (T1-T7) were performed to study the effect of varying the VVD and flow split in a 2.7 L volume reactor. The parameters for the tests are shown in Table 1 below.

TABLE 1

System results for a 2.7 L reactor and feed volume of 1.5 L

| | Flow Split | Qp | | | |
|---|---|---|---|---|---|
| Qf | (Qp/Qf) | 1 VVD | 1.5 VVD | 2 VVD | 5.2 VVD |
| | 5.0% | T1 | T2 | T3 | T7 |
| | 2.5% | T4 | T5 | T6 | |

Figure 20:
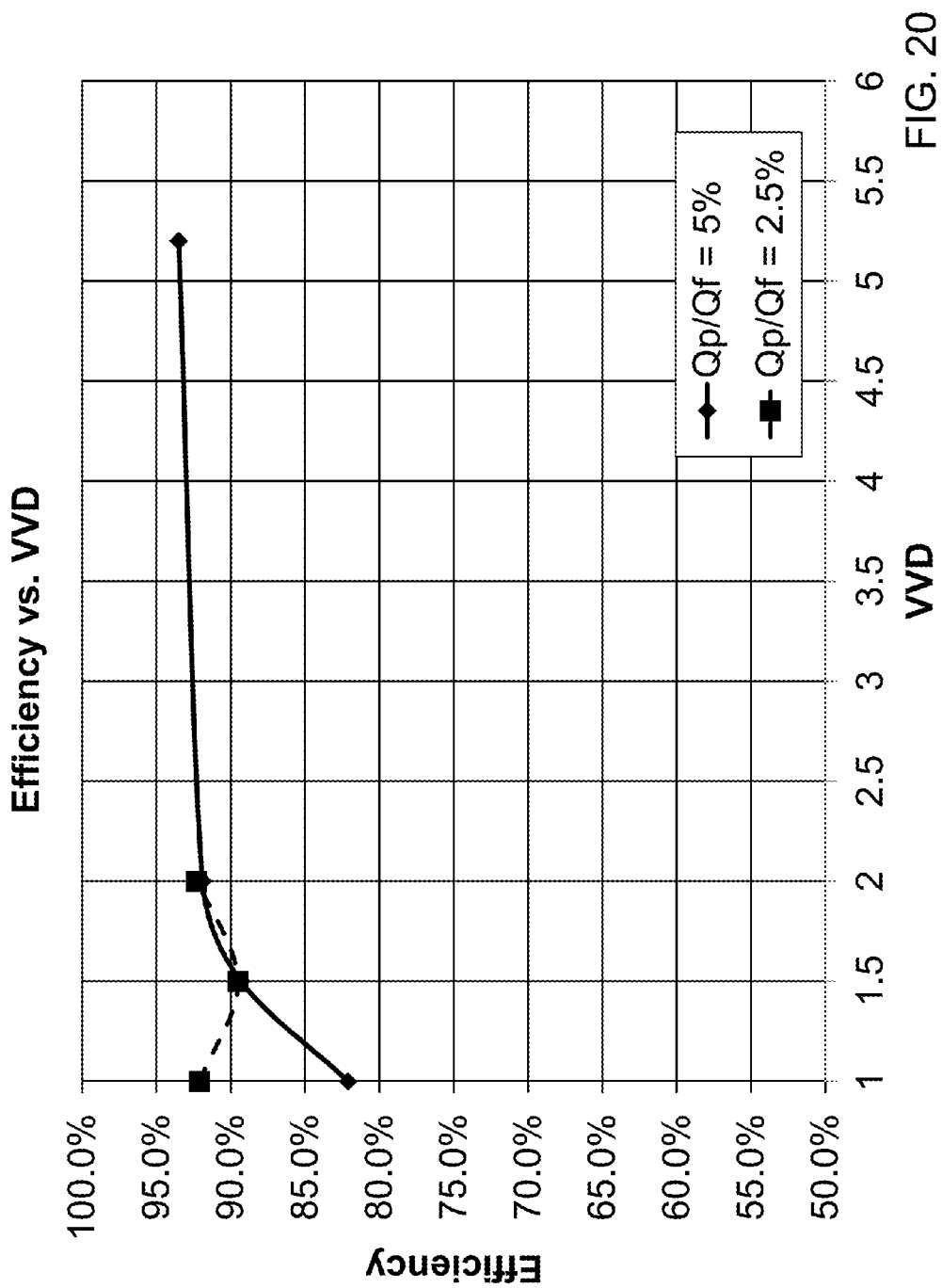
FIG. 20 is a graph showing the efficiency of removing cells from a fluid medium for one experiment at two different perfusate/feed rates.

The results included a cell clarification efficiency between 89-93% at a DC voltage of 45V, regardless of the flow rate as shown in FIG. 20. It is noted that the DC voltage for T1 was fixed at 60V, whereas for tests T2-T7 the DC voltage was reduced to a fixed amount of 45V. The transducer voltage amplitude is half of these values.

Figure 21:
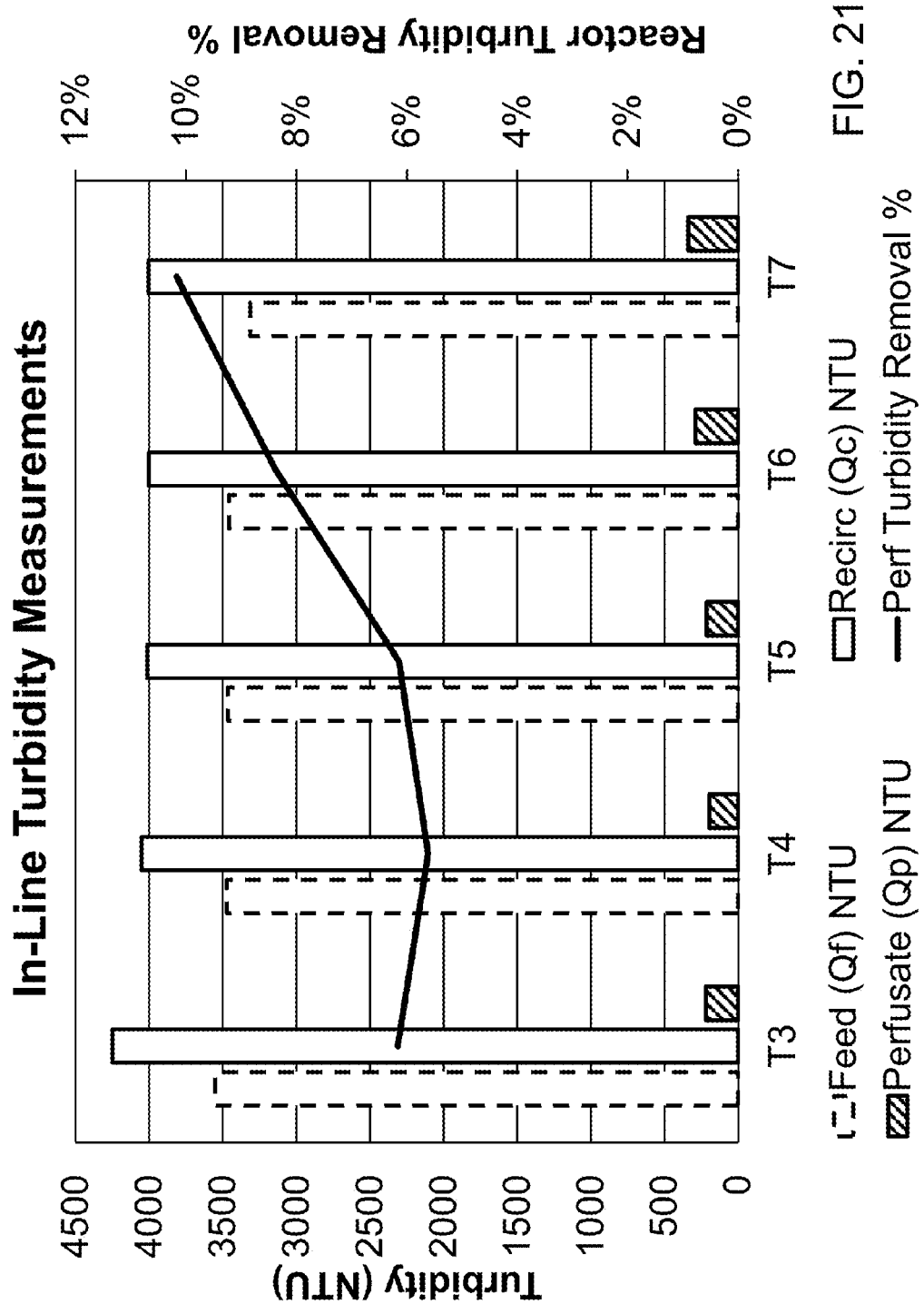
FIG. 21 is a graph showing the harvest flow (also referred to as the perfusate) turbidity reduction for an experiment

The results further included a perfusate turbidity reduction of 90-94% compared to the feed, as shown in FIG. 21. This figure shows the turbidity of the feed, the recirculated fluid (Qc), and the perfusate (Qp). The feed entered the inlet port, the recirculated fluid exited the outlet port and was recirculated, and the perfusate exited the perfusion port of the acoustic filtering device. It is noted that the turbidity measurements for tests T1 and T2 resulted in a hardware error, so only tests T3-T7 are displayed, which equated to a 6-10% turbidity in the perfusion stream relative to the feed stream, regardless of flow rate.

Figure 22:
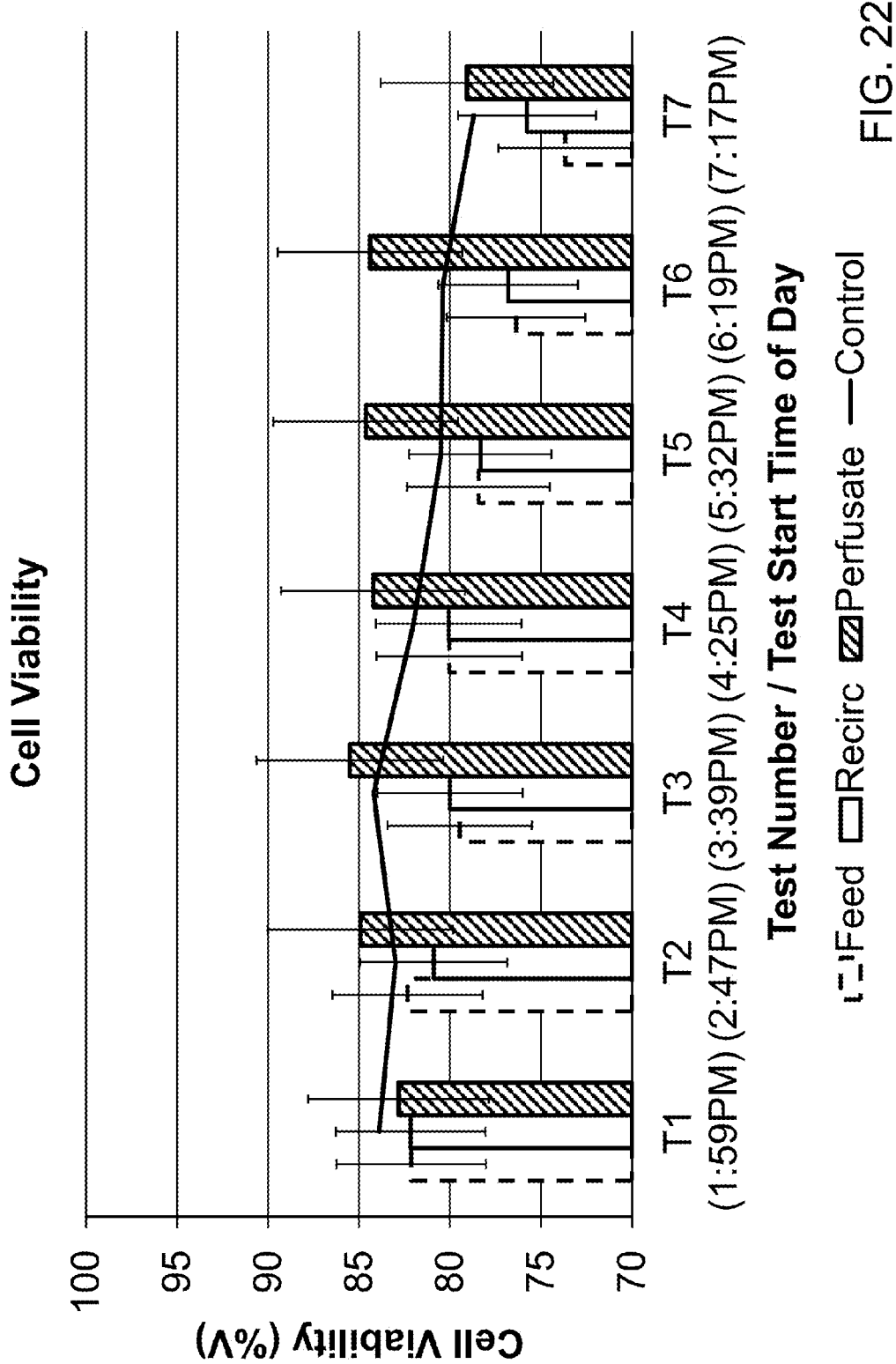
FIG. 22 is a graph showing the cell viability for varied flow rates for the experiment conducted for the graphs of FIGS. 20-21.

FIG. 22 was produced by a Beckman Coulter Cell Viability Analyzer and revealed a cell viability for each flow rate that was within the error of instrument (i.e., ±6%), with the control ranging from 79-84% over all tests.

Further testing was performed using a solution designated "CHO Line A". The solution had a starting cell density of $50\times10^6$ cells/mL, a turbidity of 2,400 NTU, and cell viability of roughly 80%. The solution was separated using a device of the present disclosure in a system having a reactor size of 2.7 L. The volume of the feed fluid was between 1.5 L and 2.0 L. The perfused flow rates were from 2 mL/min to 10 mL/min, or from 1 to 5 VVD. A series of six tests were performed to study the effect of varying the VVD and flow split on acoustic filtration performance for the 2.7 L volume reactor. The parameters for the tests are shown in Table 2 below.

TABLE 2

System results for a 2.7 L reactor and feed volume from 1.5 L-2.0 L

| T1 | | T2 | | T3 | |
|---|---|---|---|---|---|
| VVD | 1.5 | VVD | 2 | VVD | 1 |
| Flow Split | 5.00% | Flow Split | 5.00% | Flow Split | 2.50% |
| Perfused Flow (ml/min) | 2.8 | Perfused Flow (ml/min) | 3.8 | Perfused Flow (ml/min) | 1.9 |
| Feed Flow (ml/min) | 56 | Feed Flow (ml/min) | 75 | Feed Flow (ml/min) | 75 |

| T4 | | T5 | | T6 | |
|---|---|---|---|---|---|
| VVD | 1.5 | VVD | 2 | VVD | 5.2 |
| Flow Split | 2.50% | Flow Split | 2.50% | Flow Split | 5.00% |
| Perfused Flow (ml/min) | 2.8 | Perfused Flow (ml/min) | 3.8 | Perfused Flow (ml/min) | 10 |
| Feed Flow (ml/min) | 112.5 | Feed Flow (ml/min) | 150 | Feed Flow (ml/min) | 194.2 |

Figure 23:
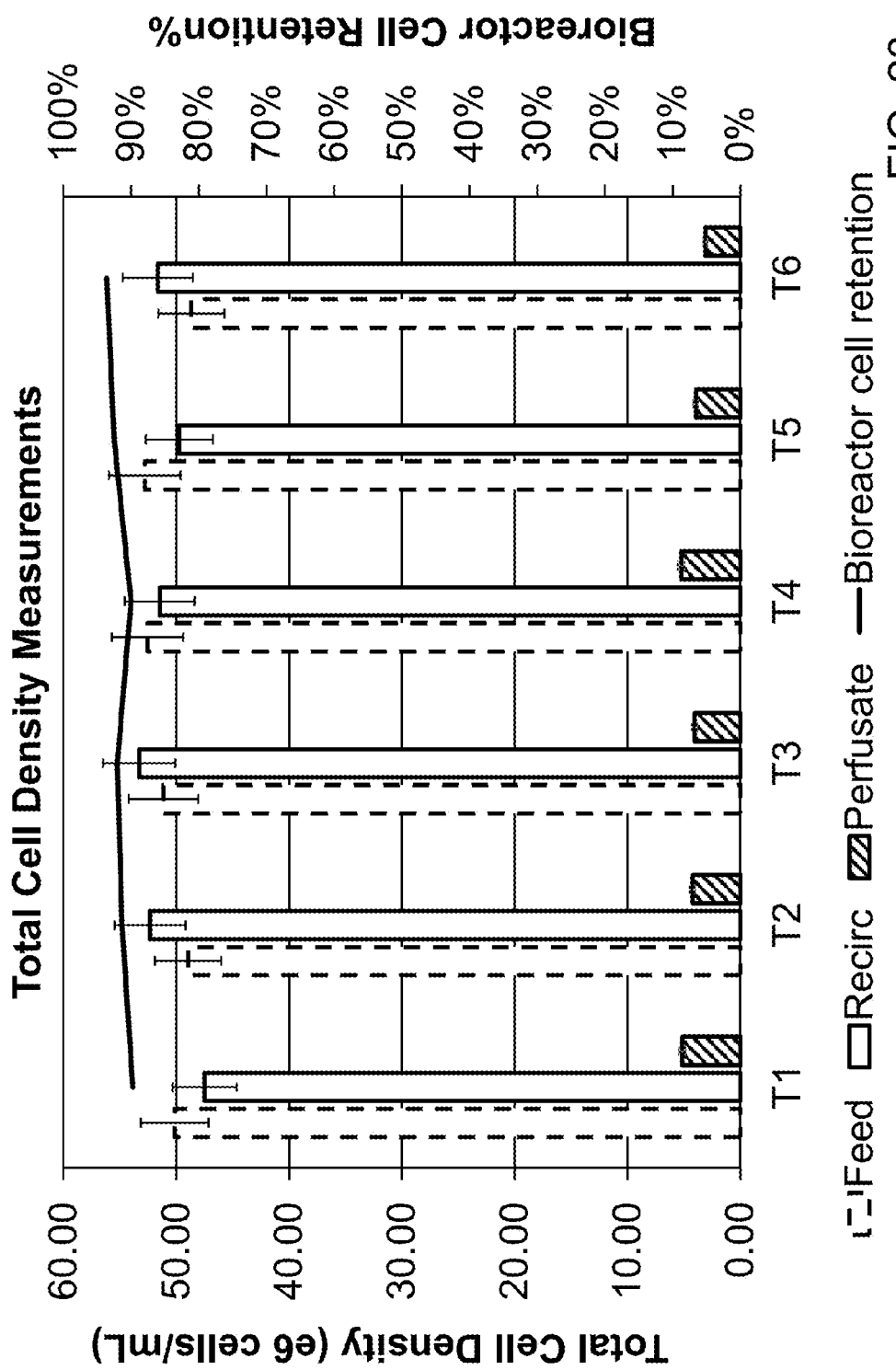
FIG. 23 is a graph showing the total cell density and cell retention for varied flow rates and flow methods for another experiment.
Figure 24:
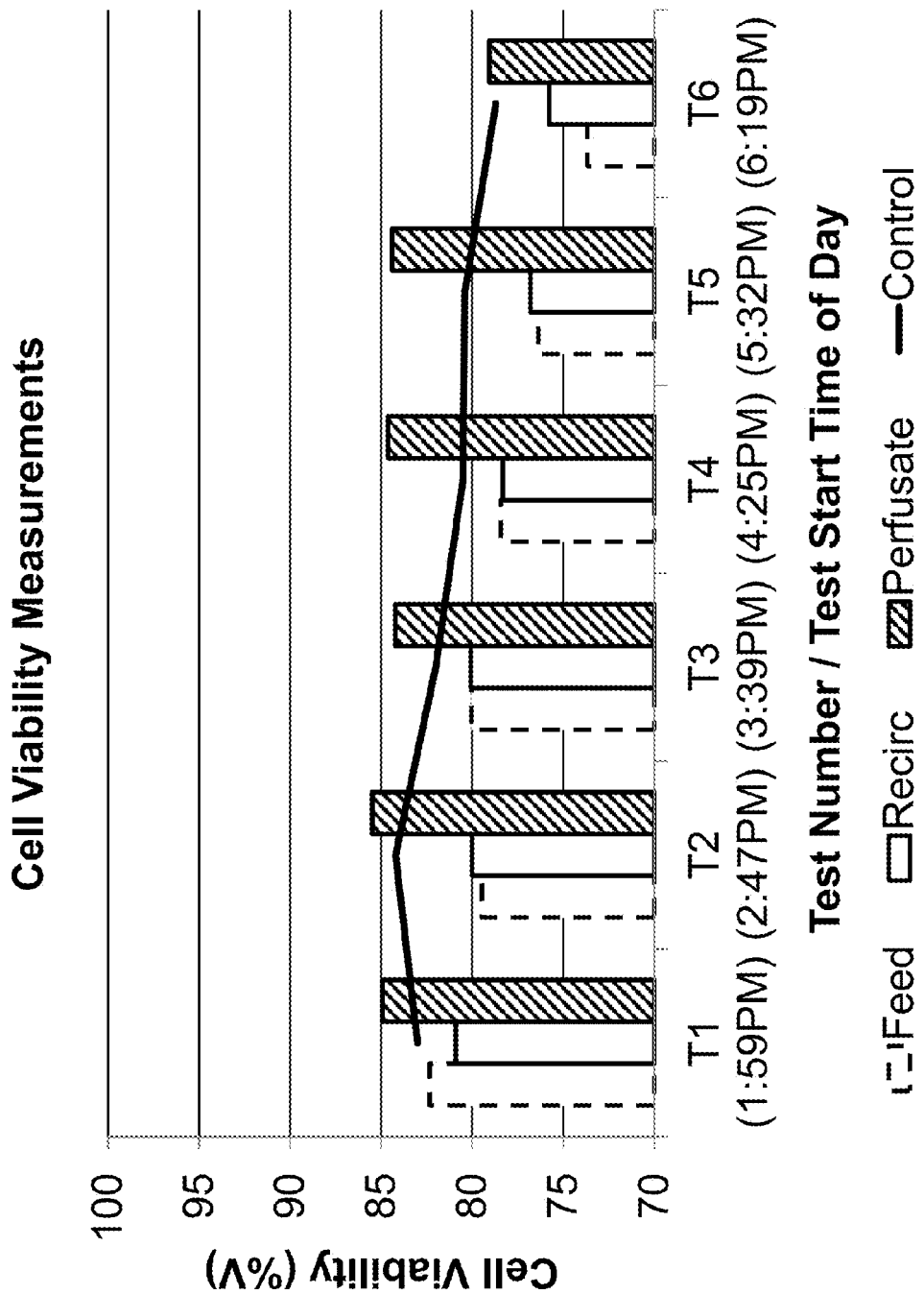
FIG. 24 is a graph showing the cell viability for varied flow rates for the experiment conducted for the graphs of FIG. 23.

FIG. 23 shows the measured total cell density of feed flow, recirculation flow, and perfused flow. The bioreactor cell retention for the tests shows an approximately 90% perfusion efficiency. FIG. 24 shows the measured cell viability for the tests, revealing no significant change in viability across the tests.

Next, additional testing was performed using a solution designated "CHO Line B". The solution had a starting cell density of $75 \times 10^6$ cells/mL, a turbidity of 2,300 NTU, and cell viability of roughly 80%. The solution was separated using a device of the present disclosure in a system having a reactor size of 2.7 L. Four tests were performed (T1-T4). Two of the tests (T1, T3) used a device having a single transducer. The other two tests (T2, T4) used a device having two transducers in series (such that the fluid ran through both standing waves). The parameters for the tests are shown in Table 3 below.

TABLE 3

System results for a 2.7 L reactor and feed volume from 1.5 L-2.0 L

| T1 | | T2 | |
|---|---|---|---|
| Transducers | 1 | Transducers | 2 |
| VVD | 1 | VVD | 1 |
| Perfused Flow (mL/min) | 1.9 | Perfused Flow (mL/min) | 1.9 |
| Feed Flow (mL/min) | 75 | Feed Flow (mL/min) | 75 |

| T3 | | T4 | |
|---|---|---|---|
| Transducers | 1 | Transducers | 2 |
| VVD | 2 | VVD | 2 |
| Perfused Flow (mL/min) | 3.8 | Perfused Flow (mL/min) | 3.8 |
| Feed Flow (mL/min) | 150 | Feed Flow (mL/min) | 150 |

Figure 25:
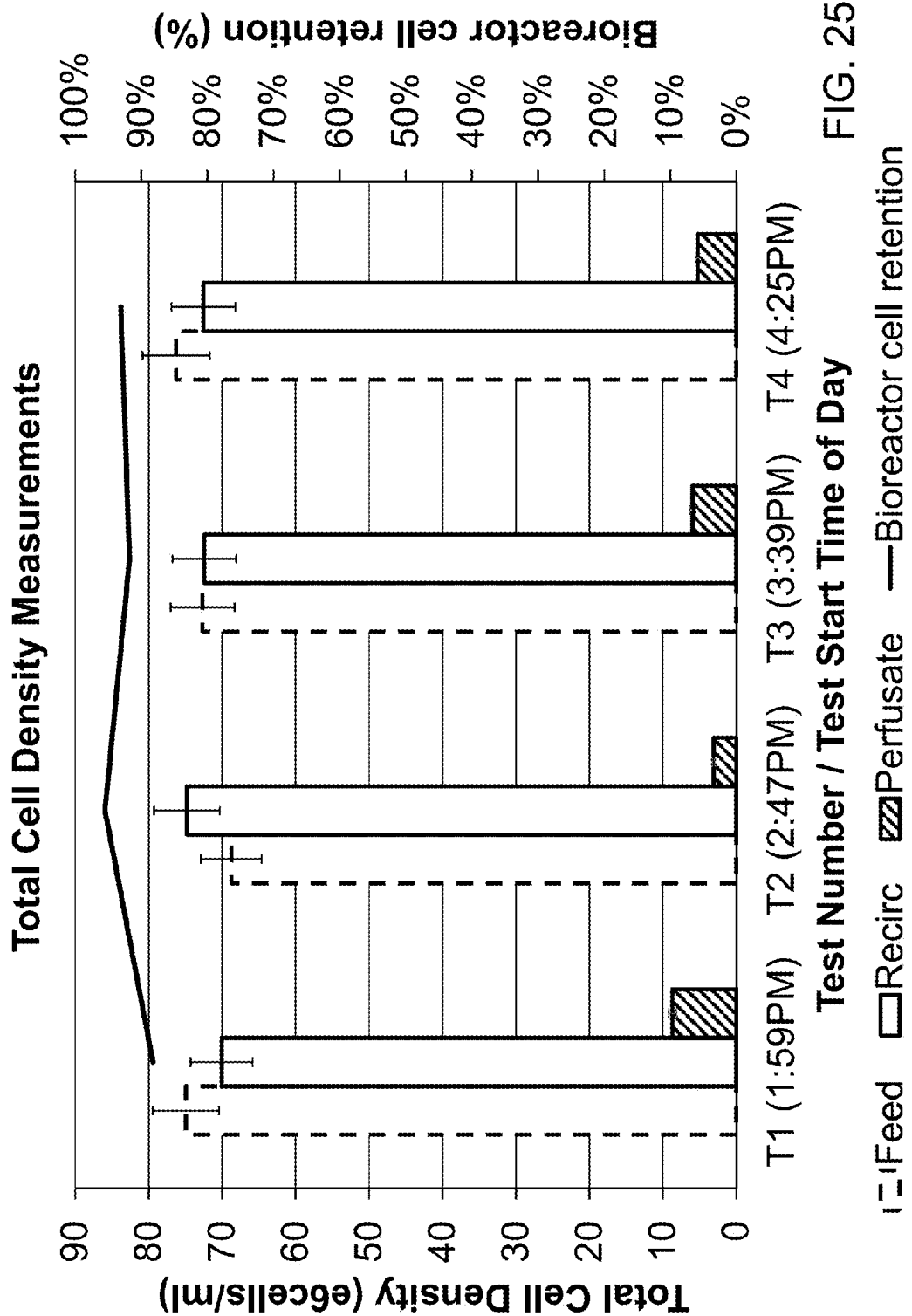
FIG. 25 is a graph showing the total cell density and cell retention for varied numbers of ultrasonic transducers for another experiment.
Figure 26:
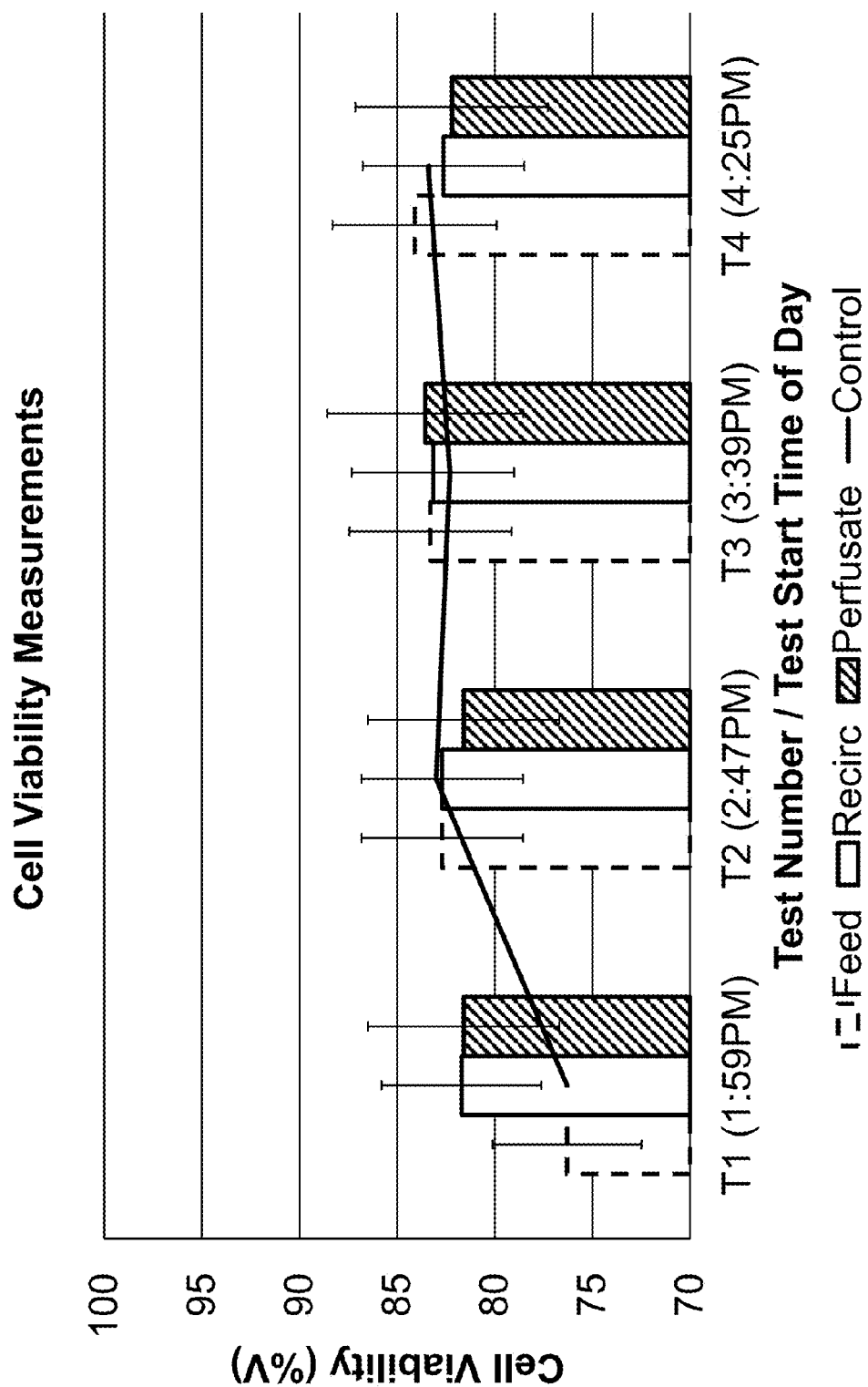
FIG. 26 is a graph showing the cell viability for varied numbers of ultrasonic transducers for the experiment conducted for the graph of FIG. 25.

FIG. 25 shows the measured total cell density of feed, recirculation, and perfusion flows. The bioreactor cell retention for the tests shows a perfusion efficiency greater than 90%. The results further evidenced an approximately 3-5% greater efficiency when using two transducers rather than a single transducer. FIG. 26 shows the measured cell viability for the tests, revealing no significant change in viability across the tests. Practically speaking, operating at low VVD offers a number of advantages, such as media cost reduction.

In biological applications, it is contemplated that all of the parts of the system (i.e., the bioreactor, acoustic filtering device, tubing fluidly connecting the same, etc.) can be separated from each other and be disposable. Avoiding centrifuges and filters allows better separation of the CHO cells without lowering the viability of the cells. The transducers may also be driven to create rapid pressure changes to prevent or clear blockages due to agglomeration of CHO cells. The frequency of the transducers may also be varied to obtain optimal effectiveness for a given power.

Example 2

Figure 27:
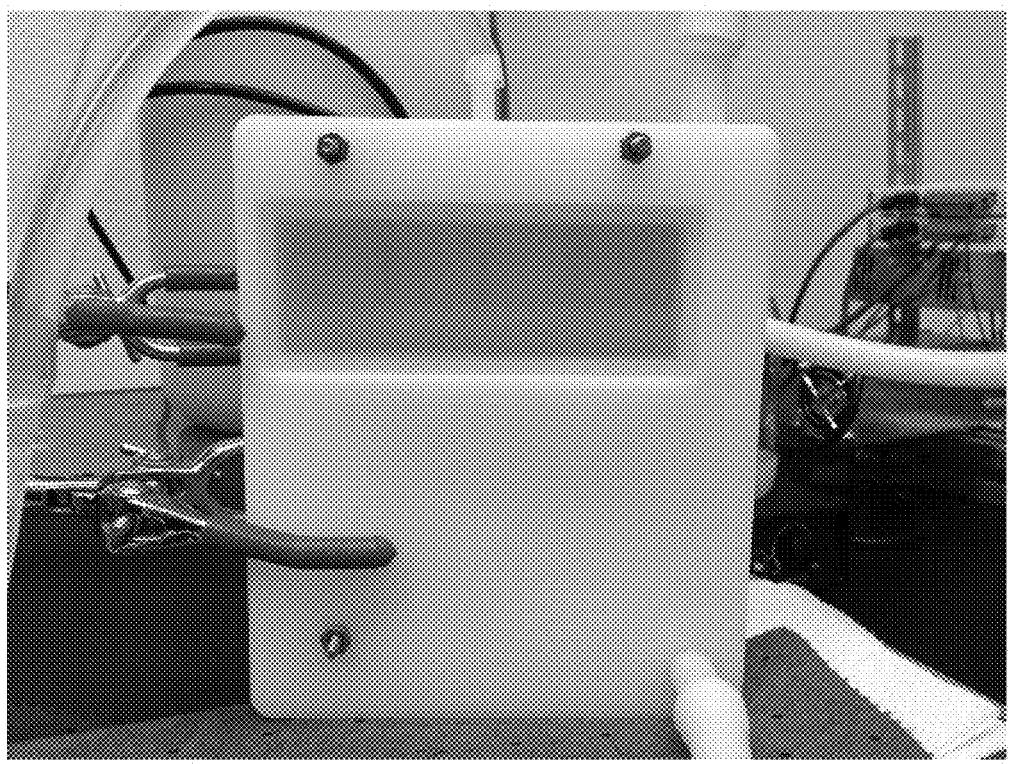
FIG. 27 is a picture of another acoustic perfusion device that was tested.

FIG. 27 shows another experimental setup for an acoustic perfusion device similar to that illustrated in FIG. 8. Tubes are connected to the inlet port, outlet port, and the collection port.

Figure 28:
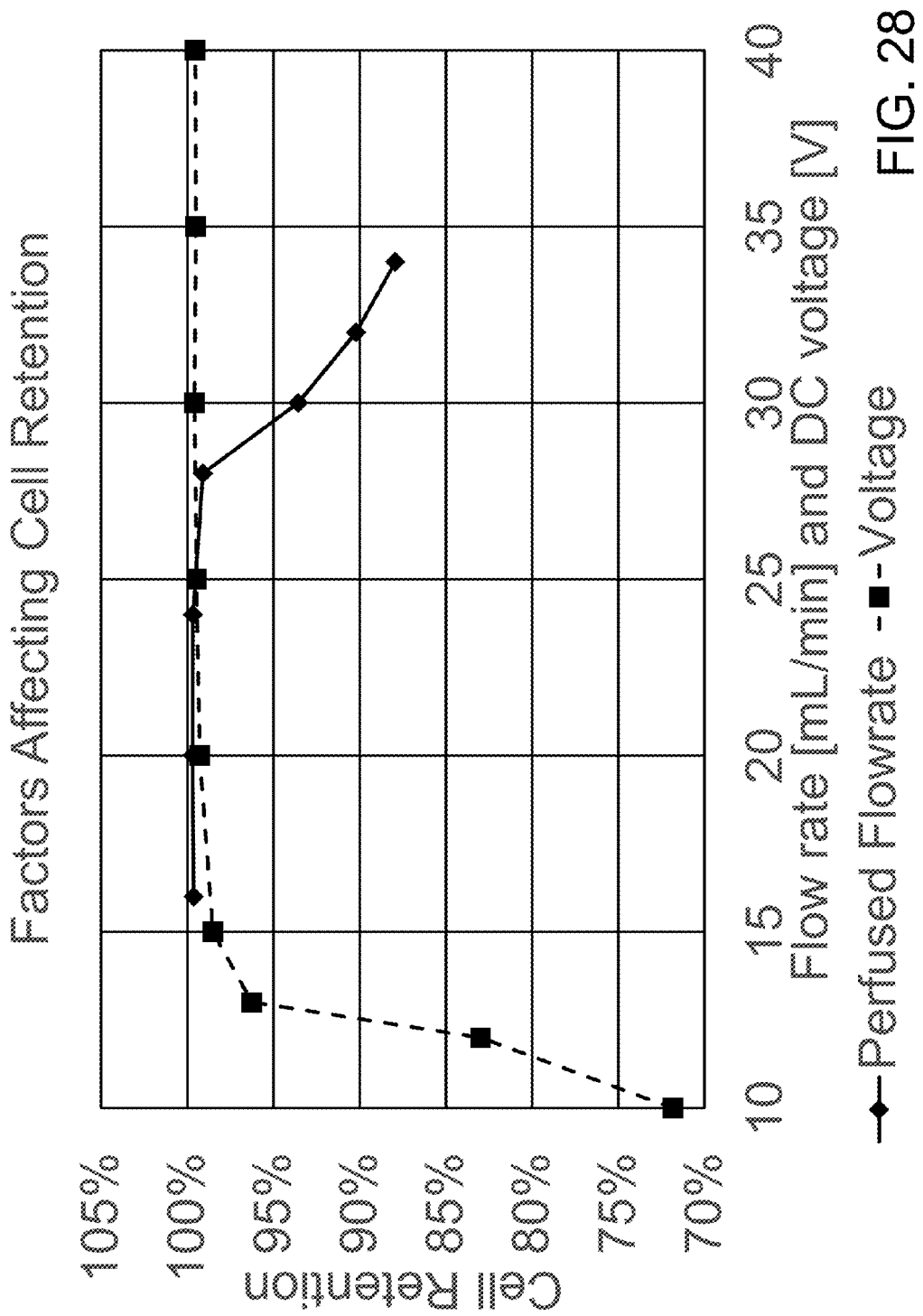
FIG. 28 is a graph showing the effect of the perfused flow rate or the transducer voltage on the cell retention.

The device was tested at a transducer voltage of 40V peak to peak, a perfused flow rate of 15-30 mL/min, and a recirculation flow rate of 2 L/min. Samples were taken every 45-60 minutes, and the cell retention rate was determined. FIG. 28 shows the results. The y-axis is the retention, stated in terms of percentage (calculated by comparing the output cell count with the input, or bioreactor/culture cell count). The x-axis is both the applied DC voltage (in V) and the perfused, or harvest, flow rate (in mL/min); it is merely coincidental that the range of numeric values for V and mL/min are the same. The cell retention efficiency remained above 95% for perfused flow rates up to 20 mL/min, and remained above 90% up to about 25 mL/min. FIG. 33 is a composite picture showing the device in a startup or cell settling mode (left) and in a steady state cell retention mode (right).

Next, experiments were performed to determine what factors would affect cell retention. The perfused flow rate was varied, as was the transducer voltage. When the perfused flow rate was varied, the transducer voltage was maintained at 40V peak to peak and the recirculation flow rate was maintained at 2 L/min. When the transducer voltage was varied, the perfused flow rate was maintained at 20 mL/min and the recirculation flow rate was maintained at 2 L/min. The results indicated that, for this particular embodiment, a perfused flow rate of about 15 mL/min to about 28 mL/min was optimum, and a transducer voltage of about 15V peak to peak to about 28V peak to peak was optimum.

Figure 29A:
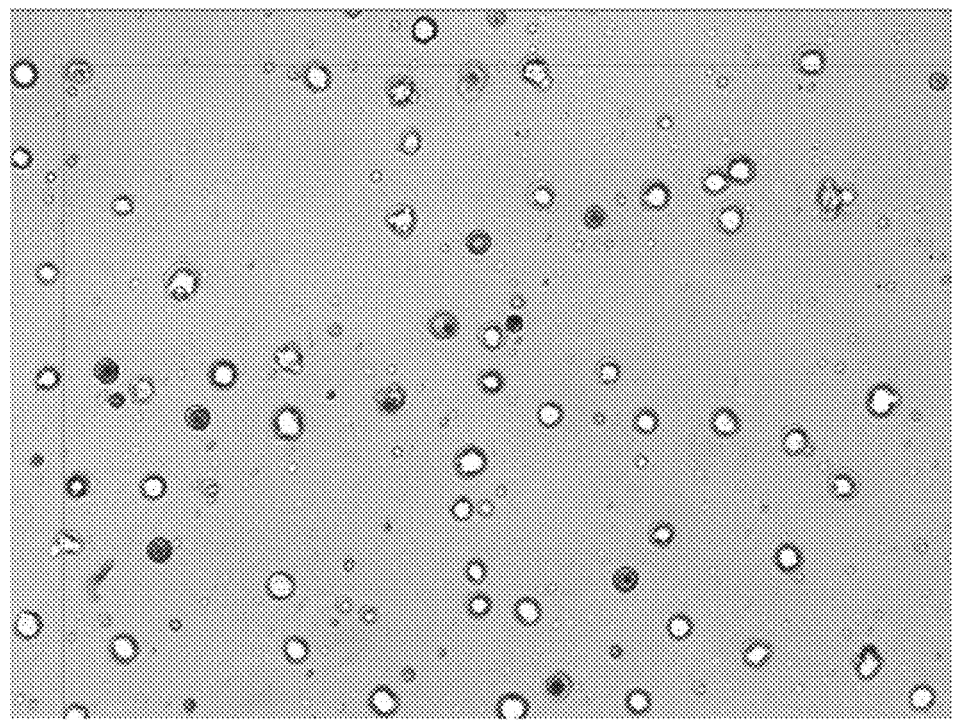
FIG. 29A is a microscope image from a ViCell Cell Analyzer of the particles in the feed stream going into the device. The feed stream is a bioreactor fluid containing CHO cells, protein, and cell fragments.
Figure 29B:
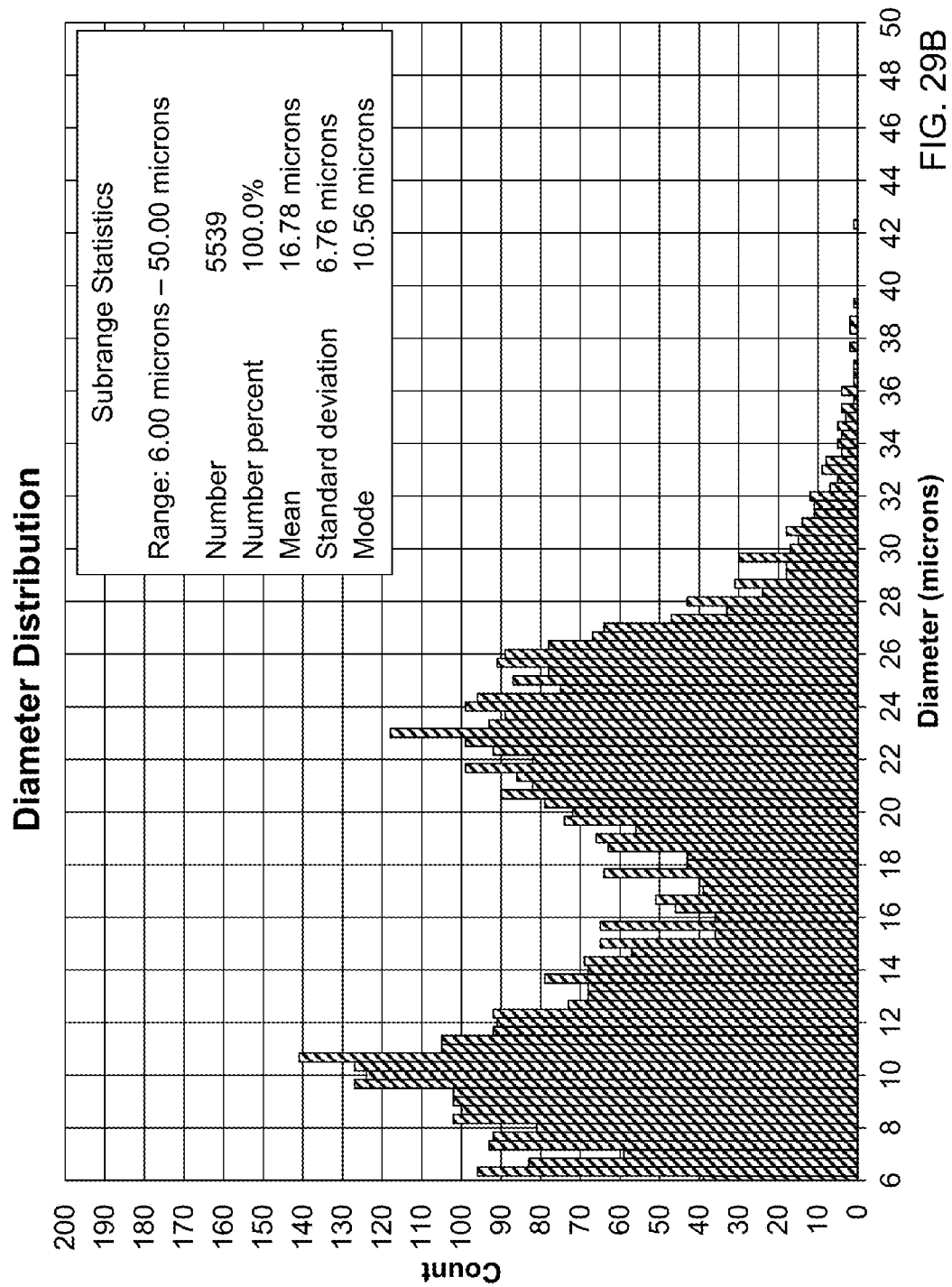
FIG. 29B is a graph of the particle diameter distribution of the feed, showing a bimodal distribution.

A better understanding of the added functionality provided by an acoustic perfusion device can be demonstrated by examining the observed cell samples coming in and being harvested from the device. FIG. 29A is a microscope image (from a Vi-Cell cell counter) of the feed suspension, here a viable cell culture population with approximately 56 million cells/mL. Several large, round, healthy cells can be observed. FIG. 29B is a histogram showing the distribution of cell diameter in the population. The diameter distribution is strongly bi-modal, around values of about 11 microns and about 23 microns. These two modes correspond roughly with the smaller debris and non-viable cells, and the larger viable cells. It should be noted that this sample is from a particularly "dirty" cell population. In general, a production cell line would be far cleaner, and the peak at approximately 11 microns would be much smaller, or even non-existent.

Figure 30A:
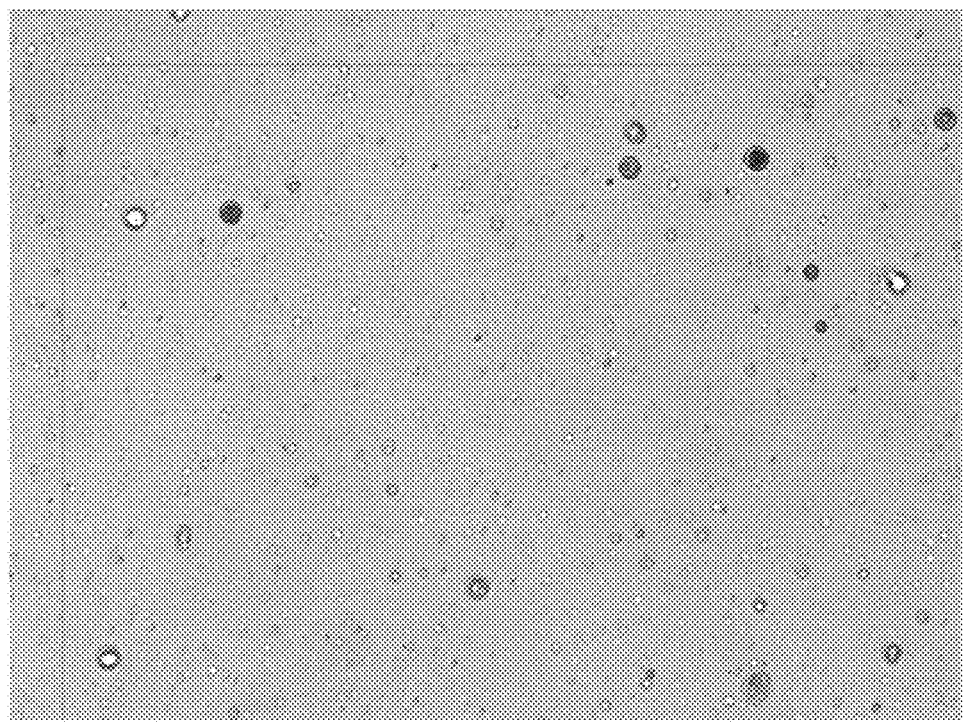
FIG. 30A is a microscope image of the perfusate (or clarified harvest flow) exiting the device.
Figure 30B:
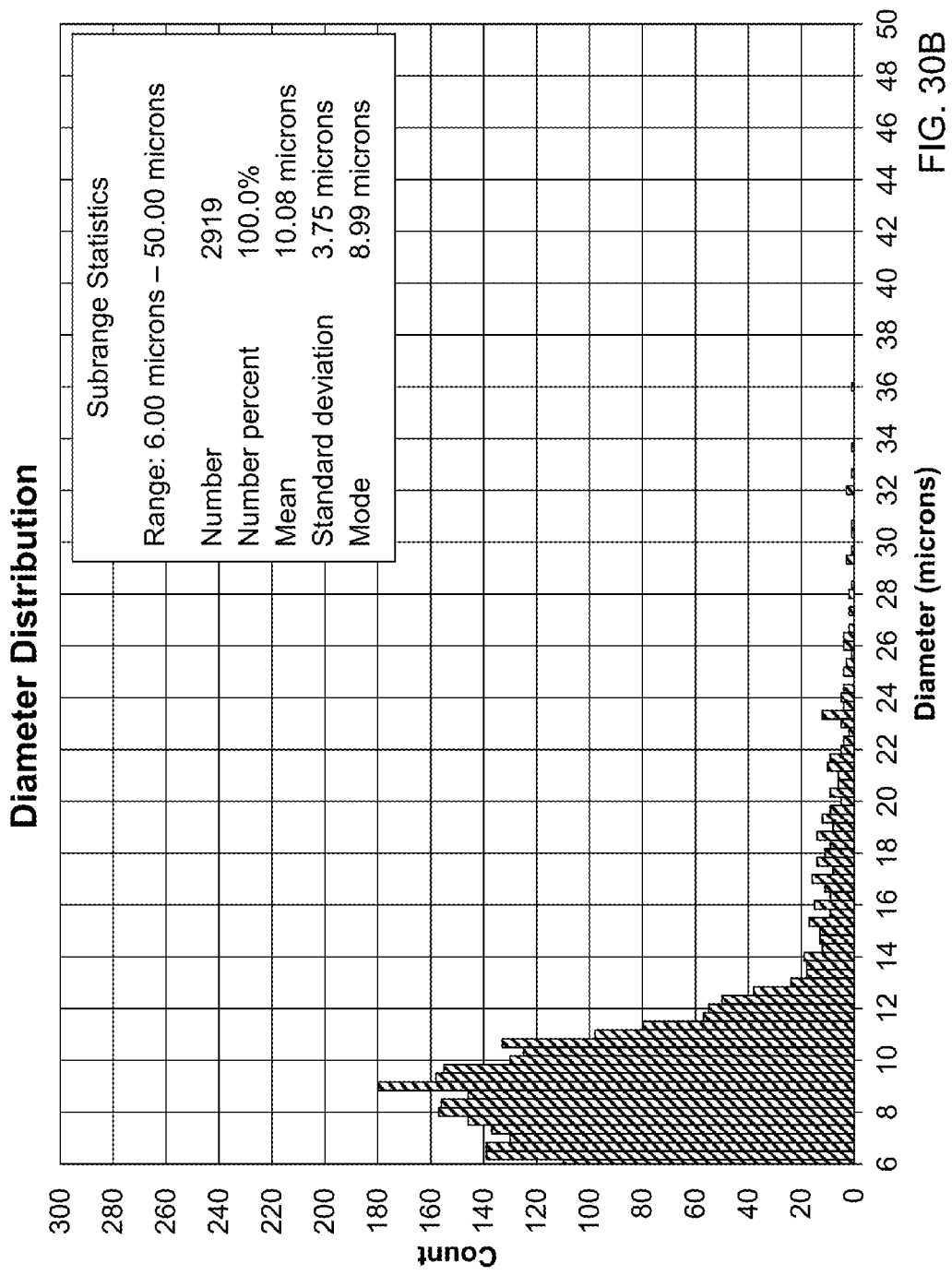
FIG. 30B is a graph of the particle diameter distribution of the perfusate, showing a unimodal distribution at much lower sizes.

FIG. 30A is another microscope image (from a Vi-Cell cell counter), this time of the flow harvested from the acoustic perfusion device. In this image, very few bright, large cells are observed, in contrast to FIG. 29A. Rather, the image is filled with more smaller, darker particles, or debris. The experimental conditions in this case were a perfused rate of 4 mL/min and a recirculation rate of 2 L/min with a DC input voltage of 30V. This qualitative observation is confirmed by the histogram in FIG. 30B, which shows the distribution of diameters in the perfusate. Looking at FIG.

30B, the particle distribution is now unimodal, with the peak of approximately 9 microns. This indicates that the larger, viable cells have been trapped and retained, or otherwise largely prevented from exiting in the perfusate. Only smaller cells are passing through, together with cell debris, fines, and fragments, from submicron to micron sized.

Figure 31:
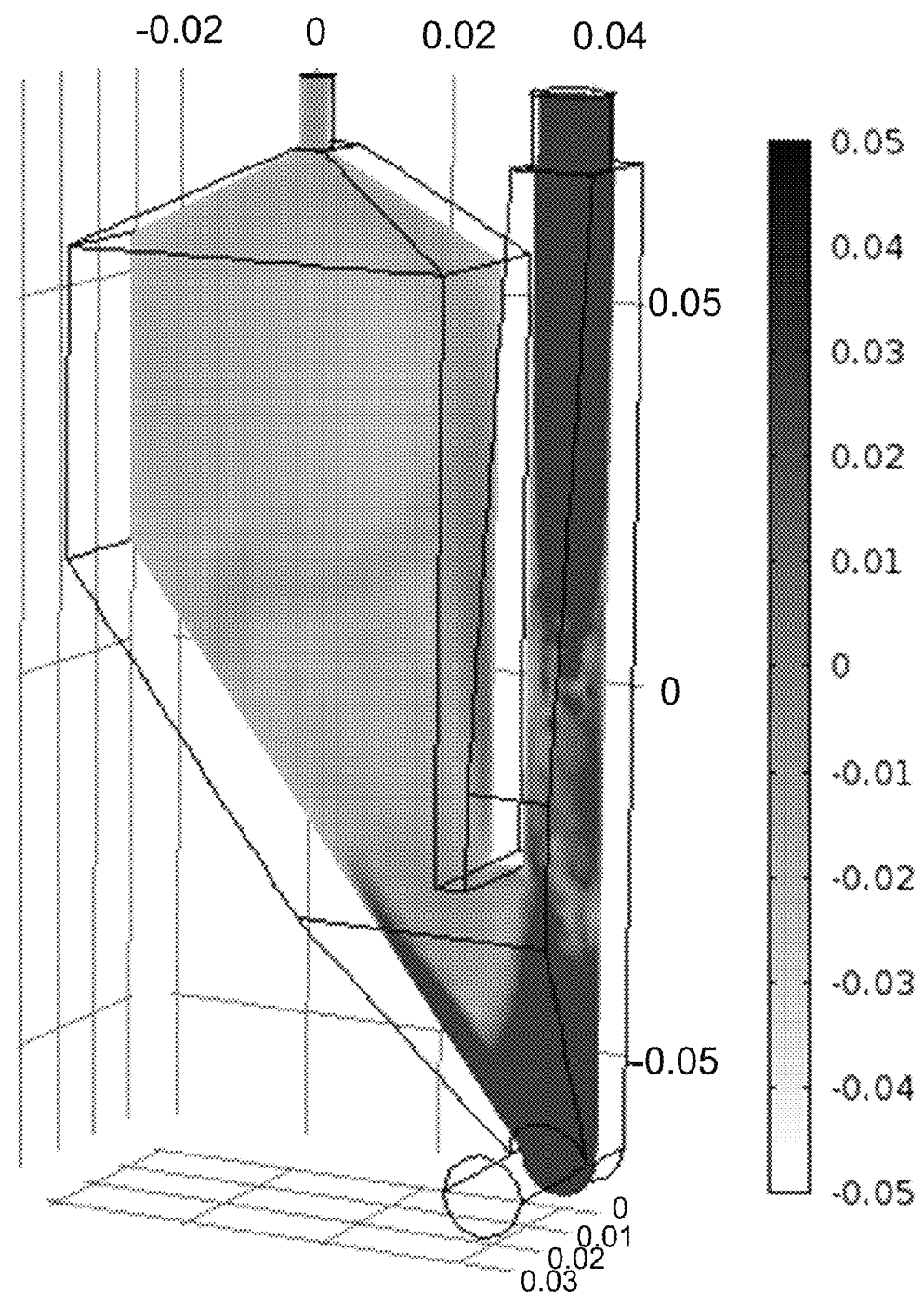
FIG. 31 is a CFD model showing the velocity distribution within the device of FIG. 27. The text at the top of the scale reads "$\times 10^{-2}$". The text at the top of the scale by the upward-pointing triangle reads "0.678". The text at the bottom of the scale by the downward-pointing triangle reads "0". The triangles show the maximum and minimum values depicted in this figure for the given scale. The scale runs from 0 to 5 m/s in intervals of 0.5, with black indicating 5 at the top of the scale, and white indicating zero at the bottom of the scale.

A computational fluid dynamics (CFD) model was made of this device. FIG. 31 shows the velocity distributions within the device after 500 seconds. The units are in meters/second (m/s). As expected, the highest velocities are found in the channel leading downwards from the inlet port to the outlet port. The velocity is near zero in the fluid cell and out through the collection port. This is important for two reasons: the acoustic field is more effective in a flow with a lower, more uniform velocity, and because the cells used in bio-manufacturing are sensitive to flow, and the induced shear rate.

FIG. 32 is a diagram illustrating several aspects of this embodiment. Fluid flows into the device through the inlet port 710 (arrow 780) and into the acoustic chamber, above the acoustic edge 783. The volume of fluid 750 below the acoustic chamber contains the tangential flow path, indicated by arrow 782. Fluid with a relatively high amount of viable cells will exit through the outlet port 730, as indicated by arrow 781. The acoustic edge effect created by the standing waves is marked with reference numeral 783, and separates large cells from smaller cell fragments, particulate debris, desired biomolecules, etc., which can pass through the acoustic standing wave field 784. This harvest flow stream 785 then exits through harvest port 770. The tangential flow path is part of the inlet flow path, and is located below the acoustic edge 783 generated by the acoustic standing wave. The tangential flow path will transport away both the clusters of cells that drop from the acoustic standing wave field 784 due to gravity effects and the cells that are retained by the acoustic edge effect.

Example 3

Another way of explaining the operation of the acoustic perfusion device can be understood by looking at the results of a numerical study. In the numerical study, two fluids with differing effective acoustic properties (i.e., speed of sound and density), were modeled with an interface between them in COMSOL, a numerical simulation software. The acoustic field is calculated and therefrom the lateral radiation force acting on a particle in the direction of the fluid velocity is calculated using Gorkov's equation.

Figure 34:
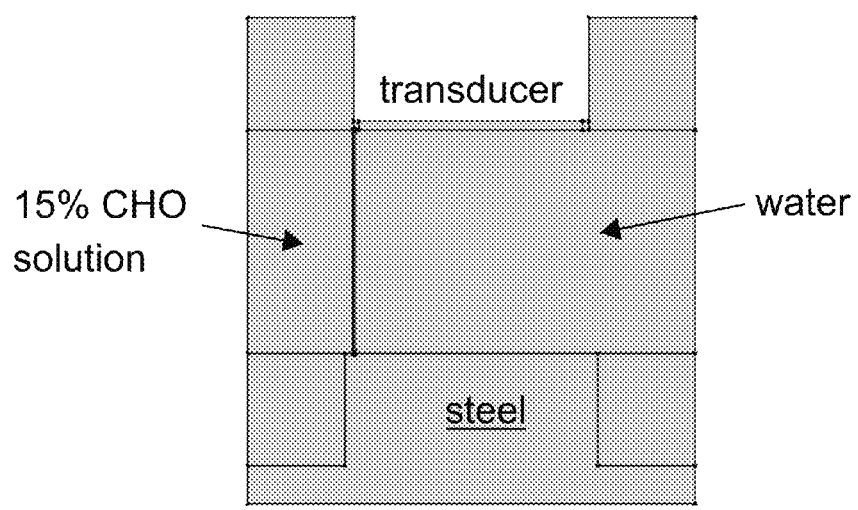
FIG. 34 shows the geometry of a model simulation of the acoustic device used for cell retention. The model contains two fluids, one a clarified fluid within the acoustic field, the other a high cell density fluid to the left of the acoustic field, a piezoelectric transducer, a steel reflector, and an aluminum housing. The first fluid was water within the acoustic field and the second fluid was a 15% concentration of CHO cells in water solution outside (to the left) of the acoustic field. The blue solid line in the model indicates the separation line between the two fluids.

FIG. 34 shows the geometry of the simulation, utilizing a piezoelectric transducer, steel reflector, aluminum housing, and two fluids: the first fluid being water within the acoustic field and the second fluid being a 15% concentration of CHO cells in water solution outside of the acoustic field, the second fluid having a higher density and higher speed of sound than the water fluid.

The two fluids were separated as indicated by the solid line in the model of FIG. 34. In this setup, the fluid velocity through the system was in a horizontal direction from left to right. Therefore, in order to act as a retention device, the acoustic field needs to generate a force on the cells that acts in the negative x-direction (i.e., opposite the fluid velocity). Water was modeled with a fluid density of 1000 kg/m$^3$ and a speed of sound of 1500 m/s. CHO cells were modeled having a density of 1050 kg/m$^3$ and a speed of sound of 1550 m/s. A coupled multi-physics numerical simulation that included a full piezoelectric simulation of the piezoelectric material, an acoustic simulation of the two fluids, and a linear elastic simulation in the steel and aluminum bodies was performed at various frequencies of excitation. The transducer was driven at a peak voltage of 40 V.

Figure 35A:
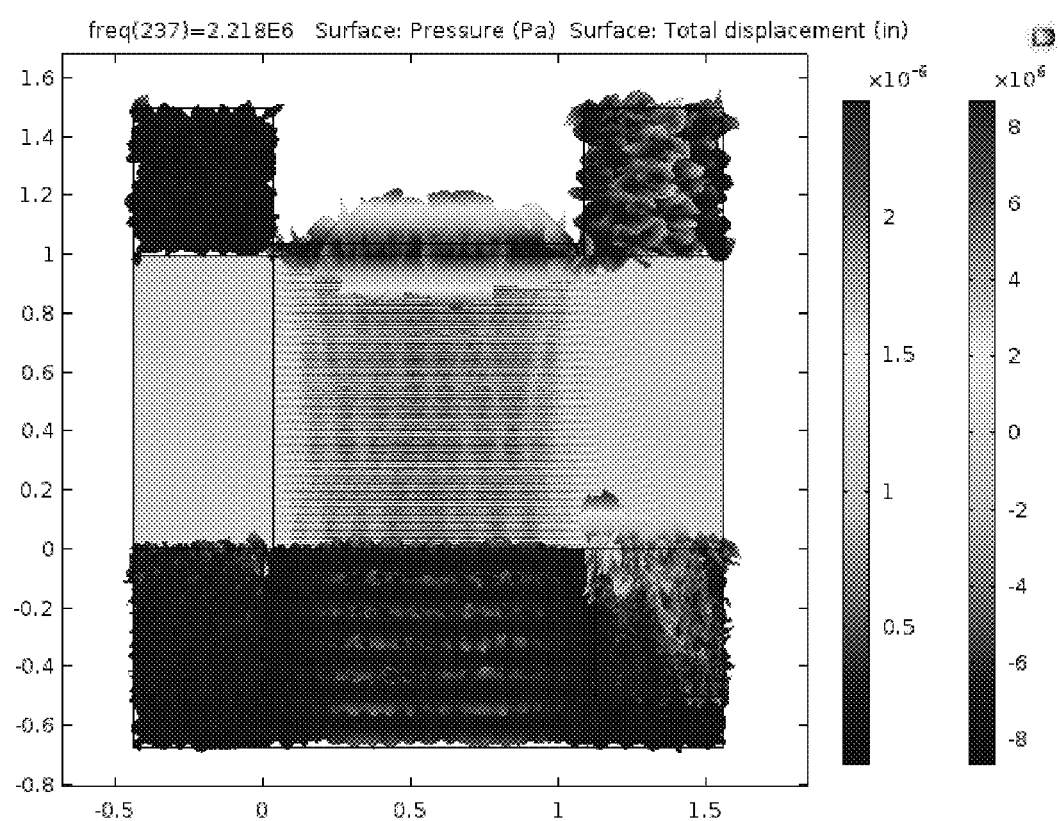
FIGS. 35A, 35B, and 35C are graphs showing the displacement of the piezoelectric material, the aluminum housing, and the steel reflector (left-side scale); and the acoustic pressure in the two fluids (right-side scale) of the model simulation of FIG. 34 at several frequencies of operation.
Figure 35B:
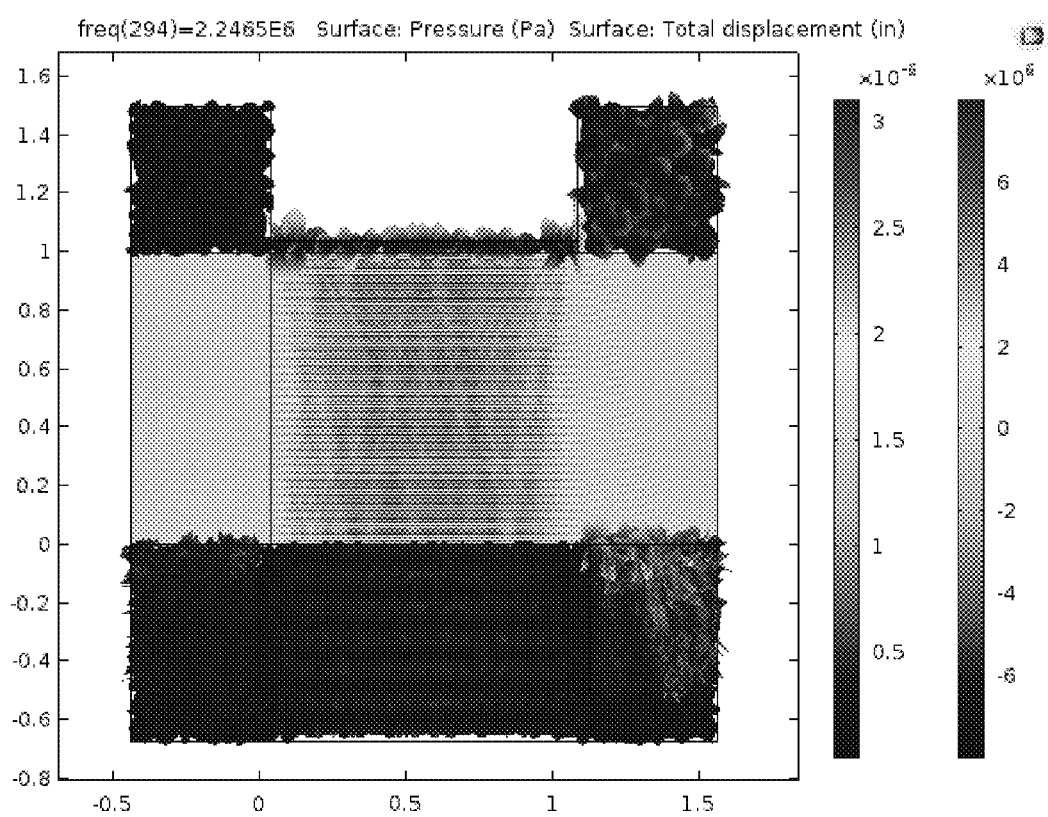
Figure 35C:
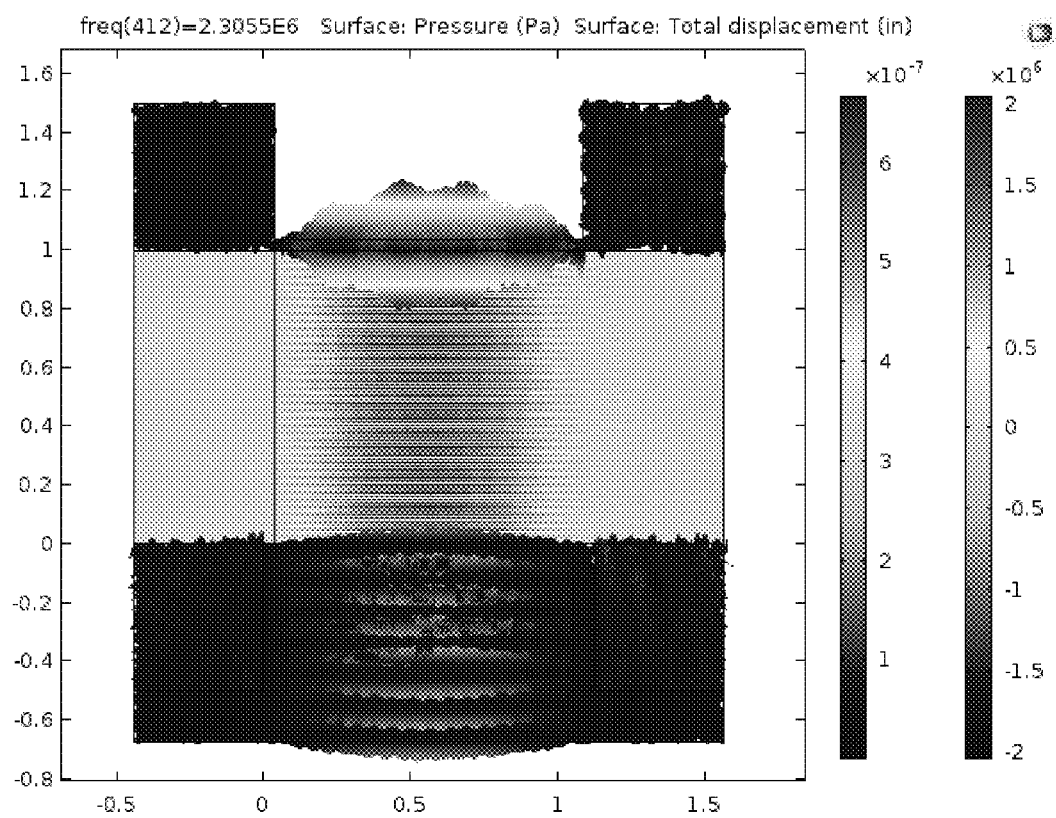

FIGS. 35A-35C show the acoustic pressure in the two fluids and the displacement of the piezoelectric material, the aluminum housing, and the steel reflector of the model at frequencies of operation of 2.218 MHz, 2.2465 MHz, and 2.3055 MHz. The lateral radiation force (i.e., horizontally in the direction of the fluid flow), was calculated at the interface between the two fluids along with real electrical power consumed by the transducer. The structural displacement of the transducer and steel are shown, along with the acoustic pressure in the fluid.

Figure 36:
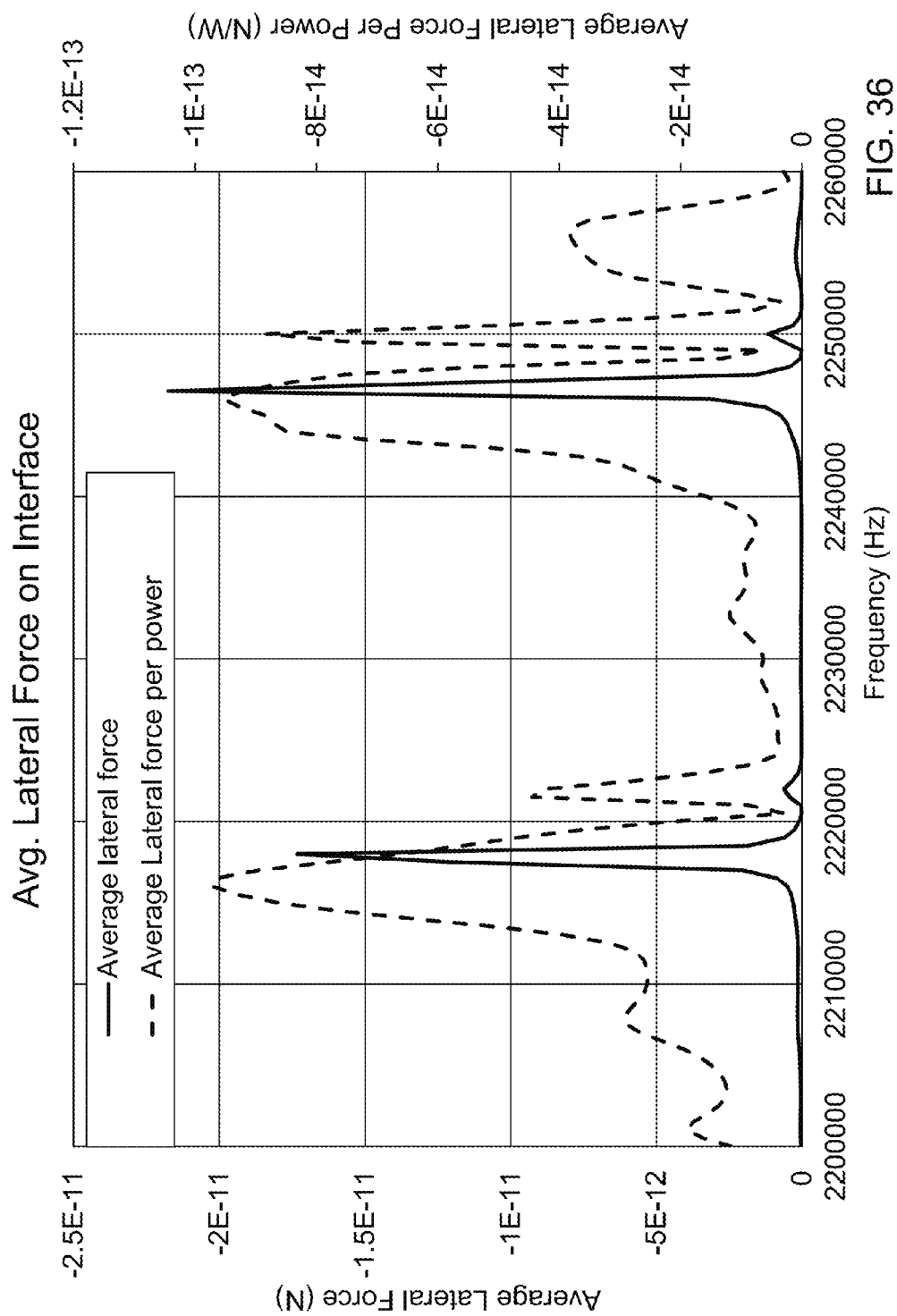
FIG. 36 is a graph showing the average lateral force (N) and the average lateral force normalized by power (N/W) acting on suspended CHO cells at several frequencies of operation.

FIG. 36 shows the lateral radiation force (N) and the lateral radiation force normalized by power (N/W) versus frequency acting on the suspended CHO cells. This graph shows that at the resonance frequencies (i.e., local maxima in power), the average lateral radiation force on the interface is negative, meaning that it is in the negative-x direction. The result is the creation of an acoustic wall effect or an acoustic edge effect. That is, the edge of the acoustic field exerts a strong lateral force on the suspended particles, thereby keeping the larger particles from entering the acoustic field and allowing only the first fluid (i.e., fluid containing only smaller particles, such as the desired product, and excluding whole cells) to enter the acoustic field, thereby creating an acoustic perfusion cell retention device. In this way, only the clarified fluid can escape and the cells are held down by the radiation force. This force is never positive, meaning that it always holds the cells down at the interface, not allowing them to escape the acoustic edge. The multiple peaks in the power curve show the existence of multiple modes of operation including planar resonance modes and multi-dimensional modes of operation, indicating that this type of operation can be generated through utilization of planar and multi-dimensional standing waves alike. In systems having 1"×1" dimensions, there exists planar resonance about every 30 kHz. The graph shows evidence of additional peaks indicating the existence of the multi-dimensional modes. Per unit power, these modes can be equally or even more effective as the planar resonance modes. As explained above, the cells that are held back by the acoustic radiation force may then be picked up by the scrubbing motion of the flow field (i.e., the recirculating flow underneath the interface), and be continuously returned to the bioreactor to ensure they receive the nutrition and oxygen to maintain the production of the overall cell culture.

Example 4

Figure 38:
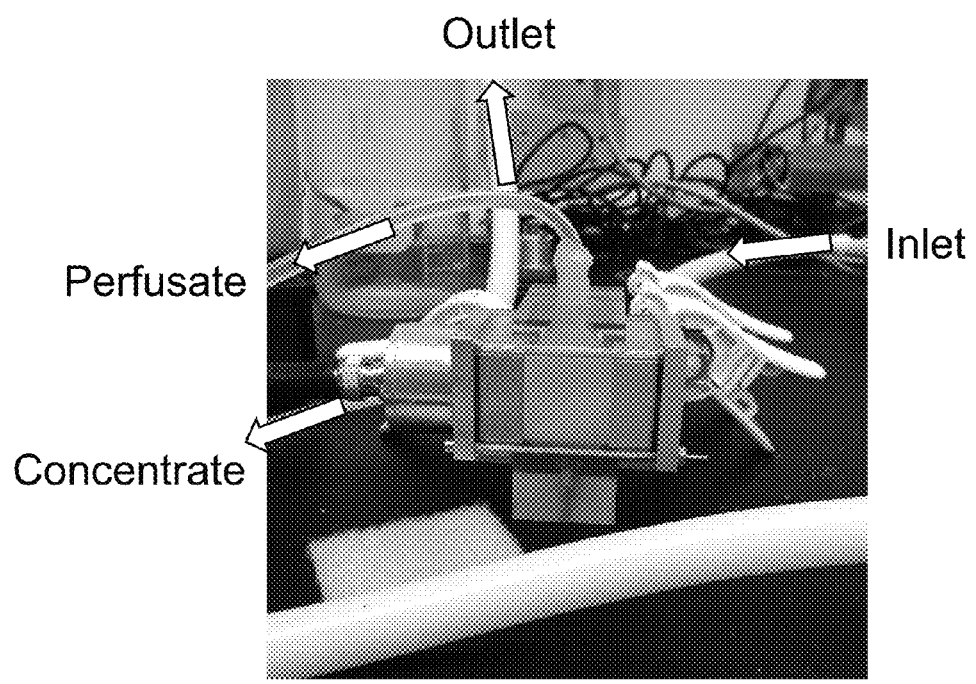
FIG. 38 is a picture (side view) of the acoustic perfusion device of FIG. 37.

FIG. 37 and FIG. 38 show another experimental setup for an acoustic perfusion device similar to that illustrated in FIG. 9. Tubes are connected to the inlet port, outlet port, the collection port, and the secondary outlet port (for a flow concentrated cells). Arrows are included to illustrate fluid flow. Arrows indicate the flow into the inlet port; the flow out of the outlet port; the perfusate flow out the top of the device and the flow of concentrate out the bottom of the device. The flow through the inlet port to the outlet port is the recirculation flowrate. The perfusate flow out the top of the device is the perfused flowrate containing clarified fluid depleted in cells and containing desired product. The flow of concentrate out the bottom of the device is the concentrated cell flow. The concentrated cell flow can be used for a cell bleed operation or if desired, the cells can be returned to the bioreactor.

Figure 39:
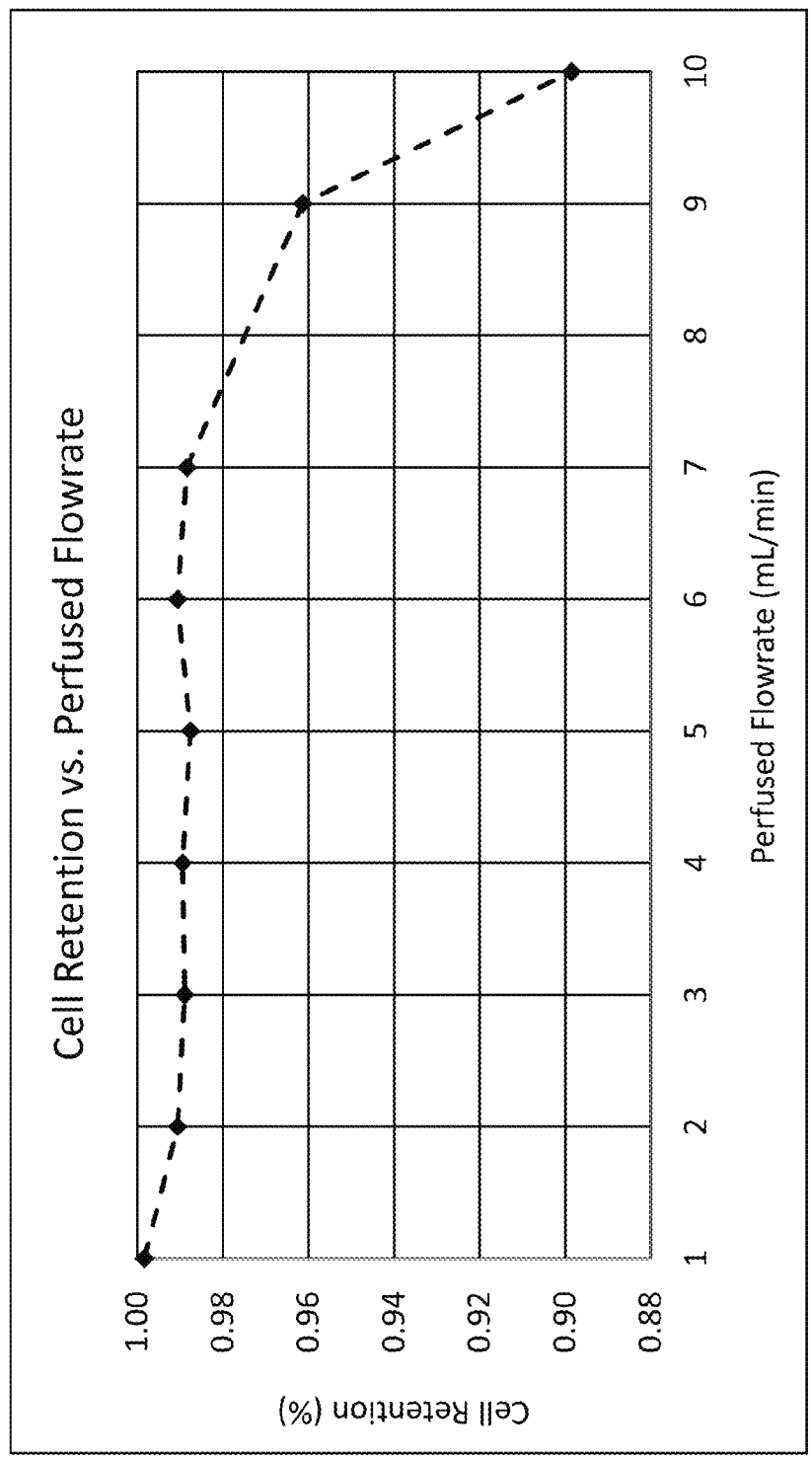
FIG. 39 is a graph of cell retention vs. perfusate flowrate for the device of FIG. 37.

The device was tested at a transducer voltage of 40V peak to peak, a perfused flow rate (out the top) of 1-10 mL/min, a recirculation flow rate of 0.75-1 L/min, and a concentrate flow rate (out the bottom) of 15 mL/min. The cell retention rate was determined for different perfused flowrates. FIG. 39 shows the results. The y-axis is the retention with 1.00 indicating 100% retention. The cell retention efficiency remained above 98% for perfused flow rates up to 7 mL/min, and was just below 90% at 10 mL/min.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustic perfusion device, comprising:
   an acoustic chamber;
   an inlet port, an inlet flow path leading from the inlet port to the acoustic chamber;
   an outlet port for recirculating a fluid/cell mixture;
   at least one collection port for collecting harvest fluid from the fluid/cell mixture; and
   at least one ultrasonic transducer and at least one reflector opposite the at least one ultrasonic transducer, wherein the at least one ultrasonic transducer includes a piezoelectric material driven by a voltage signal to create a multi-dimensional acoustic standing wave across a collection flow path leading from the acoustic chamber to the at least one collection port.

2. The device of claim 1, wherein the acoustic chamber is below the at least one collection port.

3. The device of claim 1, wherein the inlet flow path is shaped to generate a tangential flow path below an acoustic field generated by the acoustic standing wave.

4. The device of claim 1, wherein a pressure rise and an acoustic radiation force on cells are generated at an edge of the acoustic standing wave to clarify fluid passing through the acoustic standing wave.

5. The device of claim 1, wherein the at least one ultrasonic transducer is mounted in a rear wall or a front wall of the device.

6. The device of claim 1, wherein the at least one reflector is made of a transparent material.

7. The device of claim 1, wherein the outlet port is below the inlet port.

8. The device of claim 1, having a total of two or more ultrasonic transducers located on multiple sides of the collection flow path.

9. The device of claim 8, where the at least one reflector is located between the two or more ultrasonic transducers.

10. The device of claim 8, wherein the two or more ultrasonic transducers are within the collection flow path and the at least one reflector is opposite the two or more ultrasonic transducers in a wall of the device.

11. The device of claim 1, wherein the at least one transducer is an array.

12. The device of claim 1, wherein the acoustic standing wave results in an acoustic radiation force having an axial force component and a lateral force component that are of the same order of magnitude.

13. The device of claim 1, having two or more collection ports spaced apart from each other on the top end of the device.

14. The device of claim 1, further comprising a secondary flow chamber in which the harvest fluid passes through a second acoustic standing wave having a frequency higher than the first ultrasonic acoustic standing wave to further clarify the harvest fluid.

15. The device of claim 1, wherein both a planar acoustic standing wave and the multi-dimensional acoustic standing wave are created across the collection flow path.

16. A method for separating biological cells from a fluid medium, comprising:
   flowing the fluid medium containing the biological cells through an acoustic perfusion device, the device comprising:
      an acoustic chamber;
      an inlet port, an inlet flow path leading from the inlet port to the acoustic chamber;
      an outlet port for recirculating the fluid medium and the biological cells;
      at least one collection port for collecting harvest fluid; and
      at least one ultrasonic transducer below the at least one collection port and at least one reflector opposite the at least one ultrasonic transducer, wherein the at least one ultrasonic transducer includes a piezoelectric material driven by a voltage signal to create a multi-dimensional acoustic standing wave across a collection flow path leading from the acoustic chamber to the at least one collection port;
   driving the at least one ultrasonic transducer to create the acoustic standing wave; and
   collecting a fluid enriched in cells from the outlet port and collecting a harvest fluid depleted in cells from the at least one collection port.

17. The method of claim 16, wherein the outlet port is below the inlet port.

18. The method of claim 16, wherein a flow rate through the collection flow path is at least one order of magnitude smaller than a flow rate through the inlet flow path.

19. The method of claim 16, wherein the inlet flow path leads from the inlet port downwards towards the outlet port and then upwards to the acoustic chamber, creating a recirculating fluid stream that is locally substantially tangential to the at least one acoustic standing wave.

20. The method of claim 19, wherein the recirculating fluid stream transports away cells that are constantly dropping from an edge region of the acoustic standing wave.

21. The method of claim 16, wherein a pressure rise and an acoustic radiation force on cells are generated at an edge of the acoustic standing wave to clarify fluid passing through the acoustic standing wave.

22. The method of claim 16, wherein a flow rate of the fluid medium entering the device through the inlet port is about 1 liter per minute and a flow rate of the harvest fluid depleted in cells exiting the device through the at least one collection port is about 10 milliliters per minute.

23. The method of claim 16, further comprising a secondary flow chamber in which the harvest fluid passes through a second acoustic standing wave having a frequency higher than the first ultrasonic acoustic standing wave to further clarify the harvest fluid.

24. A flow device adapted to receive a flowing mixture containing a primary fluid and cells, comprising a single ultrasonic transducer to create a first multi-dimensional acoustic standing wave to continuously draw off a harvest fluid stream depleted in cells from the flowing mixture, thereby changing the cell concentration of the flowing mixture.

25. The device of claim 24, wherein both a planar wave and the first multi-dimensional acoustic standing wave are created across a flow path to obtain the harvest fluid stream.

26. The device of claim 24, wherein a pressure rise and an acoustic radiation force on cells are generated at an edge of the first acoustic standing wave to clarify the flowing mixture passing through the standing wave.

27. The device of claim 24, further comprising a secondary flow chamber in which the harvest fluid stream depleted in cells passes through a second acoustic standing wave having a frequency higher than the first acoustic standing wave.

28. A flow device, comprising:
   at least one inlet for receiving a flowing mixture of a primary fluid and cells,
   an ultrasonic transducer that produces a first ultrasonic multi-dimensional acoustic standing wave and uses a pressure rise and an acoustic radiation force on cells, generated at an edge of the first ultrasonic multi-dimensional acoustic standing wave, to separate the flowing mixture into a primary high cell concentration fluid stream and a secondary harvest fluid stream;
   an outlet port for the primary high cell concentration fluid stream;
   a bleed port for extracting a concentrated fluid/cell mixture; and
   at least one collection port for the secondary harvest fluid stream.

29. The device of claim 28, further comprising a secondary flow chamber in which the secondary harvest fluid stream passes through a second acoustic standing wave having a frequency higher than the first ultrasonic acoustic standing wave.

30. The device of claim 29, where the secondary flow chamber is utilized to further clarify the secondary harvest fluid stream by trapping and agglomerating materials having a size of about 10 microns or less, such that the agglomerated material separates from the secondary harvest fluid stream due to gravity.

* * * * *